US010293043B2

(12) United States Patent
Mumm et al.

(10) Patent No.: US 10,293,043 B2
(45) Date of Patent: May 21, 2019

(54) METHODS OF LOWERING SERUM CHOLESTEROL

(71) Applicant: ARMO BioSciences, Inc., Redwood City, CA (US)

(72) Inventors: John Brian Mumm, Los Altos Hills, CA (US); Ivan Ho Chan, Redwood City, CA (US)

(73) Assignee: Armo Biosciences, Inc., Redwood City, CA (US)

( * ) Notice: Subject to any disclaimer, the term of this patent is extended or adjusted under 35 U.S.C. 154(b) by 0 days.

(21) Appl. No.: 15/313,465

(22) PCT Filed: May 6, 2015

(86) PCT No.: PCT/US2015/029523
§ 371 (c)(1),
(2) Date: Nov. 22, 2016

(87) PCT Pub. No.: WO2015/187295
PCT Pub. Date: Dec. 10, 2015

(65) Prior Publication Data
US 2017/0296653 A1 Oct. 19, 2017

Related U.S. Application Data

(60) Provisional application No. 62/006,651, filed on Jun. 2, 2014.

(51) Int. Cl.
C12Q 1/60 (2006.01)
C07K 14/47 (2006.01)
A61K 38/00 (2006.01)
A61K 38/17 (2006.01)
A61K 38/20 (2006.01)
G01N 33/50 (2006.01)
A61K 39/385 (2006.01)
A61K 49/00 (2006.01)
C07K 14/715 (2006.01)
C07K 17/02 (2006.01)
A61K 47/60 (2017.01)
G01N 33/92 (2006.01)
A61K 48/00 (2006.01)

(52) U.S. Cl.
CPC ........ A61K 39/385 (2013.01); A61K 38/1796 (2013.01); A61K 38/2066 (2013.01); A61K 47/60 (2017.08); A61K 49/0008 (2013.01); C07K 14/4705 (2013.01); C07K 14/4718 (2013.01); C07K 14/715 (2013.01); C07K 17/02 (2013.01); G01N 33/5055 (2013.01); A61K 38/00 (2013.01); A61K 48/00 (2013.01); C12Q 1/60 (2013.01); G01N 33/92 (2013.01)

(58) Field of Classification Search
None
See application file for complete search history.

(56) References Cited

U.S. PATENT DOCUMENTS

| 4,965,195 A | 10/1990 | Namen et al. |
| 5,032,396 A | 7/1991 | Williams |
| 5,229,115 A | 7/1993 | Lynch |
| 5,231,012 A | 7/1993 | Mosmann et al. |
| 5,252,714 A | 10/1993 | Harris et al. |
| 5,328,989 A | 7/1994 | Vellekamp et al. |
| 5,552,303 A | 9/1996 | Grabstein et al. |
| 5,624,823 A | 4/1997 | Sachs et al. |
| 5,643,575 A | 7/1997 | Martinez et al. |
| 5,665,345 A | 9/1997 | Yarchoan et al. |
| 5,696,234 A | 12/1997 | Zurawski et al. |
| 5,705,149 A | 1/1998 | Namen et al. |
| 5,710,251 A | 1/1998 | Vellekamp et al. |
| 5,759,859 A | 6/1998 | Leder et al. |
| 5,824,784 A | 10/1998 | Kinstler et al. |
| 5,866,134 A | 2/1999 | Fine et al. |
| 5,876,969 A | 3/1999 | Fleer et al. |
| 5,908,621 A | 6/1999 | Glue et al. |
| 5,919,455 A | 7/1999 | Greenwald et al. |
| 5,932,462 A | 8/1999 | Harris et al. |
| 5,945,097 A * | 8/1999 | Cutler ................ A61K 38/2066 424/85.2 |
| 5,951,974 A | 9/1999 | Gilbert et al. |
| 5,985,263 A | 11/1999 | Lee et al. |

(Continued)

FOREIGN PATENT DOCUMENTS

| CN | 1760209 | 10/2004 |
| CN | 102145178 | 8/2011 |

(Continued)

OTHER PUBLICATIONS

Gotoh et al. A novel anti-inflammatory role for spleen-derived Interleukin-10 in obesity-induced inflammation in white adipose tissue and liver, Diabetes, 61, 1994-2003, 2012. (Year: 2012).*
Kumagai et al. Effects of Ezetimibe on hypercholesterolemia in the lipid profile in patients with metabolic syndrome. IJC Metabolic and endocrine. 1, 7-12, 2013. (Year: 2013).*
Dinant et al. (IL-10 attenuates hepatic I/R injury and promotes Hepatocyte proliferation. J. Surg. Res. 141, 176-182, 2007. (Year: 2007).*
Cintra et al. (Interleukin-10 is a protective factor against diet-induced insulin resistance in liver. J. Hepatol. 48 628-637, 2008. (Year: 2008).*

(Continued)

Primary Examiner — Elly-Gerald Stoica
(74) Attorney, Agent, or Firm — Robert Brian Johnson

(57) ABSTRACT

Methods of treating subjects having diseases, disorders, or conditions, including disorders associated with cholesterol homeostasis, responsive to agents modulating Kupffer cell function, including methods of administration and dosing regimens associated therewith, are provided. Methods of treating subjects having liver diseases, disorders, or conditions, including non-alcoholic steatohepatitis and non-alcoholic fatty liver disease, with an IL-10 agent are also provided.

26 Claims, 10 Drawing Sheets

Specification includes a Sequence Listing.

(56) References Cited

U.S. PATENT DOCUMENTS

| | | | |
|---|---|---|---|
| 5,985,265 A | 11/1999 | Kinstler et al. | |
| 5,985,857 A | 11/1999 | Kinstler et al. | |
| 5,989,867 A | 11/1999 | Knappe et al. | |
| 6,156,301 A | 12/2000 | Namen et al. | |
| 6,217,857 B1 | 4/2001 | Mosmann et al. | |
| 6,387,364 B1 | 5/2002 | Ferguson | |
| 6,428,985 B1 | 8/2002 | Bromberg et al. | |
| 6,660,258 B1 | 12/2003 | Tovey | |
| 6,685,931 B1 | 2/2004 | Grint et al. | |
| 6,770,272 B2 | 8/2004 | Strom et al. | |
| 6,989,377 B2 | 1/2006 | Hayes et al. | |
| 7,052,684 B2 | 5/2006 | Ferguson | |
| 7,052,686 B2 | 5/2006 | Lee et al. | |
| 7,056,701 B2 | 6/2006 | Fleer et al. | |
| 7,261,882 B2 | 8/2007 | Watkins | |
| 7,585,947 B2 | 9/2009 | Morre et al. | |
| 7,589,179 B2 | 9/2009 | Gillies et al. | |
| 7,611,700 B2 | 12/2009 | Gantier et al. | |
| 7,650,243 B2 | 1/2010 | Gantier et al. | |
| 7,666,400 B2 | 2/2010 | Chang et al. | |
| 7,708,985 B2 | 5/2010 | Morre et al. | |
| 7,749,490 B2 | 7/2010 | Sommer et al. | |
| 7,939,056 B2 | 5/2011 | Horwitz et al. | |
| 8,044,175 B2 | 10/2011 | Dransfield et al. | |
| 8,067,532 B2 | 11/2011 | MacLean | |
| 8,178,713 B2 * | 5/2012 | Miller | A61K 9/1272 436/71 |
| 8,618,256 B2 | 12/2013 | Cox | |
| 2002/0044921 A1 * | 4/2002 | Lee | C07K 14/5428 424/85.2 |
| 2003/0012775 A1 | 1/2003 | Brandt et al. | |
| 2003/0186386 A1 | 10/2003 | Hansen et al. | |
| 2004/0101965 A1 | 5/2004 | Griesenbach et al. | |
| 2004/0213795 A1 | 10/2004 | Collins et al. | |
| 2005/0008615 A1 | 1/2005 | Bam et al. | |
| 2005/0164352 A1 | 7/2005 | Lauder et al. | |
| 2005/0260767 A1 | 11/2005 | Clerici et al. | |
| 2006/0046961 A1 | 3/2006 | McKay et al. | |
| 2006/0078942 A1 | 4/2006 | Liu et al. | |
| 2006/0210534 A1 | 9/2006 | Lee et al. | |
| 2006/0258607 A1 | 11/2006 | Jarosch et al. | |
| 2007/0134197 A1 | 6/2007 | Eichner et al. | |
| 2008/0058246 A1 | 3/2008 | Bhaskaran et al. | |
| 2008/0069797 A1 | 3/2008 | Roncarolo et al. | |
| 2008/0081031 A1 | 4/2008 | Oft et al. | |
| 2008/0096252 A1 | 4/2008 | Zamost et al. | |
| 2009/0035256 A1 | 2/2009 | Sommer et al. | |
| 2009/0214463 A1 | 8/2009 | Slobedman et al. | |
| 2009/0214471 A1 | 8/2009 | Oft et al. | |
| 2009/0311187 A1 | 12/2009 | Berman et al. | |
| 2010/0068147 A1 | 3/2010 | Hibberd et al. | |
| 2010/0111898 A1 | 5/2010 | Pelura | |
| 2010/0129386 A1 | 5/2010 | Elson et al. | |
| 2010/0255496 A1 | 10/2010 | Schrader et al. | |
| 2010/0266532 A1 | 10/2010 | Ferguson | |
| 2010/0297070 A1 | 11/2010 | Dugan et al. | |
| 2011/0009589 A1 | 1/2011 | Harris et al. | |
| 2011/0250163 A1 * | 10/2011 | Blaisdell | A61K 38/2066 424/78.17 |
| 2011/0312010 A1 | 12/2011 | Manuilov | |
| 2012/0142033 A1 | 6/2012 | Fujiwara | |
| 2012/0213793 A1 | 8/2012 | Huang et al. | |
| 2014/0314795 A1 | 10/2014 | Riddell et al. | |
| 2014/0349402 A1 | 11/2014 | Cooper et al. | |
| 2015/0038678 A1 | 2/2015 | Eaton et al. | |
| 2015/0118244 A1 | 4/2015 | Shahabi et al. | |
| 2016/0340406 A1 | 11/2016 | Zhao et al. | |
| 2016/0361415 A1 | 12/2016 | Mumm et al. | |
| 2016/0375101 A1 | 12/2016 | Oft | |

FOREIGN PATENT DOCUMENTS

| | | | |
|---|---|---|---|
| EP | 0251304 | 1/1988 | |
| EP | 1662003 A2 * | 5/2006 | C07K 14/5428 |
| EP | 2066336 | 9/2012 | |
| EP | 2537933 | 12/2012 | |
| WO | WO 1992012725 | 8/1992 | |
| WO | WO 1992012726 | 8/1992 | |
| WO | 1994022473 | 3/1994 | |
| WO | 199417773 | 8/1994 | |
| WO | WO 1995/03411 | 2/1995 | |
| WO | WO 1995006058 | 3/1995 | |
| WO | WO 1995019780 | 7/1995 | |
| WO | WO 1996011953 | 4/1996 | |
| WO | WO 1997003690 | 2/1997 | |
| WO | WO 1999032134 | 7/1999 | |
| WO | WO 2001005821 | 1/2001 | |
| WO | WO 2001058950 | 8/2001 | |
| WO | WO 2002026265 | 4/2002 | |
| WO | 2002085300 | 10/2002 | |
| WO | WO 2004044006 | 5/2004 | |
| WO | WO 2004/056850 | 7/2004 | |
| WO | 2004091517 | 10/2004 | |
| WO | 2004106486 | 12/2004 | |
| WO | 2005033307 | 4/2005 | |
| WO | WO 2006/075138 | 7/2006 | |
| WO | 2006094530 | 9/2006 | |
| WO | WO 2006119170 | 11/2006 | |
| WO | WO 2008054585 | 5/2008 | |
| WO | WO 2009/016043 | 2/2009 | |
| WO | WO 2009/036568 | 3/2009 | |
| WO | 2010022227 | 2/2010 | |
| WO | WO 2010/077853 | 7/2010 | |
| WO | WO 2011/051489 | 5/2011 | |
| WO | 2011159878 | 12/2011 | |
| WO | WO 2012/004384 | 1/2012 | |
| WO | WO 2012/050923 | 4/2012 | |
| WO | WO 2012/050930 | 4/2012 | |
| WO | WO 2013/113008 | 8/2013 | |
| WO | 2013130913 | 9/2013 | |
| WO | 2014172392 | 10/2014 | |
| WO | 2014176373 | 10/2014 | |
| WO | WO 2014/172392 | 10/2014 | |
| WO | 2014204816 | 12/2014 | |
| WO | 2015031316 | 3/2015 | |
| WO | WO 2015/070060 | 5/2015 | |
| WO | 2015153753 | 10/2015 | |
| WO | 2016145388 | 9/2016 | |

OTHER PUBLICATIONS

Chang, et al., (2017) "CARs: Synthetic immunoreceptors for cancer therapy and beyond", Trends Mol. Med., 23:430-450.

Hermanson, et al., (2015) "Utilizing chimeric antigen receptors to direct natural killer cell activity", Frontiers in Immunology, 6:195.

Jaspers, et al., (2017) "Development of CART cells designed to improve antitumor efficacy and safety", Pharmac. & Therap., http://dx.doi.org,/1 0.1 016/j.pharmthera.2017.03.012.

Jensen, et al., (2015) "Designing chimeric antigen receptors to effectively and safely target tumors", Curr. Opin. Immunol., 33:9-15.

Chmielewski, et al, (2015) "TRUCKs: the fourth generation of CARs", Exp. Opin. Bioi. Ther., 15:1145-1154.

Hombach, et al., (2012) "OX40 costimulation by a chimeric antigen receptor abrogates CD28 and IL-2 induced IL-10 secretion by redirected CD4+ T cells", OncoImmunol., 1:458-466.

Newick, et al., (2016) "CART cell therapy for solid tumors", Annu. Rev. Med., 68:139-152.

Gill, et al., (2015) "Going Viral: chimeric antigen receptor T-cell therapy for hematological malignancies", Immunol. Rev., 263:68-89.

Accession NP_036986.2; GI 148747382; dated Aug. 10, 2014.
Accession NP_776513.1; GI 41386772; dated Jan. 4, 2015.
Accession NP_001009327.1; GI 57164347; dated Feb. 13, 2011.
Accession ABY86619.1; GI 166244598 ; dated Feb. 4, 2008.
Accession AAC23839.1; GI 3242896; dated Jun. 8, 2000.

Mattos et al.: 11 PEGylation of interleukin-10 improves the pharmacokinetic profile and enhances the antifibrotic effectivity in eel-induced fibrogenesis in mice, Journal of Controlled Release, Elsevier, Amsterdam, NL, vol. 162, No. I, May 24, 2012 (May 24, 2012), pp. 84-91.

(56) References Cited

OTHER PUBLICATIONS

"Guidance for Industry Immunogenicity Assessment for Therapeutic Protein Products," (2013) *FDA Guidances*. "Highlights of Prescribing Information," (1997) *Rituxan*.
Recombinant Human IL-1 0 Protein, CF R&D Systems, accessed Feb. 22, 2016.
Recombinant Mouse I L -1 0 Protein R&D Systems, accessed Feb. 22, 2016.
Agata et al. (1996) "Expression of the PD-1 antigen on the surface of stimulated mouse T and B lymphocytes," *Int Immunol*; 8(5):765-772.
Aggen (2010) "Engineering Human Single-Chain T Cell Receptors," *Dissertation*; http://hdl.handle.net/2142/18585.
Alvarez et al. (2012) "Effects of PEGylation and Immune Complex Formation on the Pharmacokinetics and Biodistribution of Recombinant Interleukin10 in Mice," *Drug Metab Dispos*; 40(2):360-373.
Ansari and Raghava (2010) "Identification of conformational B-cell Epitopes in an antigen from its primary sequence," *Immunome Res*; 6:9pgs.
Ansell et al. (2002) "Phase 1 study of interleukin-12 in combination with rituximab in patients with B-cell non-Hodgkin lymphoma," *Blood*; 99:67-74.
Arakawa and Tsumoto (2003) "The effects of arginine on refolding of aggregated proteins: not facilitate refolding, but suppress aggregation," *Biochemical and Biophysical Research Communications*; 304:148-152.
Armstrong et al. (1996) "Interleukin 10 (IL-10) regulation of tumour necrosis factor cx (TNF-cx) from human alveolar macrophages and peripheral blood monocytes," *Thorax*; 51:143-149.
Asadullah et al. (1999) "Interleukin 10 Treatment of Psoriasis," *Arch Dermatol*.; 135-187-192.
Asadullah et al. (2003) "Interleukin 10 Therapy—Review of a New Approach," *Pharmacol. Rev.*; 55-241-269.
Bajetta et al. (1998) "Pilot Study of Subcutaneous Recombinant Human Interleukin 12 in Metastatic Melanoma," *Clinical Cancer Research*; 4:75-85.
Banerjee et al. (2012) "Poly(ethylene glycol)-Prodrug Conjugates: Concept, Design, and Applications," *Journal of Drug Delivery*; Article ID 103973:17 pages.
Bea at al. (2011) "Performance Evaluation of a Multiplex Assay for Future Use in Biomarker Discovery Efforts to Predict Body Composition," *Clin Chem Lab Med*.; 49(5):817-824.
Berger et al. (2009) "Safety and immunologic effects of IL-15 administration in nonhuman primates," *Blood*; 114:2417-2426.
Berman et al. (1996) "Systemic administration of cellular IL-10 induces an effective, specific, and long-lived immune response against established tumors in mice," *J Immunol*; 157:231-238.
Bilzer et al. (2006) "Role of Kupffer cells in host defense and liver disease," *Liver International*; 26:1175-1186.
Biswas et al. (2007) "Pathogen_specific CD8 T Cell Responses Are Directly Inhibited by IL-10," *J Immunol*.; 179:4520-4528.
Brady et al. (1994) "Reflections on a peptide," *Nature*; 368:692-693.
Brooks et al. (2008) "IL-10 and PD-L1 operate through distinct pathways to suppress T-cell activity during persistent viral infection," *PNAS*; 105(51):20428-20433.
Burgess (2009) "Refolding Solubilized Inclusion Body Proteins," *Methods in Enzymology*; 463:259-282.
Cai et al. (1999) "IL-10 enhances NK cell proliferation, cytotoxicity and production of IFN-q when combined with IL-18," *Eur. J. Immunol.*; 29:2658-2665.
Caliceti et al. (2012) "Effect of Plasma Membrane Cholesterol Depletion on Glucose Transport Regulation in Leukemia Cells," *PLoS One*; 7:e41246.
Cannistra & Niloff (1996) "Cancer of the uterine cervix," *New Eng I J Med* 334:1030-1038.
Cao et al. (2011) "Janus kinase activation by cytokine oncostatin M decreases PCSK9 expression in liver cells," *J Lipid Res.*; 52(3):513-530.

Capitini et al. (2009) "Modulating T cell Homeostasis with IL-7: Preclinical and Clinical Studies," *J Intern Med*; 266(2):141-153.
Cebon et al. (2003) "Two phase I studies of low dose recombinant human IL-12 with Melan-A and influenza peptides in subjects with advanced malignant melanoma," *Cancer Immunity*; 3:7 (18 pages).
Chamow et al. (1994) "Modification of CD4 Immunoadhesin with Monomethoxypoly(ethylene glycol) Aldehyde via Reductive Alkylation," *Bioconjugate Chem.*; 5:133-140.
Chan et al. (2015) "The Potentiation of IFN-γ and Induction of Cytotoxic Proteins by Pegylated IL-10 in Human CD8 T Cells," *J Interferon Cytokine* 35(12):948-955.
Chen & Zlotnik (1991) "IL-10: a novel cytotoxic T cell differentiation factor," *J Immunol*; 147:528-534.
Chen et al. (2007) "Prediction of linear B-cell epitopes using amino acid pair antigenicity scale," *Amino Acids*; 33:423-428.
Choi et al. (2006) "Serum adiponectin, interleukin-10 levels and inflammatory markers in the metabolic 1-18 syndrome," *Diabetes Research and Clinical Practice*; 75:235-240.
Collins et al. (2012) "Trastuzumab induces antibody-dependent cellmediated cytotoxicity (ADCC) in HER-2-non-amplified breast cancer cell lines," *Annals of Oncology*; 23:1788-1795.
Cindric, et al., (2007) "Structural 1-16 characterization of PEGylated rHuG-CSF and location of PEG attachment sites". Journal of Pharmaceutical and Biomedical Analysis. New York. NY. US, 44(2):388-395.
Compton et al. (2004) "Pathogenesis of Enterotropic Mouse Hepatitis Virus in Immunocompetent and Immunodeficient Mice," *Comparative Medicine*; 54(6):681-689.
Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology*; 33(1):74-82.
Couder et al. (1993) "Synthesis and biological activities of ψ(CH2NH) pseudopeptide analogues of the C-terminal hexapeptide of neurotensin," *Int. J. Peptide Protein Res.*; 41:181-184.
D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," *J. Exp. Med*; 178:1041-1048.
Das et al. (2012) "IL-10—Producing Regulatory B Cells in the Pathogenesis of Chronic Hepatitis B Virus Infection," *J. Immunol.*; 189(8):3925-3935.
Davidson & Diamond (2001) "Autoimmune diseases," *New Engl J Med*; 345:340-350.
De Waal Malefyt et al. (1991) "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med*; 174(4):915-924.
De Waal Malefyt et al. (1991) "Interleukin 10(IL-10) Inhibits Cytokine Synthesis by Human Monocytes: An Autoregulatory Role of IL-10 Produced by Monocytes," *J. Exp. Med*; 174:1209-1220.
Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.*; 288:10805-10818.
Dolgin (2011) "Trial puts niacin—and cholesterol dogma—in the line of fire," *Natue Medicine*; 17(7):356.
Dorner et al. (2011) "A genetically humanized mouse model for hepatitis C virus infection," *Nature*; 474:208-211.
Easy Surf. Blood Volume Calculator [online]Oct. 1, 2012 [retrieved Aug. 18, 2014]. Available on the internet: <URL: https://web.archive.org/web/20121001142649/http://www.easysurf.cc/cnver22.htm >.
Ehrlich et al. (2013) "Preparation and Characterization of Albumin Conjugates of a Truncated Peptide YY Analogue for Half-Life Extension," *Bioconjug. Chem.*; 24(12):2015-2024.
El-Manzalawy et al. (2008) "Predicting linear B-cell epitopes using string kernels," *J Mol Recognit*; 21:243-255.
Emmerich et al. (2012) "IL-10 directly activates and expands tumor-resident CD8(+) T cells without de novo infiltration from secondary lymphoid organs," *Cancer Res*; 72(14):3570-3581.

(56) References Cited

OTHER PUBLICATIONS

Engel et al. (2006) "Using Endoproteinases Asp-N and Glu-C to Improve Protein Characterization," *Promega Corporation*; 10th edition.
Enzinger & Mayer (2003) "Esophageal cancer," *New Eng I J Med*; 349:2241-2252.
Fahnert et al. (2012) "Using Folding Promoting Agents in Recombinant Protein Production: A Review," *Methods inn Molecular Biology*; 824:3-36.
Fang et al. (2015) "Programmed Death 1 (PD-1) is involved in the development of proliferative diabetic retinopathy by mediating activation-induced apoptosis," *Mol Vis*; 21:901-910.
Farrar et al. (1999) "Cancer dormancy. VII. A regulatory role for COB+ T cells and IFN-gamma in establishing and maintaining the tumor-dormant state," *J Imunol* 162:2842-2849.
Fehniger and Caligiuri (2001) "Interleukin 15: biology and relevance to human disease," *Blood*; 97:14-32.
Feingold et al. (1996) "Endotoxin, TNF, and IL-I decrease cholesterol 7a-hydroxylase mRNA levels and activity," *Journ of Lipid Res*; 37:223-228.
Fiorentino et al. (1989) "Two types of mouse T helper cell. IV. Th2 clones secrete a factor that inhibits cytokine production by Th1 clones," *J Exp Med*; 170:2081-2095.
Forastiere et al. (2001) "Head and neck cancer," *New Engl J Med* 345:1890-1900.
Fridman et al. (2012) "The immune contexture in human tumours: impact on clinical outcome," *Nature*; 12:298-306.
Fry and Mackall (2002) "Interleukin-7: from bench to clinic," *Blood*; 99:3892-3904.
Fujiwara et al. (2010) "Extraction and purification of human interleukin-10 from transgenic rice seeds," *Protein Expression and Purification*; 72:125-130.
Gargett et al.: 11 Different cytokine and stimul ation conditions influence t he expansion and immune phenotype of third-generat ion chimeric antigen receptor T cells specific for tumor antigen GD2, Cytotherapy, vol. 17 , No. 4, Apr. 1, 2015 (Apr. 2015) , pp. 487-495.
Galon et al. (2013) "The Continuum of Cancer Immunosurveillance: Prognostic, Predictive, and Mechanistic Signatures," *Immunity*; 39:11-26.
Gameren et al. (1994) "Effects of Recombinant human interleukin-6 in cancer patients: a phase I-II study," *Blood*; 84:1434-1441.
Gao et al. (2012) "Best: Improved Prediction of B-Cell Epitopes from Antigen Sequences," *PLoS One*; 7(6): e40104.
GenBank Accession No. M37897 "Mouse interleukin 10 mRNA, complete cds," dated Apr. 27, 1993.
GenBank Accession No. NP 000563 "Interleukin-10 precursor [*Homo sapiens*]," dated Mar. 3, 1995.
Georgescu et al. (1997) "Interleukin-10 Promotes Activation-induced Cell Death of SLE Lymphocytes Mediated by Fas Ligand," *J. Clin. Invest.*; 100:2622-2633.
Gerstein et al. (2008) "Effects of Intensive Glucose Lowering in Type 2 Diabetes," *New England J of Medicine*; 358(24):2545-2559.
Gesser et al. (1997) "Identification of functional domains on human interleukin 10," *Proc. Natl. Acad. Sci.*; 94:14620-14625.
Gierens et al. (2000) "Interleukin-6 Stimulates LDL Receptor Gene Expression via Activation of Sterol-Responsive and Sp1 Binding Elements," *Arterioscler Thromb Vasc Biol.*; 20:1777-1783.
Gill et al., (2015) "Going viral: Chimeric antigen receptor T-cell therapy for hematological malignancies", Immunological Reviews 28150181 Blackwell Publishing Ltd GBR, vol. 263 , No. 1, pp. 68-89.
Gregoriadis et al., (2005) "Improving the therapeutic efficacy of peptides and proteins: A role for polysialic acids," *Int. J. Pharmaceutics*; 300(1-2):125-130.
Groux et al. (1998) "A transgenic model to analyze the immunoregulatory role of IL-10 secreted by antigen-presenting cells," *J Immunol*; 162:1723-1729.
Groux et al. (1998) "Inhibitory and stimulatory effects of IL-10 on human COB+ T cells," *J Immunol*; 160:3188-3193.
Hagenbaugh et al. (1997) "Altered immune responses in interleukin 10 transgenic mice," *J Exp Med*; 185:2101-2110.
Hamada et al. (2009) "Effect of Additives on Protein Aggregation," *Current Pharm Biotech*; 10:400-407.
Hashizume et al. (2010) "Overproduced interleukin 6 decreases blood lipid levels via upregulation of very-low-density lipoprotein receptor," *Ann Rheum Dis*; 69:741-746.
Heeschen et al. (2003) "Serum Level of the Antiinflammatory Cytokine Interleukin-1 0 Is an Important Prognostic Determinant in Patients With Acute Coronary Syndromes," *Circulation*; 107:2109-2114.
Hombach et al. (2013) "Arming Cytokine-induced Killer Cells With Chimeric Antigen Receptors: CD28 Outperforms Combined CD28-OX40 'Super-stimulation'," *Molecular Therapy*; 12:2268-2277.
Howard et al. (1993) "Interleukin 10 Protects Mice from Lethal Endotoxemia," *J. Exp. Med.*; 177:1205-1208.
Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research*; 2(12):1969-1979.
Huang et al. (2010) "Depletion of Liver Kupffer Cells Prevents the Development of Diet-Induced Hepatic Steatosis and Insulin Resistance," 59:347-357.
Huntington et al. (2008) "IL-15 trans-presentation promotes human NK cell development and differentiation in vivo," *J. Exp. Med.*; 206:25-34.
Hustoft et al. (2012) "A Critical Review of Trypsin Digestion for LC-MS Based Proteomics," *InTech*; Chapter 4.
Infante et al. (2015) "A first-in-human dose escalation study of PEGylated recombinant human IL-10 (AM0010) in advanced solid tumors," *ASCO Meeting Abstracts*; 33(15 suppl):3017.
International Search Report; PCT/US01/42431, dated Aug. 20, 2002.
Ishikawa et al. (2005) "Interleukin-10 plasmid DNA inhibits liver and lung metastasis of Colon 26 adenocarcinoma in mice," *Proceedings of the Annual Meeting, American Association for Cancer Research*; vol. 46, Abstract # 3364.
Izbicki et al. (1997) "Prognostic value of immunohistochemically identifiable tumor cells in lymph nodes of patients with completely resected esophageal cancer," *New Engl J Med*; 337:1188-1194.
Jameson et al. (1994) "A rationally designed CD4 analogue inhibits experimental allergic encephalomyelitis," *Nature*; 368:744-746.
Jevševar et al. (2010) "PEGylation of therapeutic proteins," *Biotechnol. J.*; 5:113-128.
Jiang et al. (2015) "T-cell exhaustion in the tumor microenvironment," *Cell Death Dis*; 6:e1792.
Josephson et al. (2001) "Crystal Structure of the IL-10/IL-10R1 Complex Reveals a Shared Receptor Binding Site," *Immunity*; 14:35-46.
Jungbauer et al. (2007) "Current status of Technical protein refolding," *Journal of Biotechnology*; 128:587-596.
Katre (1993) "The Conjugation of Proteins with Polyethylene Glycol and Other Polymers Altering Properties of Proteins to Enhance their Therapeutic Potential," *Advanced Drug Delivery Reviews*; 10(1):91-114.
Khow and Suntrarachun (2012) "Strategies for production of active eukaryotic proteins in bacterial expression system," *Asian Pac. J. Biomed.*; 2(2):159-162.
Kimball et al (2002) "Clinical and Immunologic Assessment of Patients With Psoriasis in a Randomized, Double-blind, Placebo-Controlled Trial Using Recombinant Human Interleukin 10," *Arch Dermatol*; 138:1341-1346.
Kinstler et al. (1996) "Characterization and Stability of N-terminally PEGylated rhG-CSF," *Pharm. Res.*; 13:996-1002.
Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification*; 62:199-205.
Kokura et al. (2003) "The blocking of NFκB activation by systemicinterleukin-10 gene therapy inhibits liver and lung metastasis of colon 26 adenocarcinoma in mice" *Gastroenterology*; 124(4): Abstract No. W965.

(56) References Cited

OTHER PUBLICATIONS

Kokura et al. (2005) "Interleukin-1 0 plasmid DNA inhibits subcutaneous tumor growth of Colon adenocarcinoma in mice," *Cancer Letters*; 218:171-179.
Kong et al. (2005) "In vivo activities of cytokine oncostatin M in the regulation of plasma lipid levels," *Journal of Lipid Research*; 46:1163-1171.
Körholz et al. (1997) "The Role of Interleukin-10 (IL-10) in IL-15—Mediated T-Cell Responses," *Blood*; 90(11):4513-4521.
Kundu et al. (1996) "Antimetastatic and antitumor activities of interleukin 10 in a murine model of breast cancer," *J Nail Cancer Inst*; 88:536-541.
Kundu et al. (1997) "Interleukin-10 inhibits tumor metastasis, down regulates MHC class I, enhances NK lysis," *Cellular Immunology*, Academic Press; 180(1):55-61.
Kute et al. (2012) "Understanding key assay parameters that affect measurements of trastuzumab-mediated ADCC against Her2 positive breast cancer cells," *OncoImmunology*; 1(6):810-821.
Langowski et al. (2006) "IL-23 promotes tumour incidence and growth," *Nature*; 442:461-465.
Lasek et al. (2014) "Interleukin 12: still a promising candidate for tumor immunotherapy?" *Cancer Immunol Immunother*; 63:419-435.
Le et al. (2001) "Pre-existing tumor-sensitized T cells are essential for eradication of established tumors by IL-12 and cyclophosphamide plus IL-12," *J Immunol*; 167:6765-6772.
Lehmann et al. (2014) "IL-12 Directs Further Maturation of Ex Vivo Differentiated NK Cells with Improved Therapeutic Potential," *PLoS One*; 9(1):e87131 (12 pages).
Lewington and Clark (2005) "Combined Effects of Systolic Blood Pressure and Total Cholesterol on Cardiovascular Disease Risk," *Circulation*; 112:3373-3374.
Lindhout et al. (2011) "Site-specific enzymatic polysialylation of therapeutic proteins using bacterial enzymes," *PNAS*; 108(18)7397-7402.
Liu et al. (2003) "IL-10 Mediates Suppression of the CD8 T Cell IFN-γ Response to a Novel Viral Epitope in a Primed Host," *J Immunol*; 171:4765-4772.
Loebbermann et al. (2012) "IL-10 Regulates Viral Lung Immunopathology during Acute Respiratory Syncytial Virus Infection in Mice," *PLoS One*; 7(2):e32371.
Lopez et al. (2005) "IL-12 and IL-10 Expression Synergize to Induce the Immune-Mediated Eradication of Established Colon and Mammary Tumors and Lung Metastasis," *J Immunol*; 175:5885-5894.
Lowe et al. (1998) "Impact of Major Cardiovascular Disease Risk Factors, Particularly in Combination, on 22-Year Mortality in Women and Men," *Arch Intern Med*; 158:2007-2014.
Lu et al. (2004) "Prognostic factors in resected stage I non-small-cell lung cancer: a multivariate analysis of six molecular markers," *J Clin Oneal*; 22:4575-4583.
Lugli et al. (2010) "Transient and persistent effects of IL-15 on lymphocyte homeostasis in nonhuman primates," *Blood*; 116:3238-3248.
Lynch and Chapelle (2003) "Hereditary colorectal cancer," *New Eng I J Med*; 348:919-932.
Martin et al. (2001) "B-Cell Deficiency Suppresses Vaccine-Induced Protection against Murine Filariasis but Does Not Increase the Recovery Rate for Primary Infection," *Infect. Immun.*; 69(11):7067-7073.
Mattos et al. (2012) "PEGylation of interleukin-10 improves the pharmacokinetic profile and enhances the antifibrotic effectivity in CCl.-induced fibrogenesis in mice," *J Control Release*; 162(1):84-91.
Maus et al. (2014) "Antibody-modified T cells: CARs take the front seat for hematologic malignancies," *Blood*; 123(17):2625-2635.
Miki Toyokazu et al. (2000) "Anti-metastatic effect of IL-10 gene modification in human lung cancer cells is differentially regulated by organ microenvironments," *Proceedings of the Annual Meeting American Association for Cancer Research*; 41:3.

Monk (2011) "A Strategy for the Quantification of Protein Polyethylene Glycol (PEG) Derivatized Sites using iTRAQ," *University of California, San Diego*; 1-51.
Moore et al. (1990) "Homology of cytokine synthesis inhibitory factor (IL-10) to the Epstein-Barr virus gene BCRFI," *Science*; 248:1230-1234.
Moran et al. (1994) "Human leukemia inhibitory factor inhibits development of experimental atherosclerosis," *Arterioscler Thromb Vasc Biol.*; 14(8):1356-1363.
Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research*; 21:257-263.
Muecke, Susanne, et al., (2000) "Suppression of the Tumorigenic Growth of Burkitt's Lymphoma Cells in Immunodeficient Mice by Cytokine Gene Transfer Using EBV-Derived Episomal Expression Vectors", Int. J. Cancer, 86:301-306.
Mumm et al. (2011) "IL-10 elicits IFNγ-dependent tumor immune surveillance," *Cancer Cell*; 20(6):781-796.
Mumm, John B., et al., (2012) "Killing from within" OncoImmunology, 1(9):1598-1600.
Naicker et al. (2009) "Interleukin-10 Promoter Polymorphisms Influence HIV-1 Susceptibility and Primary HIV-1 Pathogenesis," *J. Infect. Dis.*; 200(3):448-452.
Natsume et al. (2009) "Improving effector functions of antibodies for cancer treatment: Enhancing ADCC and CDC," *Drug Design, Development and Therapy*; 3:7-16.
Nenseter et al. (1992) "Role of liver endothelial and Kupffer cells in clearing low density lipoprotein from blood in hypercholesterolemic rabbits," *J of Lipid Res*; 33:867-877.
Neven et al. (2013) "A Mendelian predisposition to B cell lymphoma caused by IL-10R deficiency," *Blood*; 122(23):3712-3722.
Neyrinck et al. (2009) "Critical role of Kupffer cells in the management of diet-induced diabetes and obesity," *Biochemical and Biophysical Research Communications*; 385:351-356.
Nicholls et al. (2012) "Is niacin ineffective? Or did Aim-High miss its target?," *Cleveland Clinic Journ of Med*; 79(1):38-43.
Noguchi et al. (2003) "PDX-1 Protein Containing Its Own Antennapedia-Like Protein Transduction Domain Can Transduce Pancreatic Duct and Islet Cells," *Diabetes*; 52(7):1732-1737.
Osaki et al. (1999) "Potent antitumor effects mediated by local expression of the mature form of the interferon-γ inducing factor, interleukin-18 (IL-18)," *Gene Therapy*; 6:808-815.
Osborne (1998) "Tamoxifen in the treatment of breast cancer," *New Engl J Med*; 339:1609-1618.
Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of*.
Pardoll (2012) "The blockade of immune checkpoints in cancer immunotherapy," *Cancer*; 12:252-264.
Park et al. (2011) "IL-15-Induced IL-10 Increases the Cytolytic Activity of Human Natural Killer Cells," *Mol. Cells*; 32:265-272.
Pasut and Veronese (2012) "State of the art in PEGylation: The great versatility achieved after forty years of research," *Journal of Controlled Release*; 161:461-472.
Payne et al. (2010) "Product development issues for PEGylated proteins," *Pharmaceutical Development and Technology*; 16:423-440.
Pegram et al. (2012) "Interleukin 12: Stumbling Blocks and Stepping Stones to Effective Anti-Tumor Therapy," *Advancements in Tumor Immunotherapy and Cancer Vaccines*; Chapter 10:197-218.
Pellegrini et al. (2011) "IL-7 Engages Multiple Mechanisms to Overcome Chronic Viral Infection and Limit Organ Pathology," *Cell*; 144:1-13.
Pettit et al. (1997) "Structure-Function Studies of Interleukin 15 using Site-specific Mutagenesis, Polyethylene Glycol Conjugation, and Homology Modeling," *J. Biol. Chem.* 272:2312-2318.
Rachmawati et al. (2004) "Pharmacokinetic and Biodistribution Profile of Recombinant Human Interleukin-10 Following Intravenous Administration in Rats with Extensive Liver Fibrosis," *Pharm. Res.*; 21(11):2072-2078.

(56) References Cited

OTHER PUBLICATIONS

Rachmawati et al. (2007) "Chemical Modification of Interleukin-10 with Mannose 6-Phosphate Groups Yields a Liver-Selective Cytokine," *Drug Metabolism and Disposition*; 35(5):814-821.

Radwanski et al. (1998) "Pharmacokinetics and Leukocyte Responses of Recombinant Human Interleukin-10," *Pharm. Res.*; 15(12):1895-1901.

Ramirez-Montagut et al. (2003) "Immunity to melanoma: unraveling the relation of tumor immunity and autoimmunity," *Oncogene*; 22:3180-3187.

Re et al. (2002) "Preclinical evaluation of the antiproliferative potential of STI571 in Hodgkin's disease," *British Journal of Cancer*, 86:1333-1335.

Reynolds, et al. (2002) "Proteolytic 18O Labeling for Comparative Proteomics: Evaluation of Endoprotease Glu-C as the Catalytic Agent," *Journal of Proteome Research*; 1(1):27-33.

Roberts et al. (2012) "Chemistry for peptide and protein PEGylation," *Advanced Drug Delivery Reviews*; 64:116-127.

Rolfe et al. (2003) "Leukaemia inhibitory factor retards the progression of atherosclerosis," *Cardiovascular Research*; 58:222-230.

Russo et al. (2006) "Randomized trial of pegylated interferon a-2b monotherapy in haemodialysis patients with chronic hepatitis C," *Nephrol Dial Transplant*; 21:437-443.

Saha and Raghava (2006) "Prediction of continuous B-cell epitopes in an antigen using recurrent neural network," *Proteins*; 65:40-48.

Sakamoto et al. (2003) "Interleukin-10 gene therapy enhances antitumor effect of CPT-11 for lung metastasis of colon26 adenocarcinoma in mice," *Gastroenterology*; 124(4):A456-A457.

Sawaya et al. (2003) "Risk of cervical cancer associated with extending the interval between cervical-cancer screenings," *New Engl J Med*; 349:1501-1509.

Schäffner et al. (2001) "Cosecretion of Chaperones and Low-Molecular-Size Medium Additives Increases the Yield of Recombinant Disulfide-Bridged Proteins," *Applied and Environmental Microbiology*; 67(9):3994-4000.

Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.

Shen et al. (2013) "Proprotein convertase subtilisin/kexin type 9 potentially influences cholesterol uptake in macrophages and reverse cholesterol transport," *FEBS Letters*; 587:1271-1274.

Smith et al. (1996) "Administration of interleukin-1 0 at the time of priming protects Corynesmitbacterium parvum-primed mice against LPS- and TNF-alpha-induced lethality," *Cellular Immunology* 173(2):207-214.

Sneller et al. (2011) "IL-15 administered by continuous infusion to rhesus macaques induces massive expansion of CD8 T effector memory population in peripheral blood," *Blood*; 118(26):6845-6848.

Soman et al. (2009) "MTS dye based colorimetric CTLL-2 cell proliferation assay for product release and stability monitoring of Interleukin-15: Assay qualification, standardization and statistical analysis," *J Immunol Methods*; 348(1-2):83-94.

Song et al. (2012) "CD27 costimulation augments the survival and antitumor activity of redirected human T cells in vivo," *Blood*; 119(3):696-706.

Srivastava et al. (2013) "Effects of interleukin-18 on natural killer cells: costimulation of activation through Fc receptors for immunoglobulin," *Cancer Immunol Immunother*; 62(6):1073-1082.

Steel, JC et al., (2012) "Biology and its Therapeutic Implications in Cancer", Trends in Pharmacological Sciences, 33(1):35-41.

Storici and Resnick (2006) "The delitto perfetto approach to in vivo site-directed mutagenesis and chromosome rearrangements with synthetic oligonucleotides in yeast," *Methods in Enzymology*; 409:329-345.

Sweredoski and Baldi (2009) "COBEpro: a novel system for predicting continuous B-cell epitopes," *Protein Eng Des Sel*; 22:113-120.

Syto et al. (1998) "Structural and biological stability of the human interleukin 10 homodimer," *Biochemistry*; 37(48):16943-16951.

Teng et al. (2015) "IL-12 and IL-23 cytokines: from discovery to targeted therapies for immune-mediated inflammatory diseases," *Nature Medicine*; 21:719-729.

Teng et al.: "Stable IL-10: A new therapeutic that promotes tumor immunity"Cancer Cell 2011 Cell Press USA, vol. 20, No. 6 , Dec. 13, 2011 (Dec. 13, 2011) , pp. 691-693.

Tilg et al. (2002) "Treatment of Crohn's disease with recombinant human interleukin 10 induces the proinflammatory cytokine interferon γ" *Gut*; 50:191-195.

Trandem et al. (2011) "Virally Expressed Interleukin-10 Ameliorates Acute Encephalomyelitis and Chronic Demyelination in Coronavirus-Infected Mice," *J. Virol.*; 85(14):6822-6831.

Tréhin et al. (2004) "Cellular uptake but low permeation of human calcitonin-derived cell penetrating peptides and Tat(47-57) through well-differentiated epithelial models," *Pharm. Research*; 21:1248-1256.

Tsumoto et al. (2003) "Practical considerations in refolding proteins from inclusion bodies," *Protein Expression and Purification*; 28:1-8.

Tsumoto et al. (2004) "Role of Arginine in Protein Refolding, Solubilization, and Purification," *Biotechnol. Prog.*; 20:1301-1308.

Valabrega et al. (2007) "Trastuzumab: mechanism of action, resistance and future perspectives in HER2-overexpressing breast cancer," *Annals of Oncology*; 18:977-984.

Van Deventer et al. (1997) "Multiple Doses of Intravenous Interleukin 10 in Steroid-Refractory Crohn's Disease," *Gastroenterology*, 113:383-389.

Vicari and Trinchieri (2004) "Interleukin-10 in viral diseases and cancer: exiting the labyrinth?," *Immunological Reviews*; 202:223-236.

Vigneron et al. (2013) "Database of T cell-defined human tumor antigens: the 2013 update," *Cancer Immunity*; 13:15-20.

Virgin, et al. (2009) "Redefining Chronic Viral Infection," *Cell*; 138:30-50.

Von Andrian and Mackay (2000) "T-cell function and migration. Two sides of the same coin," *New Engl J Med*; 343:1020-1034.

Waldmann et al. (2011) "Safety (toxicity), pharmacokinetics, immunogenicity, and impact on elements of the normal immune system of recombinant human IL-15 in rhesus macaques," *Blood*; 117:4787-4795.

Walter and Nagabhushan (1995) "Crystal structure of interleukin 10 reveals an interferon gamma-like fold," *Biochemistry*; (38):12118-12125.

Wee et al. (2010) "SVM-based prediction of linear B-cell epitopes using Bayes Feature Extraction," *BMC Genomics*; 11(Supp 4):S21.

Wender et al. (2000) "The design, synthesis, and evaluation of molecules that enable or enhance cellular uptake: peptoid molecular transporters," *Proc. Natl. Acad. Sci. USA*; 97:13003-13008.

Wilson et al. (2011) "The role of IL-10 in regulating immunity to persistent viral infections," *Curr Top Microbiol Immunol.*; 350: 39-65.

Witsch et al. (2010) "Roles for Growth Facotes in Cancer Progression," *Physiology*; 25(2):85-101.

Wu et al. (2012) "Immunotherapies: The Blockade of Inhibitory Signals," *Int. J. Biol. Sci.*; 8:1420-1430.

Xu et al. (2010) "Regulation of Antitumor Immune Responses by the IL-12 Family Cytokines, IL-12, IL-23, and IL-27," *Clinical and Developmental Immunology*; Article ID:832454 (9 pages).

Yamaguchi and Miyazaki (2014) "Refolding Techniques for Recovering Biologically Active Recombinant Proteins from Inclusion Bodies," *Biomolecules*; 4:235-251.

Yoshioka et al. (2011) "Development of a novel DDS for site-specific PEGylated proteins," *Chem. Central J.*; 5:25.

Younes et al. (2004) "Phase II Clinical Trial of Interleukin-12 in Patients with Relapsed and Refractory Non-Hodgkin's Lymphoma and Hodgkin's Disease," *Clinical Cancer Research*; 10:5432-5438.

Zauner et al. (1996) "Glycerol Enhancement of Ligand-Polylysine/ DNA Transfection," *Bio Techniques*; 20:905-913.

(56) References Cited

OTHER PUBLICATIONS

Zdanov et al. (1995) "Crystal structure of interleukin-10 reveals the functional dimer with an unexpected topological similarity to interferon γ," *Structure*; 3:591-601.
Zdanov et al. (1996) "Crystal structure of human interleukin-10 at 1.6 A resolution and a model of a complex with its soluble receptor," *Protein Sci.*; (10):1955-1962.
Zender et al. (2002) "VP22-mediated intercellular transport of p53 in hepatoma cells in vitro and in vivo," *Cancer Gene Ther.*; 9(6):489-496.
Zheng et al. (1996) "Interleukin-10 inhibits tumor metastasis through an NK cell-dependent mechanism," *J Exp Med*; 184:579-584.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Dec. 11, 2013, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 31, 2014, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jul. 17, 2014, 6 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Mar. 24, 2015, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 12, 2016, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Oct. 2, 2016, 7 pages.
NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine Containing Regimen", ClinicalTrials.gov, Oct. 4, 2016, 3 pages.
Bowie, James, U., et al. (1990) "Deciphering the Message in Protein Sequences: Tolerance to Amino Acid Substitutions", Science, 247:1306-1310.
Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Bioi., 111:2129-2138.
Bork, Peer, (2000) "Powers and Pitfalls in Sequence Analysis: The 70% Hurdle", Genome Research, 10:398-400.
Lazar, Eliane, et al.(1988) "Transforming Growth Factor alpha: Mutation of Aspartic Acid 47 and Leucine 48 Results in Different Biological Activities", Mol. Cell. Bioi., 8:1247-1252.
UniProt reference P79338 (1L 1 O_MACFA) (downloaded from http://www.uniprot.org/uniprot/P79338, last sequence update May 1, 1997).
UniProt reference A2T6Z6 (1L 1 O_PANTR) (downloaded from http://www.uniprot.org/uniprot!A2T6Z6, last sequence update Mar. 6, 2007).
Soderquist, et al. (2010) "PEGylation of interleukin-1 0 for the mitigation of enhanced pain states", J Biomed Mater Res A, 3(93):1169-1179.
Gabriel, A., (2007) "Changes in plasma cholesterol in mood disorder patients: Does treatment make a difference?", Journal of Affective Disorders, 99:273-278.
Papadopoulou, Athanassia, et al., (2013) "Plasma total cholesterol in psychiatric patients after a suicide attempt and in follow-up", Journal of Affective Disorders, 148:440-443.
Virkkunen, M., (1979) "Serum Cholesterol in Antisocial Personality", Neuropsychobiology, 5:27-30.
Pjrek, Edda, et al., (2007) "Serum lipid levels in seasonal affective disorder", Eur Arch Psychiatry Clin Neurosci, 257:197-202.
Aukrust et al., (2005) "Potential role for immunomodulatory therapy in atherosclerotic plaque stabilization", Expert Opinion Pharmacother, 6:2169-2180.
Cheon, H.G. (2013) "Latest research and development trends in non insulin anti-diabetics", Arch. Pharm. Res., 36:145-153.
Fichtlscherer et al., (2004) "Interleukin-10 serum levels and systemic endothelial vasoreactivity in patients with coronary artery desease", J. Am. Coll. Cardiol., 44:44-49.
Dinant, et al., (2007) "IL-10 attenuates hepatic I/R injury and promotes hepatocyte proliferation", J. Surg. Res., 141:176-182.
Gotoh, et al., (2012) "A novel anti-inflammatory role for spleen-derived Interleukin-10 in obesity-induced inflammation in white adipose tissue and liver", Diabetes, 61:1994-2003.
Kumagai, et al., (2013) "Effects of Ezetimibe on hypercholesterolemia in the lipid profile in patients with metabolic syndrome", IJC Metabolic and Endocrine, 1:7-12.
NCT01025297, (2012) "'Dose Escalation Study of Interleukin7(IL7) and Bitherapy in HCV Genotype 1 or 4 Patients Resistant to Bitherapy Alone (Eclipse 2)'", Clinical Trials, 6 pages.
Fry and Mackall (2005) "'The Many Faces of IL-7: From Lymphopoiesis toPeripheral T Cell Maintenance'", the Journal of Immunology, 174:6571-6576.
Alpdogan, et al., (2005) "IL-7 and IL-15: therapeutic cytokines for immunodeficiency", Cell, 26(1):56-64.
Stoklasek, et al., (2006) "Combined IL-15/IL-15Rα Immunotherapy Maximizes IL-15 Activity in Vivo", J Immunol, 177 (9):6072-6080.
Storek, et al., (2003) "'Interleukin-7 improves CD4 T-cell reconstitution after autologous CD34 celltransplantation in monkeys'", Blood, 101(10):4209-4218.
Wylie, Davic, C., et al.; (2001) "Carboxyalkylated Histidine Is a pH-Dependent Product of Pegylation with SC-PEG", Pharmaceutical Research, 18(9):2-8.
PeproTech, "Recombinant Human IL-10 (carrier-free)", (2017) 7 pages.
BioLegend, "Recombinant Human IL-10 (carrier-free)", (2007) 3 pages.
Anstee and Goldin, (2006) "Mouse models in non-alcoholic fatty liver disease and steatohepatitis research", Int. J. Exp. Path., 87:1-16.
Cosma, Meda, (2014) :The impact of cytokines and chemokines on non-alcoholic fatty liver disease (NAFLD), Biotechnology, Molecular Biology and Nanomedicine, 2(1):15-16.
Gotoh, Koro, et al., (2017) "Role of spleen-derived IL-10 in prevention of systemic low-grade inflammation by obesity", Endocnne Journal, 64(4):375-378.
Gotoh, Koro, (2012) "Spleen-Derived Interleukin-10 Downregulates the Severity of High-Fat Diet-Induced Non-Alcoholic Fatty Pancreas Disease", PLOS, 12 pages.
Larter and Yeh, (2008) "Animal models of NASH: Getting both pathology and metabolic context right", Journal of Gastroenterology and Hepatology, 23:1635-1648.
Lauw, Fanny, et al., (2000) "Proinflammatory Effects of IL-10 During Human Endotoxemia", J Immunol, 165:2783-2789.
Millic, Sandra, et al., (2014) "Non-alcoholic fatty liver disease and obesity: Biochemical, metabolic and clinical presentations", World J Gastroenterol, 20(28):9330-9337.
Neyrinck, Audrey, et al., (2002) "Inhibition of Kupffer cell activity induces hepatic triglyceride synthesis in fasted rats, independent of lipopolysaccharide challenge", Journal of Hepatology, 36:466-473.
Rachmawati, Heni, et al., (2004) "Pharmacokinetic and Biodistribution Profile of Recombinant Human Interleukin-10 Following Intravenous Administration in Rats with Extensive Liver Fibrosis", Pharmaceutical Research, 21(11):2072-2073.

(56) References Cited

OTHER PUBLICATIONS

Wan, Jinghong, et al., (2014) "M2 Kupffer Cells Promote M1 Kupffer Cell Apoptosis: A Protective Mechanism Against Alcoholic and Nonalcoholic Fatty Liver Disease", Hepatology, 59(1):131-142.

Liang, et al., (2014) "Establishment of a General NAFLD Scoring System for Rodent Models and Comparison to Human Liver Pathology", PLOSone, 17 pages.

Spoto, et al., (2013) "Spleen IL-10, A Key Player in Obesity-Driven Renal Risk", Nephrol Dial Transplant, 28:1061-1064.

Liedtke, et al., (2013) "Experimental liver fibrosis research: update on animal models, legal issues and translational aspects", Fibrogenesis Tissue Repair, 6(19):1-25.

Paulsen and Reichelt, (1992) "Mouse liver regeneration after carbon tetrachloride injury as test system for hepatic growth regulators" Virchows Archiv B Cell Pathol, 62:173-177.

Bieghs, et al., (2012) "LDL Receptor Knock-Out Mice Are a Physiological Model Particularly Vulnerable to Study the Onset of Inflammation in Non-Alcoholic Fatty Liver Disease", PLoS One, 7(1):1-11.

Scotton and Chambers, (2010) "Bleomycin revisited: towards a more representative model of IPF?", Am J Physiol Lung Cell Mol Physiol, 299:L439-L441.

Tilg, et al., "Induction of circulating interleukin 10 by interleukin 1 and interleukin 2, but not interleukin 6 immunotherapy," *Cytokine*, vol. 7, No. 7, pp. 734-739 (1995).

Naing, et al, "Safety, Antitumor Activity, and Immune Activation of Pegylated Recombinant Human Interleukin-10 in Patients with Advanced Solid Tumors," *Journal of Clinical Oncology*, vol. 34, No. 29, pp. 3562-3569 (2016).

\* cited by examiner

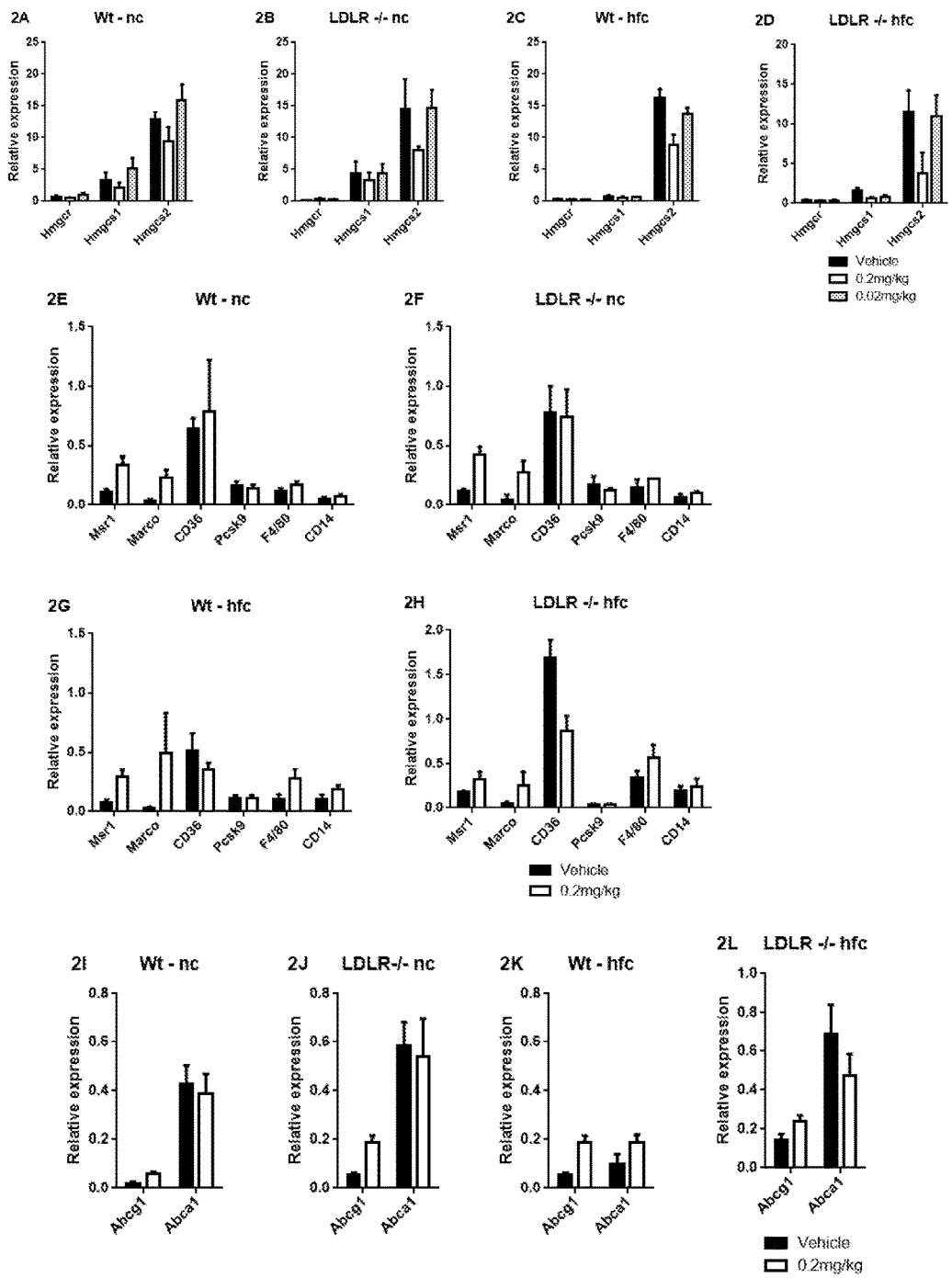

METHODS OF LOWERING SERUM CHOLESTEROL

CROSS-REFERENCE TO RELATED APPLICATION

This application claims priority benefit of U.S. provisional application Ser. No. 62/006,651, filed Jun. 2, 2014, which application is incorporated herein in its entirety.

FIELD OF THE INVENTION

This invention relates to methods of treating or preventing hypercholesterolemia, and a diverse array of related diseases, disorders and conditions, by administering agents that modulate lipoprotein homeostasis.

INTRODUCTION

Hypercholesterolemia, the presence of high levels of cholesterol in the blood, is a common form of hyperlipidemia and hyperlipoproteinemia. Cholesterol is transported in the blood plasma within lipoproteins, which are classified by their density: VLDL (very low density lipoprotein), IDL (intermediate density lipoprotein), LDL (low density lipoprotein), and HDL (high density lipoprotein). Elevated levels of VLDL, IDL and LDL—LDL in particular—are associated with an increased risk of cardiovascular disorders, including atherosclerosis and heart disease. Conversely, higher levels of HDL are thought to exert a protective effect. In subjects with hypercholesterolemia uncontrolled by dietary restrictions, pharmacological intervention is frequently warranted.

Increased activity of the innate immune system has been linked to the pathogenesis of the dyslipidemia and insulin resistance associated with obesity and type II diabetes. Macrophages, myeloid-derived mononuclear cells, play a key role in the innate immune system. They are recruited to tissues in response to infection, tissue damage, or other trauma, and are particularly enriched in tissues that are frequently exposed to exogenous and endogenous toxins, such as the liver. Recent studies indicate that macrophages are involved in diet-induced alterations in hepatic liver metabolism and insulin sensitivity and suggest that they play a role in type II diabetes and obesity (Huang et al., Diabetes 59:347-57 (2010). Thus, modulation of hepatic macrophage homeostasis may provide another approach for the treatment and prevention of metabolic abnormalities.

Although conventional lipid-lowering agents, which generally exert their activity by reducing cholesterol production or absorption, are effective in treating most patient populations, alternative agents, especially agents acting through different mechanism(s) of action, would provide a valuable therapeutic option, both as monotherapy and as an addition to an existing pharmacological regimen.

SUMMARY

The present disclosure contemplates methods of using IL-10, modified (e.g., pegylated) IL-10, and associated agents described herein, and compositions thereof, to treat and/or prevent various diseases, disorders and conditions, and/or the symptoms thereof. Particular embodiments are directed to the treatment and/or prevention of abnormally high levels of cholesterol and/or manifestation(s) of hypercholesterolemia in as subject. Further particular embodiments are directed to the modulation of Kupffer cells (e.g., through increased activity and/or increased numbers) to effect the treatment and/or prevention of abnormally high levels of cholesterol and/or manifestation(s) of hypercholesterolemia in as subject.

Hypercholesterolemia itself is generally asymptomatic. However, chronic elevation of serum cholesterol contributes to formation of atheromatous plaques in the arteries. Relatively small plaques may rupture and cause a clot to form and obstruct blood flow. By comparison, larger plaques can result in arterial stenosis or occlusion of the involved arteries. A sudden occlusion of a coronary artery results in a myocardial infarction, whereas an occlusion of an artery supplying the brain can result in a stroke.

Gradual development of the stenosis or occlusion that causes a progressive reduction in the blood supply to the tissues and organs frequently results in impairment of the activity thereof. Tissue ischemia may manifest as one or more symptoms. For example, temporary ischemia of the brain (a transient ischemic attack) may manifest as temporary loss of vision, dizziness, or impairment of balance, aphasia, paresis and paresthesia. Insufficient blood supply to the heart may manifest as chest pain; ischemia of the eye may manifest as transient visual loss in one eye; and insufficient blood supply to the legs may manifest as calf pain.

Hypercholesterolemia may be categorized into various types with characteristic manifestations. For example, Type IIa hyperlipoproteinemia may be associated with xanthelasma palebarum (yellowish patches underneath the skin around the eyelids), arcus senilis (white or gray discoloration of the peripheral cornea), and xanthomata (deposition of yellowish cholesterol-rich material) of the tendons (usually the fingers). In contrast, Type III hyperlipidemia may be associated with xanthomata of the palms, knees and elbows.

According to the lipid hypothesis, abnormal cholesterol levels (generally higher concentrations of LDL particles and lower concentrations of functional HDL particles) in the blood are strongly associated with cardiovascular disease due to promotion of atheroma development in arteries (atherosclerosis). As high circulating LDL concentrations have been linked to atheroma formation, LDL is often referred to as "bad cholesterol"; in contrast, high concentrations of HDL can remove cholesterol from cells, diminishing atheroma formation, and thus HDL is often referred to as "good cholesterol". However, recent evidence suggests that total cholesterol is the most relevant indicator of cardiovascular abnormalities.

Heretofore, the therapeutic control of systemic cholesterol levels has focused primarily on inhibition of the uptake of dietary cholesterol and on inhibition of endogenous hepatocellular cholesterol synthesis. By way of example, ezetimibe (ZETIA) inhibits dietary uptake in the small intestine, and it has been shown to dramatically decrease serum cholesterol in both genetically deficient mice strains APOE-/- and LDLR-/- mice fed a high fat diet (Davis, H. R., Jr., et al., Arterioscler Thromb Vasc Biol, 2001. 21(12):2032-38). By way of further example, the statin class of cholesterol-lowering therapeutic agents act through the Mevalonate pathway, which is primarily active in hepatocytes, by inhibition of HMG-CoA-mediated cholesterol synthesis.

Therapeutic modalities for the treatment of hypercholesterolemia that act through other mechanisms of action have been developed or are in late-stage development. These modalities include inhibitors of PCSK9, which enhance the recycling of the LDL receptor to the cell surface in order to increase the rate at which LDL particles are removed from the blood; mipomersen (KYNAMERO), an antisense oligonucleotide used in the treatment of familial hypercholesterolemia (FH) that acts by hybridizing to apoB-100 and thus limiting the amount of LDL-C than can be formed; and lomitapide (JUXTAPID), also used in the treatment of FH, which prevents the formation and secretion of VLDL by inhibiting the microsomal triglyceride transfer protein in the liver. As with other cholesterol-lowering agents, these modalities are associated with adverse effects that limit their utility in certain patient populations (e.g., mipomersen and lomitapide have been associated with fatty liver disease caused by the accumulation of cholesterol in the liver).

As discussed further herein, macrophages play a large role in cholesterol homeostasis, through the uptake of LDL cholesterol, as well as the Ac-LDL and Ox-LDL forms of cholesterol. Although Kupffer Cells (KCs) only represent approximately 10-15% of the total 10-30 billion liver cells, KCs are 18 times more efficient in cholesterol catabolism than hepatocytes. Thus, modulation of KCs function and/or an increase in KCs number represent a novel avenue for the treatment and prevention of hypercholesterolemia and associated diseases, disorders and conditions. Embodiments of the current disclosure comprise the administration of an agent (e.g., a small molecule, a polypeptide, or an antibody) to a subject that modulates Kupffer cells (e.g., through increased activity and/or increased numbers) to effect the treatment and/or prevention of abnormally high levels of cholesterol and/or manifestation(s) of hypercholesterolemia in as subject. In particular embodiments, modulation of Kupffer cell function is used in the treatment and/or prevention of familial hypercholesterolemia (FH). In certain embodiments, the agent is an IL-10 agent (e.g., PEG-IL-10).

As discussed further hereafter, human IL-10 is a homodimer and each monomer comprises 178 amino acids, the first 18 of which comprise a signal peptide. Particular embodiments of the present disclosure comprise mature human IL-10 polypeptides lacking the signal peptide (see, e.g., U.S. Pat. No. 6,217,857), or mature human PEG-IL-10. In further particular embodiments, the IL-10 agent is a variant of mature human IL-10. The variant may exhibit activity less than, comparable to, or greater than the activity of mature human IL-10; in certain embodiments the activity is comparable to or greater than the activity of mature human IL-10.

The terms "IL-10", "IL-10 polypeptide(s)," "agent(s)" and the like are intended to be construed broadly and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, the terms "IL-10", "IL-10 polypeptide(s), "agent(s)" are agonists. Particular embodiments relate to pegylated IL-10, which is also referred to herein as "PEG-IL-10".

The present disclosure contemplates methods wherein the IL-10 agent comprises at least one modification to form a modified IL-10 agent, wherein the modification does not alter the amino acid sequence of the IL-10 agent. Certain embodiments of the present disclosure contemplate such modifications in order to enhance one or more properties (e.g., pharmacokinetic parameters, efficacy, etc.). In further embodiments, modification of IL-10 does not result in a therapeutically relevant, detrimental effect on immunogenicity, and in still further embodiments modified IL-10 is less immunogenic than unmodified IL-10. In some embodiments, the modified IL-10 agent is a PEG-IL-10 agent. The PEG-IL-10 agent may comprise at least one PEG molecule covalently attached to at least one amino acid residue of at least one subunit of IL-10 or comprise a mixture of mono-pegylated and di-pegylated IL-10 in other embodiments. The PEG component of the PEG-IL-10 agent may have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

Additional modified IL-10 agents are discussed in detail hereafter. In some embodiments, the modified IL-10 agent comprises at least one Fc fusion molecule, at least one serum albumin (e.g., HSA or BSA), an HSA fusion molecule or an albumin conjugate. In additional embodiments, the modified IL-10 agent is glycosylated, is hesylated, or comprises at least one albumin binding domain. Some modified IL-10 agents may comprise more than one type of modification. In particular embodiments, the modification is site-specific, and in still others it comprises a linker.

The present disclosure also contemplates nucleic acid molecules encoding the foregoing. Certain embodiments envisage the use of gene therapy in conjunction with the teachings herein. For gene therapy uses and methods, a cell in a subject can be transformed with a nucleic acid that encodes an IL-10-related polypeptide as set forth herein in vivo. Alternatively, a cell can be transformed in vitro with a transgene or polynucleotide, and then transplanted into a tissue of the subject in order to effect treatment. In addition, a primary cell isolate or an established cell line can be transformed with a transgene or polynucleotide that encodes an IL-10-related polypeptide, and then optionally transplanted into a tissue of a subject.

As delineated in the Experimental section, PEG-rMuIL-10 was found to decrease physiological plasma cholesterol levels by up to 70% in aggressively-challenged high fat diet-fed LDLR−/− mice in a phagocytotic cell-dependent manner. This finding, consistent between mice and humans, demonstrates the nexus between IL-10's regulation of KC scavenger receptor modulation and the enhancement of cholesterol uptake. Moreover, phagocytotic cells exert a consistent and powerful role in the normal endogenous regulation of total plasma cholesterol.

In particular embodiments, the present disclosure is drawn to a method of identifying an agent that induces phosphorylation of STAT3 in a KC, comprising: a) contacting a candidate agent with a KC, b) determining the level of STAT3 phosphorylation in the KC, and c) comparing the level of STAT3 phosphorylation in b) with the level of STAT3 phosphorylation induced by a reference standard, wherein a higher level of STAT3 phosphorylation in the KC compared to the level of STAT3 phosphorylation in the reference standard identifies the candidate agent as an agent that induces phosphorylation.

In some embodiments, an vitro model is used in identifying an agent that induces phosphorylation of STAT3 in a KC. In other embodiments, the KC is from a sinusoid of the liver.

In further embodiments of the present disclosure, the candidate agent comprises a small molecule, a polypeptide or an antibody.

The present disclosure also contemplates embodiments wherein the reference standard is an interleukin, an interferon, epidermal growth factor (EGF), hepatocyte growth factor (HGF), leukemia inhibitory factor (LIF), bone morphogenetic protein 2 (BMP-2), oncostatin M (OSM), or leptin. In particular embodiments, the interleukin is IL-5, IL-6 or IL-10.

The present disclosure further comprises methods of evaluating whether an agent that induces phosphorylation reduces at least one of serum cholesterol levels and triglyceride levels. In some methods, such evaluating is conducted with a biochemical assay, an in vitro assay, an ex vivo assay or an in vivo model.

The present disclosure also contemplates methods of identifying an agent that lowers serum cholesterol in a subject, comprising: a) administering a candidate agent to the subject, wherein the candidate agent induces STAT3 phosphorylation in a KC, b) determining the level of serum cholesterol in the subject, and c) comparing the level of serum cholesterol in b) with the level of serum cholesterol measured after administering a reference standard (e.g., a statin) to the subject, wherein the reference standard is known to lower serum cholesterol; wherein a candidate agent that lowers serum cholesterol more than or comparable to the reference standard identifies an agent that lowers serum cholesterol in the subject. In some embodiments of the present disclosure, the candidate agent comprises a small molecule, a polypeptide, or an antibody. Additional embodiments of the present disclosure further comprise evaluating whether the agent that lowers serum cholesterol in the subject induces hepatocyte proliferation.

Embodiments are contemplated wherein the subject is a human. The serum cholesterol level in a human may be from 200 to 239 mg/dL or at least 240 mg/dL. Further embodiments are contemplated wherein the animal model is a mouse model (e.g., an LDLR−/− mouse model).

The present disclosure also contemplates methods of lowering serum cholesterol in a subject in need thereof, comprising administering a therapeutically effective amount of an agent that modulates KC homeostasis. The KC homeostasis can comprise increasing the capacity of the KCs to remove lipoproteins from the serum, and/or it can comprise increasing the number of KCs removing lipoproteins from the serum.

An agent referenced in the preceding paragraph may be any agent identified using one of the aforementioned methods. In particular embodiments the agent is an IL-10 agent. These agents may be administered to a subject parenterally (e.g., subcutaneously), orally, or by any other means described herein or known to the skilled artisan.

Combination therapy is contemplated herein such that a therapeutically acceptable amount of at least one additional cholesterol-lowering agent is administered.

The present disclosure contemplates methods of treating or preventing hypercholesterolemia or a hypercholesterolemia-associated disease, disorder or condition in a subject (e.g., a human), comprising administering (for example, via parenteral (e.g., SC) or oral administration) to the subject a therapeutically effective amount of an agent identified using any of the methods described herein. The hypercholesterolemia-associated disease, disorder or condition can be a cardiovascular disorder (e.g., atherosclerosis), thrombosis or a thrombotic condition, an inflammatory disorder (e.g., vasculitis), or a fibrotic disorder. Specific embodiments are contemplated wherein a fibrotic disorder is hepatic-related, such as non-alcoholic fatty liver disease (NAFLD), non-alcoholic steatohepatitis (NASH) or cirrhosis.

In particular embodiments, methods can further comprise administering a therapeutically acceptable amount of at least one additional therapeutic or prophylactic agent, such as a cholesterol homeostasis agent (e.g., a statin, a bile acid resin, ezetimibe, a fibric acid, a niacin, or a PCSK9 inhibitor), an anti-obesity agent, or an anti-inflammatory agent. Other agents are contemplated herein for use in combination therapy, and these agents are known to those of ordinary skill in the art.

The present disclosure contemplates pharmaceutical compositions comprising a pharmaceutically effective amount of one or more of the aforementioned agents and a pharmaceutically acceptable diluent, carrier or excipient. Generally, such compositions are suitable for human administration. These pharmaceutical compositions may comprise one or more additional prophylactic or therapeutic agents, examples of which are described herein.

In certain embodiments, a sterile container (e.g., a vial or a syringe) may contain these pharmaceutical compositions. The sterile containers may be housed in a kit, which may also contain one or more additional prophylactic or therapeutic agent(s), means for reconstitution, directions for use, etc.

The present disclosure also contemplates methods of treating or preventing a liver disease, disorder or condition in a subject (e.g., a human), comprising administering (e.g., parenterally, including subcutaneously) to the subject a therapeutically effective amount of an IL-10 agent that modulates KC homeostasis, wherein the liver disease disorder or condition is non-alcoholic steatohepatitis (NASH) or non-alcoholic fatty liver disease (NAFLD).

Further embodiments of the present disclosure contemplate methods of treating or preventing a liver disease, disorder or condition in a subject (e.g., a human), comprising administering (e.g., parenterally, including subcutaneously) to the subject a therapeutically effective amount of an IL-10 agent that modulates KC homeostasis, wherein the amount is sufficient to achieve a mean IL-10 serum trough concentration from 1 pg/mL to 10.0 ng/mL; and wherein the liver disease disorder or condition is NASH or NAFLD.

In still further embodiments, the present disclosure contemplates methods of treating or preventing a liver disease, disorder or condition in a subject (e.g., a human), comprising administering (e.g., parenterally, including subcutaneously) to the subject a therapeutically effective amount of a cytokine (e.g., an IL-10 agent) that modulates KC homeostasis, wherein the amount is sufficient to maintain a mean cytokine (e.g., IL-10) serum trough concentration over a period of time; wherein the mean cytokine (e.g., IL-10) serum trough concentration is from 1.0 pg/mL to 10.0 ng/mL; wherein the mean cytokine (e.g., IL-10) serum trough concentration is maintained for at least 95% of the period of time; and wherein the liver disease disorder or condition is NASH or NAFLD. As used herein, the term "cytokine(s)" is meant to have its ordinary meaning in the art.

In certain methods, the mean cytokine (e.g., IL-10) serum trough concentration is in the range of from 0.1 ng/mL to 10 ng/mL, from 0.1 ng/mL to 5.5 ng/mL, from 0.5 ng/mL to 10 ng/mL, from 0.5 ng/mL to 5.5 ng/mL, from 0.75 ng/mL to 10.0 ng/mL, from 0.75 ng/mL to 5.5 ng/mL, from 0.9 ng/mL to 10.0 ng/mL, from 0.9 ng/mL to 5.5 ng/mL, from 0.9 ng/mL to 5.1 ng/mL, from 0.9 ng/mL to 5.0 ng/mL, from 0.9 ng/mL to 4.5 ng/mL, from 0.9 ng/mL to 4.0 ng/mL, from 0.9 ng/mL to 3.5 ng/mL, from 0.9 ng/mL to 3.0 ng/mL, from 1.0 ng/mL to 5.1 ng/mL, from 1.0 ng/mL to 5.0 ng/mL, from 1.0 ng/mL to 4.5 ng/mL, from 1.0 ng/mL to 4.0 ng/mL, from 1.0 ng/mL to 3.5 ng/mL, or from 1.0 ng/mL to 3.0 ng/mL. The present disclosure contemplates methods wherein the cytokine (e.g., an IL-10 agent) is administered to the subject at least twice daily, at least once daily, at least once every 48 hours, at least once every 72 hours, at least once weekly, at least once every 2 weeks, at least once monthly, at least once every 2 months, or at least once every 3 months, or less frequent. In some embodiments of the methods described herein, the mean IL-10 serum trough concentration is maintained for at least 90% of the period of time, for at least 95% of the period of time, for at least 97% of the period of time, for at least 99% of the period of time, or for 100% of the period of time.

The present disclosure contemplates embodiments wherein the IL-10 agent is mature human IL-10 or a variant of mature human IL-10. In particular embodiments, the variant exhibits activity comparable to the activity of mature human IL-10.

In some embodiments, the disease, disorder or condition is NASH, and in other embodiments it is NAFLD.

The modulation of Kupffer cell homeostasis comprises increasing the capacity of KCs to remove lipoproteins from the serum in some embodiments, and increasing the number of KCs to remove lipoproteins from the serum in others.

Embodiments are contemplated herein wherein the cytokine (e.g., an IL-10 agent) decreases hepatic cholesterol and/or triglycerides, decreases or reverses peri-portal collagen deposition, or increases the number of hepatocytes.

Some embodiments also comprise administering the cytokine (e.g., an IL-10 agent) with at least one additional prophylactic or therapeutic agent. In certain embodiments of the present disclosure, the prophylactic or therapeutic agent is a cholesterol homeostasis agent. In some embodiments, the cholesterol homeostasis agent comprises a statin, a bile acid resin, ezetimibe, a fibric acid, a niacin, or a PCSK9 inhibitor. The cholesterol hemostasis agent frequently improves, either directly or indirectly, a cardiovascular disorder. In particular embodiments, a prophylactic or therapeutic agent is one useful in the prevention or treatment of atherosclerosis. In additional embodiments, the prophylactic or therapeutic agent is an anti-diabetic agent or an anti-obesity agent, whereas in other embodiments it is an immune agent or an anti-inflammatory agent. Additional exemplary prophylactic and therapeutic agents are set forth hereafter.

Other embodiments of the present disclosure are described herein, while still others would be envisaged by the skilled artisan after reviewing this disclosure.

BRIEF DESCRIPTION OF THE DRAWINGS

FIGS. 2A-2L illustrate the effect of PEG-rMuIL-10 on the expression of genes associated with liver function and cholesterol regulation.

DETAILED DESCRIPTION

Figures 1A, 1B, 1C, 1D, 1E, 1F, 1G, 1H, 1I, 1J, 1K, 1L:
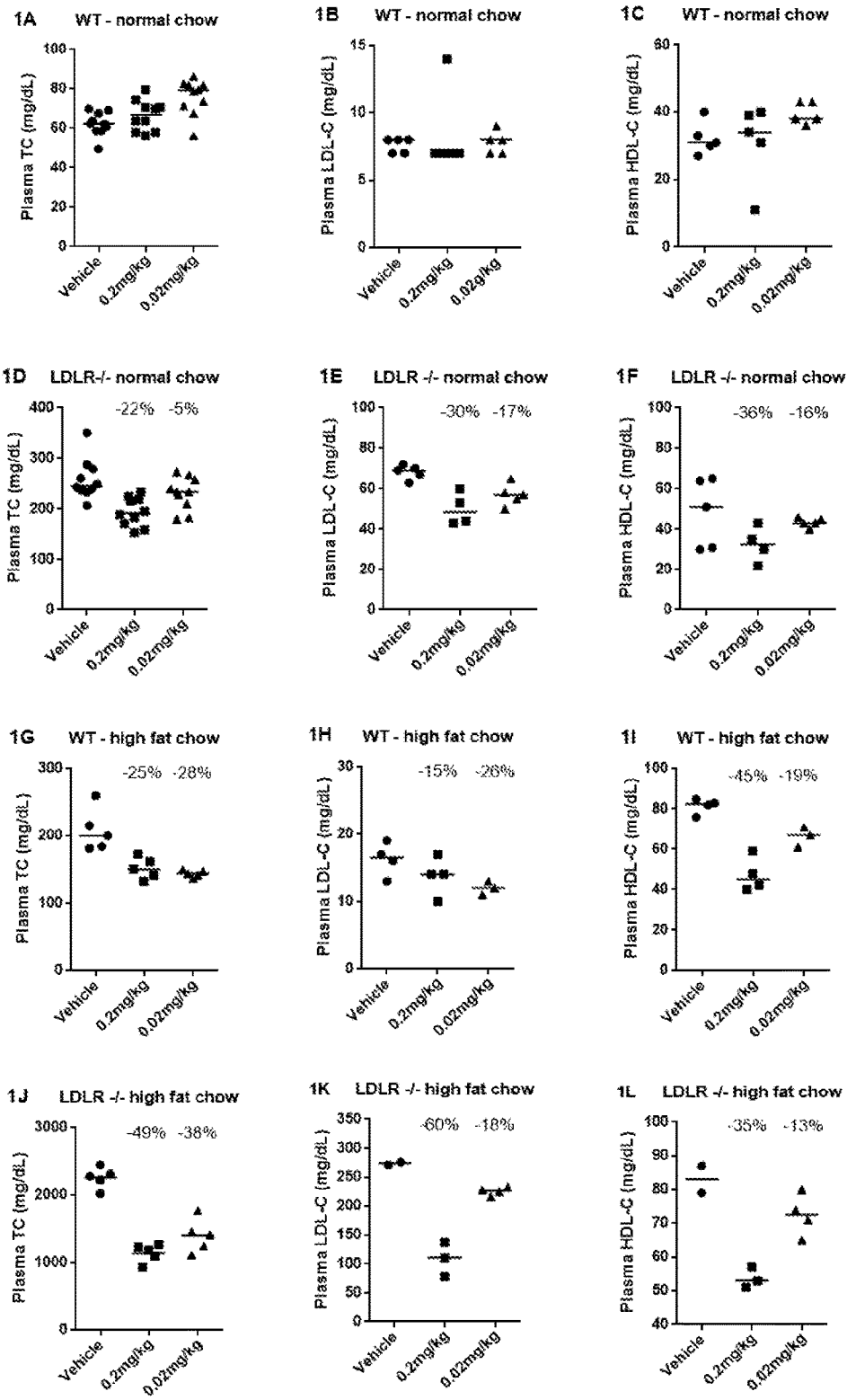
FIGS. 1A-1L illustrate the regulatory effect of PEG-rMuIL-10 on plasma cholesterol levels in wild-type and LDLR-/- mice fed a normal and high fat diet.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

The present disclosure contemplates the use of the agents described herein, and compositions thereof, to treat and/or prevent various metabolic-related diseases (e.g., hypercholesterolemia), disorders and conditions, and/or the symptoms thereof.

The present disclosure also contemplates the use of IL-10 agents (e.g., an IL-10 polypeptide) and other cytokines to treat or prevent a liver disease, disorder or condition comprising administering an IL-10 agent (or other cytokine agents) that modulates Kupffer cell homeostasis. In particular embodiments, the liver disease disorder or condition is non-alcoholic steatohepatitis (NASH) or non-alcoholic fatty liver disease (NAFLD).

In certain aspects of the present disclosure, such treatment or prevention is effected by utilizing particular dosing parameters. The present disclosure is based on the findings that there is an optimal mean IL-10 (or other cytokine) serum trough concentration range and an optimal dosing range that achieves therapeutically relevant reduction of serum cholesterol.

In some embodiments of the present disclosure, a subject having, or at risk of having, a disease or disorder treatable by an IL-10 agent (or other cytokine agent) is administered the IL-10 agent in an amount sufficient to achieve a serum trough concentration greater than about 1 ng/mL but less than about 10 ng/mL, whereas in other embodiments the serum trough concentration is greater than about 2 ng/mL but less than about 10 ng/mL.

Some of the embodiments and descriptions set forth herein are described in the context of an IL-10 agent (e.g., a PEG-IL-10 agent). It is to be understood that, when appropriate in view of the context in which it is being used, recitation of an IL-10 agent may also refer more broadly to a cytokine agent.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates IL-10-related polypeptides and corresponding nucleic acid molecules (and, in certain instances, cytokine polypeptides and corresponding nucleic acid molecules) from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties (e.g., signaling or adhesion). Moreover, the term includes a membrane-bound ligand that has been changed, e.g., by chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex".

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an agent (e.g., an IL-10 agent) (or the nucleic acid molecules encoding them), either directly or indirectly; or to enhance the ability of a molecule to produce an effect comparable to that of an agent (e.g., an IL-10 agent). The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator may act alone, or it may use a cofactor, e.g., a protein, metal ion, or small molecule. The term "modulator" includes agents that operate through the same mechanism of action as an agent (e.g., an IL-10 agent) (i.e., agents that modulate the same signaling pathway as an agent (e.g., an IL-10 agent) in a manner analogous thereto) and are capable of eliciting a biological response comparable to (or greater than) that of an agent (e.g., an IL-10 agent).

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term may also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |

| | | | | | |
|---|---|---|---|---|---|
| E | Glutamic Acid | Glu | D | Aspartic Acid | Asp |
| S | Serine | Ser | T | Threonine | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). Thus, herein a "mutein" refers broadly to mutated recombinant proteins that usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than that of the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-10 and PEG-IL-10

The anti-inflammatory cytokine IL-10, also known as human cytokine synthesis inhibitory factor (CSIF), is classified as a type (class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. Although predominantly expressed in macrophages, IL-10 expression has also been detected in activated T cells, B cells, mast cells, and monocytes. It is produced by mast cells, counteracting the inflammatory effect that these cells have at the site of an allergic reaction. While IL-10 predominantly limits the production and secretion of pro-inflammatory cytokines in response to toll-like receptor agonists, it is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

As a result of its pleiotropic activity, IL-10 has been linked to a broad range of diseases, disorders and conditions, including inflammatory conditions, immune-related disorders, fibrotic disorders, metabolic disorders, including regulation of cholesterol, and cancer. Clinical and pre-clinical evaluations with IL-10 for a number of such diseases, disorders and conditions have solidified its therapeutic potential.

Human IL-10 is a homodimer with a molecular mass of 37 kDa, wherein each 18.5 kDa monomer comprises 178 amino acids, the first 18 of which comprise a signal peptide. Each monomer comprises four cysteine residues that form two intramolecular disulfide bonds. The IL-10 dimer becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601). The description herein generally refers to the homodimer; however, certain aspects of the discussion can also apply to a monomer, as will be apparent from the context.

The various embodiments of the present disclosure contemplate human IL-10 (NP_000563) and murine IL-10 (NP_034678), which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

As alluded to above, the terms "IL-10", "IL-10 polypeptide(s), "IL-10 molecule(s)", "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists.

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

The utility of recombinant human IL-10 is frequently limited by its relatively short serum half-life, which can be due to, for example, renal clearance, proteolytic degradation and monomerization in the blood stream. As a result, various approaches have been explored to improve the pharmacokinetic profile of IL-10 without disrupting its dimeric structure and thus adversely affecting its activity. Pegylation of IL-10 results in improvement of certain pharmacokinetic parameters (e.g., serum half-life) and/or enhancement of activity. As used herein, the terms "pegylated IL-10" and "PEG-IL-10" refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. As used herein, the terms "dipegylated IL-10" and "di-PEG-IL-10" indicate that at least one polyethylene glycol molecule is attached to a single residue on each subunit of the IL-10 dimer, generally via a linker.

In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing the pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein.

In some embodiments, an N-terminal pegylation chemistry strategy can be used that results in pegylation of the N-terminus with approximately 99% specificity over a defined time period (e.g., less than 18 hours). Allowing the chemical reaction to continue beyond that time period results in an increase in lysine side chain pegylation. Several pegylation approaches are described in the Experimental section.

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity. The biological activity of PEG-IL-10 is typically measured by assessing the levels of inflammatory cytokines (e.g., TNF-β or IFN-γ) in the serum of subjects challenged with a bacterial antigen (lipopolysaccharide (LPS)) and treated with PEG-IL-10, as described in U.S. Pat. No. 7,052,686.

IL-10 variants (unmodified by, e.g., pegylation or HSA conjugation) can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some can be post-translational variants, e.g., glycosylated variants. Any variant of IL-10 can be used provided it retains a suitable level of IL-10 activity. As with wild-type IL-10, these IL-10 variants can be modified (by, e.g., pegylation or Fc fusion) as described herein.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions can be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides can be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides can be isolated from a non-natural source (e.g., an environment other than its naturally-occurring environment) and can also be recombinantly made (e.g., in a genetically modified host cell such as bacteria, yeast, Pichia, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

As previously indicated, the present disclosure also contemplates the use of gene therapy in conjunction with the teachings herein. Gene therapy is effected by delivering genetic material, usually packaged in a vector, to endogenous cells within a subject in order to introduce novel genes, to introduce additional copies of pre-existing genes, to impair the functioning of existing genes, or to repair existing but non-functioning genes. Once inside cells, the nucleic acid is expressed by the cell machinery, resulting in the production of the protein of interest. In the context of the present disclosure, gene therapy is used as a therapeutic to deliver nucleic acid that encodes an IL-10 agent for use in the treatment or prevention of a disease, disorder or condition described herein.

As alluded to above, for gene therapy uses and methods, a cell in a subject can be transformed with a nucleic acid that encodes an IL-10-related polypeptide as set forth herein in vivo. Alternatively, a cell can be transformed in vitro with a transgene or polynucleotide, and then transplanted into a tissue of a subject in order to effect treatment. In addition, a primary cell isolate or an established cell line can be transformed with a transgene or polynucleotide that encodes an IL-10-related polypeptide, and then optionally transplanted into a tissue of a subject.

Cholesterol Homeostasis

Physiology:

Cholesterol plays an indispensable role in a vast array of physiological processes, including cell membrane structure, and biosynthesis of steroid hormones, bile acids and vitamin D. Cholesterol synthesis entails a complex 37-step process that begins with the reduction of 3-hydroxy-3-methylglutaryl CoA (HMG-CoA) to mevalonate by the enzyme HGM-CoA reductase. This is the regulated, rate-limiting and irreversible step in cholesterol synthesis and is the site of action for the statin drugs (HMG-CoA reductase competitive inhibitors).

The liver is the major regulator of cholesterol. Not only is it the site of formation of VLDL, the precursor of most LDL in the circulation, it is also the location where the vast majority of receptor-mediated clearance of LDL takes place.

The liver initially clears all the cholesterol that is absorbed from the small intestine. Absorption of excess cholesterol may increase the amount of cholesterol stored in the liver, resulting in increased VLDL secretion (and thus LDL formation) and down-regulation of hepatic LDL-receptor activity. On average, about half of all cholesterol entering the intestine is absorbed. The fractional absorption rate varies greatly among individuals, which may explain, at least in part, why some patients respond poorly, or not at all, to statins and other classes of lipid-lowering drugs. See, e.g., Turley, S D, (2004) Clin. Cardiol. 6 Suppl 3:11116-21. The liver also recycles cholesterol by excreting it in a non-esterified form (via bile) into the digestive tract.

Lipid Panel:

Total cholesterol is defined as the sum of LDL, HDL, and VLDL. In general, total blood cholesterol levels <200 mg/dL are considered normal, levels between 200-239 mg/dL are considered borderline-high, and levels >240 mg/dL are considered high.

Since 1988, the National Cholesterol Education Program (NCEP) has issued guidelines identifying LDL as the primary target of cholesterol therapy. The current guidelines, set forth in Adult Treatment Panel-III (ATP-III), set a goal for LDL<100 mg/dL (2.6 mmol/L). Increased LDL is associated with atherosclerotic disease, which confers high risk for coronary heart disease (CHD)-related events, including clinical CHD, symptomatic carotid artery disease, peripheral arterial disease, and abdominal aortic aneurysm. Diseases, disorders and conditions associated with elevated cholesterol levels, and the treatment and/or prevention thereof, are described in detail hereafter.

There is considerable evidence indicating that low levels of high-density cholesterol (HDL-C, or simply HDL) are a contributory factor in the development of atherosclerosis and CHD. Low HDL is one of the most common lipid disorders in patients with premature coronary artery disease. Patients with hypertriglyceridemia usually have lower HDL cholesterol. Certain medications, including beta-blockers, progesterone and testosterone, also lower HDL levels.

In the average man, HDL cholesterol levels range from 40 to 50 mg/dL, whereas in the average woman, they range from 50 to 60 mg/dL. Studies have indicated that the median values of HDL associated with the lowest risk for atherosclerotic events are 62 mg/dL in men and 81 mg/dL in women. The ATP-III guidelines for lipid-lowering therapy established an HDL level below 40 mg/dL as a major positive risk factor and LDL level ≥60 mg/dL as a negative risk factor (i.e., protective). A ratio of total cholesterol to HDL of less than 5:1 is considered to be desirable.

Triglycerides are predominantly carried in the blood stream by very low density lipoproteins (VLDL). There is considerable heterogeneity of triglyceride-rich particles. Triglyceride-rich particles derived from dietary fat—chylomicrons—are not themselves associated with CHD, but, when very high (>1,000 mg/dL) can cause pancreatitis, venous and arterial thrombi, acute heart attack and stroke. However, these chylomicron particles are gradually reduced in size by lipoprotein lipase to intermediate density lipoproteins (IDL) which are atherogenic. Similarly, VLDL from the liver is reduced in size by lipoprotein lipase, producing atherogenic IDL. VLDL is predictive of progression of coronary artery disease and CHD events, and thus hypertriglyceridemia has been increasingly recognized as a risk factor for CHD.

High triglyceride levels either result from genetic causes or are acquired. In terms of genetic causes, about 1/500 people have an inherited tendency towards high plasma triglycerides. Acquired high triglycerides are most commonly associated with excessive alcohol intake, exogenous estrogens or estrogen agonists, poorly controlled diabetes, beta-blockers, corticosteroids, and uremia. Triglycerides levels in excess of 1,000 mg/dL reflect an acquired cause for high triglycerides superimposed on a genetic cause. Less common causes of acquired high triglycerides include kidney failure, nephrotic syndrome, albuminuria, hypothyroidism, many liver diseases, hemochromatosis, hyperparathyroidism, and glycogen storage disease.

According to the American Heart Association, triglyceride levels of less than 150 mg/dL are normal; levels from 150 to 199 mg/dL are borderline high; levels from 200 to 499 mg/dL are high; and levels ≥500 mg/dL are very high. In general, triglyceride levels between 150 and 200 mg/dL are not pharmacologically treated.

Testing:

Several general methods and systems have been used in evaluating a subject's lipid profile. Any method or system, now in existence or subsequently developed, may be used in conjunction with the teachings of the present disclosure.

Fasting cholesterol tests, which generally utilize a colorimetric assay system, are the traditional means for measuring total serum cholesterol. Such tests require blood to be drawn after a 12-hour fast to determine a lipoprotein profile. Usually, only the total cholesterol, HDL, and triglycerides are measured; for cost reasons, VLDL is generally not measured, but rather is estimated as one-fifth of the triglycerides, and the LDL is estimated using the Friedewald formula. Although such tests are inexpensive and widely available (e.g., Sigma-Aldrich, St. Louis, Mo.; BioVision, Inc., Milpitas, Calif.), they require fasting and are not as sensitive as other tests because LDL is estimated rather than determined accurately.

When assessing hypercholesterolemia, it is frequently useful to measure all lipoprotein subfractions (VLDL, IDL, LDL and HDL). Because a particular therapeutic goal is to decrease LDL (while maintaining or increasing HDL), cholesterol tests that directly measure LDL levels are more accurate, and they are especially useful for those patients who have elevated triglycerides. Though commercially available (e.g., Beckman Coulter, Inc.; Brea, Calif.), use of these direct measurement tests is sometimes limited due to their cost.

The Role of Kupffer Cells in Cholesterol Homeostasis

Macrophages are often categorized by function and location; blood monocytes, liver Kupffer cells (liver-specific macrophages), fixed tissue macrophages, and various dendritic cells are among the most prevalent types of macrophages.

Kupffer cells (KCs), large fixed macrophages constituting 80-90% of the tissue macrophages present in the body, reside within the lumen of the hepatic sinusoids and exhibit endocytic activity against blood-borne materials entering the liver. KCs play a major role in the physiological maintenance of the hepatic architecture and are intimately involved in the liver's response to infection (e.g., HCV), toxins (e.g., alcohol and drugs), ischemia, resection and other stresses (e.g., trauma).

Upon activation (by, for example, bacterial endotoxins), KCs release various factors, including cytokines, prostanoides, nitric oxide and reactive oxygen species, that regulate the phenotype of KCs themselves, and the phenotypes of neighboring cells such as hepatocytes, stellate cells, endothelial cells and other immune cells that traffic through the liver. Macrophage scavenger receptors are expressed in KCs, and such scavenger receptors are involved not only in bactericidal processes, but also in lipid metabolism. Evidence suggests that KCs represent a distinct cell population with unique differentiation mechanisms, metabolic functions, and responsiveness to inflammatory agents.

STAT3.

The transcription factor STAT3 (signal transducer and activator of transcription 3) is a member of the STAT protein family. In response to cytokines and growth factors, STAT family members are phosphorylated by receptor-associated kinases; thereafter, they form homo- or heterodimers that translocate to the cell nucleus, where they act as transcription activators. STAT3 plays a key role in many cellular processes, including cell growth and apoptosis. It is essential for the differentiation of TH17 helper T cells, which play a role in a variety of autoimmune diseases. Moreover, STAT3 has been implicated in the regulation of lipid metabolism. (See Kinoshita et al., Kobe J. Med. Sci., Vol. 54, No. 4, pp. E200-E208, 2008).

STAT3 phosphorylation occurs in response to various cytokines and growth factors, including certain interleukins (e.g., IL-5, IL-6 and IL-10), leukemia inhibitory factor (LIF), epidermal growth factor (EGF), certain interferons, hepatocyte growth factor (HGF), bone morphogenetic protein 2 (BMP-2), the cytokine oncostatin M (OSM), and the hormone leptin. IL-6 lowers serum cholesterol in mice and humans, human LIF decreases serum cholesterol in hypercholesterolemic rabbits, and OSM decreases serum cholesterol in hypercholesterolemic hamsters; this cholesterol reduction is believed to be effected through upregulation of the LDL receptor.

The present disclosure is based, in part, on the discovery that the capacity of KC to remove lipoproteins from the serum can be modulated (e.g., increased) in order to effect desirable metabolic effects (e.g., cholesterol lowering). In particular aspects, the present disclosure is drawn to methods of identifying agents that induce the phosphorylation of STAT3 in KCs, thereby increasing their ability to remove lipoproteins from the serum. As noted herein, while an understanding of the underlying mechanism of action by which KCs are involved in cholesterol lowering is not required in order to practice the present disclosure, agents that induce STAT3 phosphorylation in KCs are believed to increase KCs' capacity for scavenging lipoproteins from the serum. In this context, the phrase "agents that induce STAT3 phosphorylation" is meant to refer broadly to any molecule (e.g., a small molecule, a polypeptide, and an antibody) that causes, directly or indirectly, in whole or in part, an increase in phosphorylated STAT3. In particular embodiments, such agents are factors which drive the phosphorylation of STAT3 (e.g., IL-10, IL-6, LIF and Oncostatin M).

Scavenger Receptors.

Scavenger receptors participate in the removal of many foreign substances and waste materials in the body by extensive ligand specificity and a variety of receptor molecules. They constitute a group of receptors that recognize and uptake negatively charged macromolecules, as well as LDL that has been modified by oxidation (oxLDL) or acetylation (acLDL).

Scavenger receptors are generally categorized into three categories—Class A, Class B, and Class C—according to their structural characteristics. Class A Scavenger Receptors (Scavenger receptors type 1 (SR-A1) and 2 (SR-A2)) are trimers that preferentially bind modified LDL (e.g., oxLDL and acLDL) and have a collagen-like domain essential for ligand binding. Class A members include MSR1 (also known as SCARA1), MARCO (also known as SCARA2), SCARA3, COLEC12 (also known as SCARA4), and SCARA5.

Class B Scavenger Receptors are identified as oxidized LDL receptors, and its members include CD36 and Scavenger Receptor Class BI (SR-BI). Class B Scavenger Receptors are often referred to as SCARB1 (which also interacts with HDL); SCARB2; and SCARB3 (also known as CD36), which has been implicated in phagocytosis of apoptotic cells and in metabolism of long-chain fatty acids. Class C Scavenger Receptors include other receptors that can bind to oxidized LDL, including CD68, Mucin, and Lectin-like oxidized LDL receptor-1 (LOX-1).

As described herein, the uptake process of modified LDL by scavenger receptors is followed by intracellular degradation and/or efflux onto HLD particles. IL-10 has been shown to be involved in the uptake and efflux processes, and likely contributes to the degradation process as well.

Scavenger receptor function was evaluated herein (see Experimental section) for, among others, MSR1, MARCO, SCARB1, SCARB2, and CD36. When the effect of IL-10 (PEG-rMuIL-10) on the expression of genes associated with liver function and cholesterol regulation was assessed, only two primary groups of genes were altered, one of which was scavenger receptors (see Example 2 and FIG. 2). As indicated in FIGS. 2E-H, Msr1 and Marco, Type A scavenger receptors, were induced by 2-7 fold in wild-type and LDLR−/− mice on normal chow diet; and wild-type and LDLR−/− mice on high-fat chow diet. In addition, because scavenger receptors are predominantly expressed on macrophage-type cells, differences in gene expression of F4/80 and CD14, two cell surface proteins most often expressed on liver tissue resident macrophages, were assessed, and these genes were moderately induced across the different genetic backgrounds and dietary conditions (see FIGS. 2E-H). FIGS. 3A-D indicate the effect of PEG-rMuIL-10 on Msr1 (see Example 3). These data confirm the role of scavenger receptors in aspects of liver function and cholesterol regulation.

Effect of PEG-IL-10 and Other Cytokines on Cholesterol Homeostasis and KC Function IL-10's Role in Cholesterol Homeostasis.

The extent by which PEG-IL-10 reduces plasma cholesterol is related to the subject's total cholesterol level. This was observed in both mice and humans. As indicated in Example 1 and FIG. 1, PEG-rMuIL-10 lowered plasma cholesterol only in hypercholesterolemic mice, and PEG-rHuIL-10 lowered plasma cholesterol only in patients with elevated plasma cholesterol levels. To illustrate, cancer patients with border-line high (~200 mg/dL) total cholesterol achieved an approximately 40% cholesterol reduction following administration of PEG-rHuIL-10 SC daily, whereas patients with low (~100 mg/dL) total cholesterol were unaffected. These data suggest that PEG-IL-10 is more efficacious in patient populations that would benefit the most from cholesterol reduction.

This response is believed to be triggered by the level of IL-10Rα expression, as a high fat diet induced upregulation of the IL-10Rα in mouse liver (data not shown).

The present disclosure contemplates the administration of cytokines (e.g., PEG-IL-10) to subjects that would benefit from cholesterol reduction, regardless of their total cholesterol levels. Thus, for example, in some embodiments PEG-IL-10 is administered to subjects having a total cholesterol level of at least 150 mg/dL, at least 160 mg/dL, at least 170 mg/dL, at least 180 mg/dL, at least 190 mg/dL, at least 200 mg/dL, at least 210 mg/dL, at least 220 mg/dL, at least 230 mg/dL, at least 240 mg/dL, at least 250 mg/dL, at least 260 mg/dL, at least 270 mg/dL, at least 280 mg/dL, at least 290 mg/dL, or at least 300 mg/dL. In other embodiments, PEG-IL-10 is administered to subjects having a total cholesterol level of at least 325 mg/dL, at least 350 mg/dL, at least 375 mg/dL, at least 400 mg/dL, at least 425 mg/dL, at least 450 mg/dL, at least 475 mg/dL, or at least 500 mg/dL.

In particular embodiments, an IL-10 agent (or other cytokine agent) disclosed herein (e.g., PEG-IL-10) has an anti-hyperlipidemia activity capable of reducing the levels of VLDL, IDL, LDL, or a combination thereof by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other embodiments, an IL-10 agent (or other cytokine agent) disclosed herein (e.g., PEG-IL-10) has anti-hyperlipidemia activity capable of reducing the levels of VLDL, IDL, LDL, or a combination thereof in a range from, e.g., about 10% to about 100%, about 20% to about 100%, about 30% to about 100%, about 40% to about 100%, about 50% to about 100%, about 60% to about 100%, about 70% to about 100%, or about 80% to about 100%; about 10% to about 90%, about 20% to about 90%, about 30% to about 90%, about 40% to about 90%, about 50% to about 90%, about 60% to about 90%, or about 70% to about 90%; about 10% to about 80%, about 20% to about 80%, about 30% to about 80%, about 40% to about 80%, about 50% to about 80%, or about 60% to about 80%; about 10% to about 70%, about 20% to about 70%, about 30% to about 70%, about 40% to about 70%, or about 50% to about 70%.

In another embodiment of the present disclosure, an IL-10 agent (or other cytokine agent) disclosed herein (e.g., PEG-IL-10) increases the level of HDL. In some other (often more frequent) embodiments, the level of HDL itself does not increase; rather the levels of both LDL and HDL decrease, but the level of LDL decrease exceeds the level of HDL decrease such that the change in the final ratio of LDL to HDL is consistent with the HDL lipid hypothesis. In an aspect of these embodiments, the IL-10 agent (or other cytokine agent) increases the level of HDL relative to LDL by, e.g., at least 2%, at least 3%, at least 10%, at least 12%, at least 15%, at least 17%, at least 20%, at least 22%, at least 25%, at least 27%, at least 30%, at least 32%, at least 35%, at least 37%, at least 40%, at least 42%, at least 45% or at least 47%. In yet other aspects of these embodiments, the IL-10 agent increases the level of HDL relative to LDL in a range from, e.g., about 2% to about 100%; about 10% to about 50%, about 15% to about 50%, about 20% to about 50%, about 25% to about 50%, about 30% to about 50%, about 35% to about 50%, or about 40% to about 50%; about 2% to about 45%, about 10% to about 45%, about 15% to about 45%, about 20% to about 45%, about 25% to about 45%, about 30% to about 45%, or about 35% to about 45%; about 2% to about 40%, about 10% to about 40%, about 15% to about 40%, about 20% to about 40%, about 25% to about 40%, or about 30% to about 40%; about 2% to about 35%, about 10% to about 35%, about 15% to about 35%, about 20% to about 35%, or about 25% to about 35%.

IL-10's Role in KC Function.

Although an understanding of the underlying mechanism by which IL-10 exerts its effects is not required in order to practice the present disclosure, as previously alluded to, IL-10 activates the myeloid immune system through activation of liver resident KCs to dramatically reduce systemic cholesterol levels in subjects having hypercholesterol.

As detailed in the Experimental section, the regulatory effect of PEG-rHuIL-10 on total plasma cholesterol was determined using a murine surrogate, PEG-rMuIL-10. FIGS. 2A-D indicate that PEG-rMuIL-10 decreased two genes (Hmgcs1 and Hmgcs2) involved in cholesterol synthesis.

Administration of PEG-rMuIL-10 to LDLR−/− mice decreased total plasma cholesterol in a manner that is commensurate with increased scavenger receptor expression in KCs, and KCs were shown to be the predominant myeloid cell type that responded to PEG-rMuIL-10 with increased scavenging of LDL. Because removal of all phagocytotic cells, the majority of which are myeloid lineage cells, dramatically increased plasma cholesterol, phagocytotic cell populations play a major role in the regulation of plasma cholesterol levels.

Treatment of NAFLD and NASH with IL-10 and Other Cytokines

Non-alcoholic steatohepatitis (NASH), considered part of a spectrum of non-alcoholic fatty liver diseases (NAFLD), causes inflammation and accumulation of fat and fibrous tissue in the liver. Although the exact cause of NASH is unknown, risk factors include central obesity, type-2 diabetes mellitus, insulin resistance (IR) and dyslipidemia; combinations of the foregoing are frequently described as the metabolic syndrome. In addition, certain drugs have been linked to NASH, including tamoxifen, amiodarone and steroids (e.g., prednisone and hydrocortisone). Non-alcoholic fatty liver disease is the most common cause of chronic liver disease in the United States, and the estimated prevalence of NAFLD is 20-30% and for NASH it is estimated at 3.5-5%. (See, e.g., Abrams, G. A., et al., Hepatology, 2004. 40(2):475-83; Moreira, R. K., Arch Pathol Lab Med, 2007. 131(11):1728-34).

NASH frequently presents with no overt symptoms, complicating its diagnosis. Liver function tests generally begin the diagnostic process, with levels of AST (aspartate aminotransferase) and ALT (alanine aminotransferase) elevated in about 90% percent of individuals with NASH. Other blood tests are often used for ruling out other causes of liver disease, such as hepatitis. Imaging tests (e.g., ultrasound, CT scan, or MRI) may reveal fat accumulation in the liver but frequently cannot differentiate NASH from other causes of liver disease that have a similar appearance. A liver biopsy is required to confirm NASH.

The prognosis for individuals suffering from NASH is difficult to predict, although features in the liver biopsy can be helpful. The most serious complication of NASH is cirrhosis, which occurs when the liver becomes severely scarred. It has been reported that between 8 and 26 percent of individuals with NASH develop cirrhosis, and it is predicted that NASH will be the leading indication for liver transplantation by 2020.

At the present time, treatment of NASH focuses primarily on pharmacological and non-pharmacological management of those medical conditions associated with it, including hyperlipidemia, diabetes and obesity. Although not curative, pharmacological intervention of NASH itself includes treatment with vitamin E, pioglitazone, metformin, statins, omega-3 fatty acids, and ursodeoxycholic acid (UDCA (ursodiol)). Other agents being evaluated, currently approved for different indications, include losartan and telisartan, exenatide, GLP-1 agonists, DPP IV inhibitors, and carbamazepine. Combination therapy is hoped to offer new opportunities for disease control.

Historically, the activation of Kupffer cells has been associated with the initiation and progression of liver disease (Kolios, G. et al., World J. Gastroenterol, 2006. 12(46): 7413-20). In particular, Kupffer cells were believed to be involved in alcoholic liver disease, (ALD) (Eguchi, H., et al., Hepatology, 1991. 13(4):751-57), non-alcoholic fatty liver disease, (NAFLD) (Stienstra R., et al., Hepatology, 2010. 51(2):511-22, and non-alcoholic steatohepatitis, (NASH) (Tomita, K. et al., Gut, 2006. 55(3):415-24). In general, these diseases were thought to be linked by the inappropriate accumulation of liver cholesterol and triglycerides within both the Kupffer cells and hepatocytes. Thus, there has been the belief that depletion of KC function might be therapeutically relevant in the treatment of metabolic disorders such as NASH. (Neyrinck et al., Biochem. Biophys. Res. Comm., 385:351-56 (2009)).

The teachings of the present disclosure are diametrically opposed to this belief. While it has been reported that activation of KCs is necessary to optimize liver regeneration (Bilzer, M et al., (2006), Liver Int, 26:1175-86), it was not previously recognized that KCs play an integral role in cholesterol and triglyceride regulation. Embodiments of the present disclosure are associated with the novel finding that aspects of KC function entail significant uptake of serum cholesterol and, thereafter, its removal and catabolism. The alteration to collagen deposition described herein is linked to the removal of triglycerides, which then leads to the removal of the pro-inflammatory stimulus, permitting the resolution of peri-portal injury and fibrosis.

As described in the Experimental section, IL-10 (e.g., PEG-IL-10) activation of KCs' scavenging capacity is associated with decreases in the accumulation of liver cholesterol and triglycerides, and certain embodiments of the present disclosure contemplate the use of PEG-IL-10 to induce the removal of accumulated liver triglycerides and cholesterol. Induction of the removal of accumulated liver triglycerides and cholesterol, in turn, results in the reversal of early liver fibrosis and facilitates the restoration of liver health through, for example, increasing the number of hepatocytes in the liver. These data support the use of IL-10

(e.g., PEG-Il-10) for the treatment of NAFLD and NASH. Thus, particular embodiments of the present disclosure contemplate the use of IL-10 (including human and non-human IL-10-related polypeptides, including homologs, variants (including muteins), and fragments thereof) in the treatment and/or prevention of NAFLD and NASH.

In addition, other cytokines can effect depletion of KC function and can be therapeutically relevant in the treatment of liver-related disorders such as NAFLD and NASH. As used herein, the term "cytokine(s)" is meant to have its ordinary meaning in the art. Cytokines are involved in cell signaling—cells of the immune system communicate with one another by releasing and responding to cytokines. Cytokines encompass a diverse array of proteins that include interleukins, interferons, chemokines, lymphokines, and tumor necrosis factor. They are produced by broad range of cells, including macrophages, B lymphocytes, T lymphocytes, mast cells, fibroblasts, and endothelial cells.

Cytokines modulate the balance between humoral- and cell-based immune responses and regulate the maturation, growth, and responsiveness of particular cell populations. They also play an integral role in host responses to, for example, infection, immune responses, inflammation, and trauma. Although not readily subject to definitive classification, cytokines are sometimes classified as interleukins, lymphokines, monokines, interferons, colony stimulating factors and chemokines.

In particular embodiments, the present disclosure contemplates the use of cytokines in the treatment and/or prevention of liver-related disorders such as NAFLD and NASH. Dosing regimens applicable to cytokine agents in general, and IL-10 agents in particular, are described elsewhere herein.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as 9-fluorenylmethoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis may be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α, α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition, the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecyl-silylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., E. coli) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide may be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH$_2$NH—, —CH$_2$S—, —CH$_2$CH$_2$—, —CH=CH-(cis and trans), —COCH$_2$—, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C$_1$-C$_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from C$_1$-C$_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from C$_1$-C$_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diamino-propionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, κ-amino hexanoic acid, w-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and $-(CH2)_n$-CO— or $-(CH2)_n$-$C_6H_4$—CO—) with functional groups which allow for the introduction of a bridge. Some examples are disulfides, disulfide mimetics such as the $-(CH2)_n$-carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids.) See, e.g., Jameson et al. (1994) Nature 368:744; and Brady et al. (1994) Nature 368:692).

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:1); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila Antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:2); Transportan GWTLN-SAGYLLGKINLKALAALAKKIL (SEQ ID NO:3); KALAWEAKLAKALAKALAKHLAKALAKALKCEA (SEQ ID NO:4); and RQIKIWFQNRRMKWKK (SEQ ID NO:5). Exemplary PTDs include, but are not limited to, YGRKKRRQRRR (SEQ ID NO:1), RKKRRQRRR (SEQ ID NO:6); an arginine homopolymer of from 3 arginine residues to 50 arginine residues; exemplary PTD domain amino acid sequences include, but are not limited to, any of the following: YGRKKRRQRRR (SEQ ID NO:1); RKKRRQRR (SEQ ID NO:7); YARAAARQARA (SEQ ID NO:8); THRLPRRRRRR (SEQ ID NO://9); and GGRRAR-RRRRR (SEQ ID NO:10).

The carboxyl group $COR_3$ of the amino acid at the C-terminal end of an IL-10 polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of an IL-10 polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic IL-10 Function

It is frequently beneficial, and sometimes imperative, to improve one of more physical properties of the treatment modalities disclosed herein (e.g., IL-10) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications may also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of IL-10 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

In addition to the beneficial effects of pegylation on pharmacokinetic parameters, pegylation itself may enhance activity. For example, PEG-IL-10 has been shown to be more efficacious against certain cancers than unpegylated IL-10 (see, e.g., EP 206636A2). Certain embodiments of the present disclosure contemplate the use of a relatively small PEG (e.g., 5 kDa) that improves the pharmacokinetic profile of the IL-10 molecule without causing untoward adverse effects; such PEG-IL-10 molecules are especially efficacious for chronic use.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography may be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-10 and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the nucleic acid level, particularly by mutating the nucleic acid encoding the polypeptide at preselected bases such that codons are generated that will translate into the desired amino acids.

Polysialylation:

The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics.

Albumin Fusion:

Additional suitable components and molecules for conjugation include albumins such as human serum albumin (HSA), cyno serum albumin, and bovine serum albumin (BSA).

According to the present disclosure, albumin may be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701).

In the HSA-drug molecule conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences.

Alternative Albumin Binding Strategies:

Several albumin-binding strategies have been developed as alternatives to direct fusion and may be used with the IL-10 agents described herein. By way of example, the present disclosure contemplates albumin binding through a conjugated fatty acid chain (acylation) and fusion proteins which comprise an albumin binding domain (ABD) polypeptide sequence and the sequence of one or more of the polypeptides described herein.

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

An IL-10 polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of IL-10 to improve one or more properties. One such method involves modification of the polypeptide sequences by hesylation, which utilizes hydroxyethyl starch derivatives linked to other molecules in order to modify the polypeptide sequences' characteristics. Various aspects of hesylation are described in, for example, U.S. Patent Appln. Nos. 2007/0134197 and 2006/0258607.

The present disclosure also contemplates fusion molecules comprising Small Ubiquitin-like Modifier (SUMO) as a fusion tag (LifeSensors, Inc.; Malvern, Pa.). Fusion of a polypeptide described herein to SUMO may convey several beneficial effects, including enhancement of expression, improvement in solubility, and/or assistance in the development of purification methods. SUMO proteases recognize the tertiary structure of SUMO and cleave the fusion protein at the C-terminus of SUMO, thus releasing a polypeptide described herein with the desired N-terminal amino acid.

The present disclosure also contemplates the use of PASylation™ (XL-Protein GmbH (Freising, Germany)). This technology expands the apparent molecular size of a protein of interest, without having a negative impact on the therapeutic bioactivity of the protein, beyond the pore size of the renal glomeruli, thereby decreasing renal clearance of the protein.

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Exemplary flexible linkers include glycine polymers $(G)_n$, glycine-serine polymers (for example, $(GS)_n$, $GSGGS_n$, $GGGS_n$, $(G_mS_o)_n$, $(G_mS_oG_m)_n$, $(G_mS_oG_mS_oG_m)_n$, $(GSGGS_m)_n$, $(GSGS_mG)_n$ and $(GGGS_m)_n$, and combinations thereof, where m, and and o are each independently selected from an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG, GGSGG, GSGSG, GSGGG, GGGSG, and GSSSG.

Therapeutic and Prophylactic Uses

The present disclosure contemplates the use of the IL-10 polypeptides described herein (e.g., PEG-IL-10) in the treatment and/or prevention of diseases, disorders or conditions, and/or the symptoms thereof, relating to, or resulting from, for example, hypercholesterolemia, aberrant lipid profile, and other disorders associated, directly or indirectly, with cholesterol homeostasis. While particular uses are described in detail hereafter, it is to be understood that the present disclosure is not so limited. In addition, although specific categories of exemplary diseases, disorders and conditions associated with, or resulting from, hypercholesterolemia and aberrant lipid profile are discussed hereafter, it is to be understood that there is often overlap between one or more categories (e.g., certain cardiovascular diseases may have an inflammatory component).

Cardiovascular Diseases.

In particular embodiments, the present disclosure contemplates the use of the IL-10 polypeptides (e.g., PEG-IL-10) described herein to treat and/or prevent cardiovascular diseases, disorders and conditions, as well as disorders associated therewith, resulting from hypercholesterolemia and aberrant lipid profile.

As used herein, the terms "cardiovascular disease", "heart disease" and the like refer to any disease that affects the cardiovascular system, primarily cardiac disease, vascular diseases of the brain and kidney, and peripheral arterial diseases. Cardiovascular disease is a constellation of diseases that includes coronary heart disease (e.g., ischemic heart disease or coronary artery disease), atherosclerosis, cardiomyopathy, hypertension, hypertensive heart disease, cor pulmonale, cardiac dysrhythmias, endocarditis, cerebrovascular disease, and peripheral arterial disease. Cardiovascular disease is the leading cause of deaths worldwide, and while it usually affects older adults, the antecedents of cardiovascular disease, notably atherosclerosis, begin in early life.

Particular embodiments of the present disclosure are directed to the use of the IL-10 polypeptides described herein to treat and/or prevent atherosclerosis, a chronic condition in which an arterial wall thickens due to formation of plaques as a result of the accumulation of fatty materials such as cholesterol and triglycerides. As discussed further herein, atherosclerosis frequently involves a chronic inflammatory response in the walls of arteries, caused largely by the accumulation of macrophages and promoted by LDLs without adequate removal of fats and cholesterol from the macrophages by functional HDLs. Chronically expanding atherosclerotic lesions can cause complete closure of the lumen, which may only manifest when the lumen stenosis is so severe that blood supply to downstream tissue(s) is insufficient, resulting in ischemia.

Particularly contemplated by the present disclosure are embodiments wherein the cardiovascular disease comprises a hyperlipidemia (or hyperlipoproteinemia), conditions characterized by abnormally elevated levels of lipids and/or lipoproteins in the blood. Hyperlipidemias may be classified as familial (or primary) when caused by specific genetic abnormalities, acquired (or secondary) when resulting from another underlying disorder, or idiopathic, when of unknown cause. Hyperlipidemias may also be classified based on which types of lipids and/or lipoproteins are elevated. Non-limiting examples of hyperlipidemias include dyslipidemia, hypercholesterolemia, hyperglyceridemia, hypertriglyceridemia, hyperlipoproteinemia, hyperchylomicronemia, and combined hyperlipidemia. Hyperlipoproteinemias include, for example, hyperlipoproteinemia type Ia, hyperlipoproteinemia type Ib, hyperlipoproteinemia type Ic, hyperlipoproteinemia type IIa, hyperlipoproteinemia type IIb, hyperlipoproteinemia type III, hyperlipoproteinemia type IV, and hyperlipoproteinemia type V.

In particular embodiments, the present disclosure contemplates the treatment and/or prevention of familial hypercholesterolemia (FH), a genetic disorder characterized by very high levels of LDL in the blood. FH is associated with early cardiovascular disease, as accelerated deposition of cholesterol in the arterial walls leads to atherosclerosis. In certain patient populations, total cholesterol levels range from 350-550 mg/dL, while in other patient populations they range from of 650-1000 mg/dL. In obese patients having FH, cholesterol levels can be dramatically higher.

Attempts to treat cardiovascular disease by controlling levels of lipids and/or lipoproteins in the blood have met with limited success. For example, although administration of statins reduces cardiovascular risk in some individuals, these therapeutic compounds do not reduce triglyceride levels. In individuals at cardiovascular risk who exhibit deleteriously high levels of triglycerides, a member of the fibrate class of therapeutic agents may be administered. However, although lowering triglyceride and LDL levels, fibrates do not affect HDL levels. Moreover, combination treatments involving statins and fibrates, while sometimes effective, often cause a significant increase in the risk of myopathy and rhabdomyolysis, and therefore can only be carried out under very close medical supervision. In view of limitations as exemplified above, there is clearly a need for improved agents for the use and treatment of cardiovascular diseases, including those associated with high lipid and/or lipoprotein levels.

Thrombosis and Thrombotic Conditions.

In other embodiments, the present disclosure contemplates the use of the IL-10 polypeptides (e.g., PEG-IL-10) described herein to treat and/or prevent thrombosis and thrombotic diseases, disorders and conditions, as well as disorders associated therewith, resulting from hypercholesterolemia and aberrant lipid profile. Thrombosis, the formation of a thrombus inside a blood vessel resulting in obstruction of the flow of blood through the circulatory system, may be caused by abnormalities in one or more of the following (Virchow's triad): hypercoagulability or increased blood clotting, endothelial cell injury, or disturbed blood flow (stasis, turbulence).

Thrombosis is generally categorized as venous or arterial, each of which can be presented by several subtypes. Venous thrombosis includes deep vein thrombosis (DVT), portal vein thrombosis, renal vein thrombosis, jugular vein thrombosis, Budd-Chiari syndrome, Paget-Schroetter disease, and cerebral venous sinus thrombosis. Arterial thrombosis includes stroke and myocardial infarction.

Inflammatory Disorders.

When cholesterol and/or LDL become embedded in the walls of blood vessels, an immune response can be triggered, which, in turn, results in chronic inflammation. In response to this inflammation, blood monocytes adhere to the endothelium, transmigrate into the subendothelial space, and differentiate toward macrophages. Macrophages, in turn, engulf the cholesterol deposits and modified LDL by phagocytosis via scavenger receptors, which are distinct from LDL receptors. However, the adaptive mechanisms mediated by macrophages are not sufficient to process the uncontrolled cholesterol and/or LDL deposition seen under pathologic conditions. As a result, the lipid-laden macrophages transform into "foam cells", often accompanied by release of inflammation-inducing molecules. Both cholesterol/LDL deposition and the attendant foam cell-mediated pro-inflammatory reactions in the walls of the blood vessels lead to the development of atherosclerotic lesions. Thus, one consequence of modulating the levels of a lipid or lipoprotein is the reduction or elimination of a chronic inflammation.

The present disclosure includes embodiments wherein the IL-10 agents described herein (e.g., PEG-IL-10) are used in the treatment and/or prevention of a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect arteries and/or veins, regardless of size. It may be focal or widespread, with areas of inflammation scattered throughout a particular organ or tissue, or even affecting more than one organ system in the body. Vasculitis includes, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, thrombophlebitis, Wegener's granulomatosis; and vasculitis secondary to connective tissue disorders like systemic lupus erythematosus, rheumatoid arthritis, relapsing polychondritis, Behcet's disease, or other connective tissue disorders; and vasculitis secondary to viral infection.

Other embodiments are directed to an inflammatory heart disease, which refers to a condition characterized by inflammation of the heart muscle and/or the surrounding tissue. Examples include, but are not limited to, endocarditis, inflammatory cardiomegaly, and myocarditis.

Fibrotic Disorders:

The present disclosure also provides methods of treating or preventing fibrotic diseases, disorders and conditions. As used herein, the phrase "fibrotic diseases, disorders and conditions", and similar terms (e.g., "fibrotic disorders") and phrases, is to be construed broadly such that it includes any condition which may result in the formation of fibrotic tissue or scar tissue (e.g., fibrosis in one or more tissues). By way of example, injuries (e.g., wounds) that may give rise to scar tissue include wounds to the skin, eye, lung, kidney, liver, central nervous system, and cardiovascular system. The phrase also encompasses scar tissue formation resulting from stroke, and tissue adhesion, for example, as a result of injury or surgery.

As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue.

Fibrotic disorders include, but are not limited to, fibrosis arising from wound healing, systemic and local scleroderma, atherosclerosis, restenosis, pulmonary inflammation and fibrosis, idiopathic pulmonary fibrosis, interstitial lung disease, liver cirrhosis, fibrosis as a result of chronic hepatitis B or C infection, kidney disease (e.g., glomerulonephritis), heart disease resulting from scar tissue, keloids and hypertrophic scars, and eye diseases such as macular degeneration, and retinal and vitreal retinopathy. Additional fibrotic diseases include chemotherapeutic drug-induced fibrosis, radiation-induced fibrosis, and injuries and burns.

Fibrotic disorders are often hepatic-related, and there is frequently a nexus between such disorders and the inappropriate accumulation of liver cholesterol and triglycerides within the hepatocytes and Kupffer cells. This accumulation appears to result in a pro-inflammatory response that leads to liver fibrosis and cirrhosis. Hepatic disorders having a fibrotic component include non-alcoholic fatty liver disease (NAFLD) and non-alcoholic steatohepatitis (NASH). NAFLD occurs when steatosis (fat deposition in the liver) is present that is not due to excessive alcohol use. It is related to insulin resistance and the metabolic syndrome. NASH is the most extreme form of NAFLD, and is regarded as a major cause of cirrhosis of the liver of unknown cause.

Pharmaceutical Compositions

The IL-10 polypeptides of the present disclosure may be in the form of compositions suitable for administration to a subject. In general, such compositions are "pharmaceutical compositions" comprising IL-10 and one or more pharmaceutically acceptable or physiologically acceptable diluents, carriers or excipients. In certain embodiments, the IL-10 polypeptides are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present disclosure.

The pharmaceutical compositions typically comprise a therapeutically effective amount of an IL-10 polypeptide contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver IL-10, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. In particular embodiments, an active ingredient of an agent co-administered with an IL-10 agent described herein is in a form suitable for oral use. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the IL-10 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IL-10 polypeptides contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of IL-10 (e.g., IL-10 polypeptide), and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, may also be utilized to release the IL-10 polypeptides disclosed herein over a defined period of time.

Particular embodiments of the present disclosure contemplate parenteral administration. In some particular embodiments, the parenteral administration is intravenous, and in other particular embodiments the parenteral administration is subcutaneous.

Combination Therapy

The present disclosure contemplates the use of IL-10 (e.g., PEG-IL-10) in combination with one or more active therapeutic agents or other prophylactic or therapeutic modalities (e.g., radiation). In such combination therapy, the various active agents frequently have different mechanisms of action than IL-10. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

In particular embodiments, the present disclosure provides methods for treating and/or preventing diseases, disorders or conditions associated with (either directly or indirectly) cholesterol homeostasis, including associated cardiovascular, thrombotic and inflammatory disorders, with the IL-10 polypeptides described herein (e.g., PEG-IL-10) and at least one additional therapeutic or diagnostic agent. It is to be understood that combination therapy is not limited to agents that treat and/or prevent the aforementioned diseases, disorders and conditions; for example, agents contemplated for use in combination with the IL-10 polypeptides may have efficacy in treating or preventing other metabolic disorders, such as diabetes or obesity. Use of the IL-10 polypeptides (e.g., PEG-IL-10) in combination with modified diets and/or exercise regimens is also contemplated herein.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IL-10 polypeptides are administered or applied sequentially, e.g., where one agent is administered prior to one or more other agents. In other embodiments, the IL-10 polypeptides are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The IL-10 polypeptides of the present disclosure may be used in combination with at least one active agent in any manner appropriate under the circumstances. In one embodiment, treatment with the at least one active agent and at least one IL-10 polypeptide (i.e., homodimer) of the present disclosure is maintained over a period of time. In another embodiment, treatment with the at least one active agent is reduced or discontinued (e.g., when the subject is stable), while treatment with the IL-10 polypeptide of the present disclosure is maintained at a constant dosing regimen. In a further embodiment, treatment with the at least one active agent is reduced or discontinued (e.g., when the subject is stable), while treatment with the IL-10 polypeptide of the present disclosure is reduced (e.g., lower dose, less frequent dosing or shorter treatment regimen). In yet another embodiment, treatment with the at least one active agent is reduced or discontinued (e.g., when the subject is stable), and treatment with the IL-10 polypeptide of the present disclosure is increased (e.g., higher dose, more frequent dosing or longer treatment regimen). In yet another embodiment, treatment with the at least one active agent is maintained and treatment with the IL-10 polypeptide of the present disclosure is discontinued or reduced (e.g., lower dose, less frequent dosing or shorter treatment regimen). In yet another embodiment, treatment with the at least one active agent and treatment with the IL-10 polypeptide of the present disclosure are discontinued or reduced (e.g., lower dose, less frequent dosing or shorter treatment regimen).

While particular agents suitable for use in combination with the IL-10 polypeptides (e.g., PEG-IL-10) disclosed herein are set forth hereafter, it is to be understood that the present disclosure is not so limited. Hereafter, certain agents are set forth in specific categories of exemplary diseases, disorders and conditions; however, it is to be understood that there is often overlap between one or more categories (e.g., certain agents may have both cardiovascular and anti-inflammatory effects).

Cholesterol Homeostasis Agents.

Particular embodiments of the present disclosure involve combinations of IL-10 polypeptides with agents associated with cholesterol homeostasis. Many of these agents target different pathways involving the absorption, synthesis, transport, storage, catabolism, and excretion of cholesterol, and are thus particularly useful candidates for combination therapy.

Examples of therapeutic agents useful in combination therapy for the treatment of hypercholesterolemia (and thus frequently atherosclerosis, for example) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduce triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the IL-10 polypeptides described herein include various supplements and herbs (e.g., garlic, policosanol, and guggul). Several classes of the aforementioned therapeutic agents are discussed further hereafter.

Particular embodiments of the present disclosure comprise an IL-10 agent in combination with a fibrate. Fibrates, a class of amphipathic carboxylic acids, may be used as anti-hyperlipidemic agents to decrease levels of, e.g., triglycerides and LDL, and to increase levels of HDL. Examples of suitable fibrates include, without limitation, Bezafibrate, Ciprofibrate, Clofibrate, Gemfibrozil, and Fenofibrate.

Further particular embodiments of the present disclosure comprise an IL-10 agent in combination with a HMG-CoA Reductase Inhibitor (a statin). HMG-CoA Reductase Inhibitors may lower LDL and/or cholesterol levels by inhibiting the enzyme HMG-CoA Reductase, which plays a central role in the production of cholesterol in the liver. To compensate for the decreased cholesterol availability, synthesis of hepatic LDL receptors is increased, resulting in increased clearance of LDL particles from the blood. Examples of suitable statins include, without limitation, Atorvastatin, Fluvastatin, Lovastatin, Pitavastatin, Pravastatin, Rosuvastatin, and Simvastatin. Combinations of IL-10 polypeptides with a statin are particularly contemplated herein.

Still further particular embodiments of the present disclosure comprise an IL-10 agent in combination with a niacin. Niacins may lower LDL levels by selectively inhibiting hepatic diacyglycerol acyltransferase-2; reducing triglyceride synthesis, and reducing VLDL secretion through a receptor HM74 and HM74A or GPR109A. A non-limiting use of a niacin is as an anti-hyperlipidemic agent to inhibit the breakdown of fats in adipose tissue. By blocking the breakdown of fats, a niacin causes a decrease in free fatty acids in the blood and, as a consequence, decreases the secretion of VLDL and cholesterol by the liver. By lowering VLDL levels, a niacin may also increase the level of HDL in blood. Examples of suitable niacins include, without limitation, acipimox, niacin, nicotinamide, and vitamin B3.

Other particular embodiments of the present disclosure comprise an IL-10 agent in combination with a bile acid sequestrant. Bile acid sequestrants (also known as resins) bind certain components of bile in the gastrointestinal tract, thereby disrupting the enterohepatic circulation of bile acids by sequestering them and preventing their reabsorption from the gut. Bile acid sequestrants are particularly effective for lowering LDL and cholesterol, and may also raise HDL levels. Examples of suitable bile acid sequestrants include, without limitation, Cholestyramine, Colesevelam, and Colestipol.

Additional particular embodiments of the present disclosure comprise an IL-10 agent in combination with a cholesterol absorption inhibitor. Cholesterol absorption inhibitors decrease absorption of cholesterol from the intestine; this leads to up-regulation of LDL-receptors on the surface of cells and increased LDL cholesterol uptake into these cells, thus decreasing levels of LDL in the blood plasma. Examples of suitable cholesterol absorption inhibitors include, without limitation, ezetimibe, a phytosterol, a sterol and a stanol. Combinations of IL-10 polypeptides with ezetimibe are particularly contemplated herein. Ezetimibe selectively blocks cholesterol absorption and lowers plasma LDL levels by an average of 18%. When ezetimibe is co-administered with lower doses of statins, there is an additive reduction in LDL levels, which equals the reduction achieved with maximal doses of statins alone. Reduction in the statin dose results in fewer statin-related adverse effects.

Still further particular embodiments of the present disclosure comprise an IL-10 agent in combination with a fat absorption inhibitor. Fat absorption inhibitors decrease the absorption of fat from the intestine, thereby reducing caloric intake. In one aspect, a fat absorption inhibitor inhibits pancreatic lipase, an enzyme that breaks down triglycerides in the intestine. Examples of suitable fat absorption inhibitors include, without limitation, Orlistat.

In still other particular embodiments, the present disclosure contemplates use of the PEG-IL-10 agents described herein in combination with modulators of PCSK9 (Proprotein convertase subtilisin/kexin type 9). PCSK9 plays a major regulatory role in cholesterol homeostasis. It is a serine protease expressed predominantly in the liver, intestine and kidney. The encoded protein is synthesized as a soluble zymogen that undergoes autocatalytic intramolecular processing in the endoplasmic reticulum.

As part of the cholesterol homeostasis process, LDL cholesterol is removed from the blood when it binds to LDL receptors (LDLR) on the surface of liver cells and is taken up by such cells. PCSK9 functions by binding to LDLR and inducing receptor degradation, thereby preventing LDLR recycling to the cell surface to remove more LDL cholesterol, ultimately resulting in decreased metabolism thereof. Preventing PCSK9 binding to LDLR allows the receptor to return to the cell surface and remove more cholesterol.

Inhibitors of PCSK9 function have been shown to cause much more cholesterol lowering than traditional commercially available agents, with an acceptable adverse effect profile. The present disclosure contemplates the use of PEG-IL-10 with any modulator having a direct or indirect inhibitory effect on PCSK9. Several monoclonal antibodies that bind to PCSK9 and interfere with its interaction with the LDLR are being developed (e.g., by Amgen (AMG145), Merck (1D05-IgG2) and Aventis/Regeneron (SAR236553/REGN727)). In addition, peptides that mimic the EGFA domain of the LDLR that binds to PCSK9 are being developed, and gene silencing through the administration of a PCSK9 antisense oligonucleotide (ISIS Pharmaceuticals) has been shown to increase expression of the LDLR and decrease circulating total cholesterol levels in mice. Other modulators of PCSK9 function contemplated for combination therapy with the PEG-IL-10 agents described herein are those which act by means of RNA interference (RNAi) (Alnylam Pharmaceuticals) and as a locked nucleic acid (LNA) (Santaris Pharma), also referred to as inaccessible RNA.

The present disclosure encompasses pharmaceutically acceptable salts, acids or derivatives of any of the above.

Immune and Inflammatory Conditions.

The present disclosure provides methods for treating and/or preventing immune- and/or inflammatory-related diseases, disorders and conditions, as well as disorders associated therewith, with an IL-10 polypeptide (e.g., PEG-IL-10) and at least one additional agent having immune- and/or inflammatory-related properties. By way of example, an IL-10 polypeptide may be administered with an agent having efficacy in a cardiovascular disorder having an inflammatory component.

Examples of therapeutic agents useful in combination therapy include, but are not limited to, non-steroidal anti-inflammatory drugs (NSAIDs). NSAIDs, a large group of therapeutic compounds with analgesic, anti-inflammatory, and anti-pyretic properties, reduce inflammation by blocking cyclooxygenase. Examples of such agents include ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen); acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac); fenamic acid derivatives (flufenamic acid, meclofenamic acid, mefenamic acid, niflumic acid and tolfenamic acid); biphenylcarboxylic acid derivatives (diflunisal and flufenisal); oxicams (isoxicam, piroxicam, sudoxicam and tenoxican); salicylates (acetyl salicylic acid, sulfasalazine); and the pyrazolones (apazone, bezpiperylon, feprazone, mofebutazone, oxyphenbutazone, phenylbutazone).

Other combinations include selective cyclooxygenase-2 (COX-2) inhibitors, selective cyclooxygenase 1 (COX 1) inhibitors, and non-selective cyclooxygenase (COX) inhibitors. Particular embodiments of the present disclosure contemplate the IL-10 polypeptides described herein (e.g., PEG-IL-10) in combination with a suitable selective COX-2 inhibitor(s), such as Celecoxib, Etoricoxib, Firocoxib, Lumiracoxib, Meloxicam, Parecoxib, Rofecoxib, and Valdecoxib.

Other active agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by decreasing the steroid dose required when treating patients in combination with the present IL-10 polypeptides.

Additional examples of active agents for combinations for treating, for example, rheumatoid arthritis include cytokine suppressive anti-inflammatory drug(s) (CSAIDs); antibodies to or antagonists of other human cytokines or growth factors, for example, TNF, LT, IL-1β, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists like chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFα converting enzyme (TACE) inhibitors; similarly IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IL-10 polypeptides described herein include interferon-β1a (AVONEX); interferon-β1b (BETASERON); copaxone; hyperbaric oxygen; intravenous immunoglobulin; clabribine; and antibodies to or antagonists of other human cytokines or growth factors (e.g., antibodies to CD40 ligand and CD80).

The present disclosure encompasses pharmaceutically acceptable salts, acids or derivatives of any of the above.

Anti-Diabetic and Anti-Obesity Agents.

Some patients requiring pharmacological treatment for a cholesterol-related disorder(s) are also taking anti-diabetic and/or anti-obesity agents. The present disclosure contemplates combination therapy with numerous anti-diabetic agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, glycogen synthase kinase-3 inhibitors, immune modulators, beta-3 adrenergic receptor agonists, 11beta-HSD1 inhibitors, and amylin analogues. In still other embodiments, the IL-10 agents described herein are used in combination with one or more suitable nuclear receptor binding agents (e.g., a Retinoic Acid Receptor (RAR) binding agent, a Retinoid X Receptor (RXR) binding agent, a Liver X Receptor (LXR) binding agent and a Vitamin D binding agent).

Furthermore, the present disclosure contemplates combination therapy with agents and methods for promoting weight loss, such as agents that stimulate metabolism or decrease appetite, and modified diets and/or exercise regimens to promote weight loss.

The present disclosure encompasses pharmaceutically acceptable salts, acids or derivatives of any of the above.

Dosing

The IL-10 polypeptides of the present disclosure may be administered to a subject in an amount that is dependent upon, for example, the goal of the administration (e.g., the degree of resolution desired); the age, weight, sex, and health and physical condition of the subject; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IL-10 polypeptides of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

When an IL-10 polypeptide is PEG-IL-10, the amount of PEG-IL-10 necessary to treat a disease, disorder or condition described herein is based on the IL-10 activity of the conjugated protein, which, as indicated above, can be determined by IL-10 activity assays known in the art. By way of example, in the tumor context, suitable IL-10 activity includes, for example, CD8+ T-cell infiltrate into tumor sites, expression of inflammatory cytokines, such as IFN-γ, IL-4, IL-6, IL-10, and RANK-L, from these infiltrating cells, and increased levels of TNF-α or IFN-γ in biological samples.

Like many drugs, intravenous IL-10 administration is associated with a two-compartment kinetic model (see Rachmawati, H. et al. (2004) Pharm. Res. 21(11):2072-78). Plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. The pharmacokinetics of subcutaneous recombinant hIL-10 has also been studied (Radwanski, E. et al. (1998) Pharm. Res. 15(12):1895-1901). Volume-of-distribution and other pharmacokinetic considerations are pertinent when assessing appropriate IL-10 dosing-related parameters. Moreover, the leveraging of IL-10 pharmacokinetic and dosing principles may prove invaluable to the success of efforts to target IL-10 agents to specific cell types (see, e.g., Rachmawati, H. (May 2007) Drug Met. Dist. 35(5):814-21).

The present disclosure contemplates administration of any dose and dosing regimen that results in the desired therapeutic outcome. By way of example, but not limitation, when the subject is a human, non-pegylated hIL-10 may be administered at a dose greater than 0.5 µg/kg/day, greater than 1.0 µg/kg/day, greater than 2.5 µg/kg/day, greater than 5 µg/kg/day, greater than 7.5 µg/kg, greater than 10.0 µg/kg, greater than 12.5 µg/kg, greater than 15 µg/kg/day, greater than 17.5 µg/kg/day, greater than 20 µg/kg/day, greater than 22.5 µg/kg/day, greater than 25 µg/kg/day, greater than 30 µg/kg/day, or greater than 35 µg/kg/day. In addition, by way of example, but not limitation, when the subject is a human, pegylated hIL-10 comprising a relatively small PEG (e.g., 5 kDa mono-di-PEG-hIL-10) may be administered at a dose greater than 0.5 µg/kg/day, greater than 0.75 µg/kg/day, greater than 1.0 µg/kg/day, greater than 1.25 µg/kg/day, greater than 1.5 µg/kg/day, greater than 1.75 µg/kg/day, greater than 2.0 µg/kg/day, greater than 2.25 µg/kg/day, greater than 2.5 µg/kg/day, greater than 2.75 µg/kg/day, greater than 3.0 µg/kg/day, greater than 3.25 µg/kg/day, greater than 3.5 µg/kg/day, greater than 3.75 µg/kg/day, greater than 4.0 µg/kg/day, greater than 4.25 µg/kg/day, greater than 4.5 µg/kg/day, greater than 4.75 µg/kg/day, or greater than 5.0 µg/kg/day.

The therapeutically effective amount of PEG-IL-10 can range from about 0.01 to about 100 µg protein/kg of body weight/day, from about 0.1 to 20 µg protein/kg of body weight/day, from about 0.5 to 10 µg protein/kg of body weight/day, or from about 1 to 4 µg protein/kg of body weight/day. In some embodiments, PEG-IL-10 is administered by continuous infusion to delivery about 50 to 800 µg protein/kg of body weight/day (e.g., about 1 to 16 µg protein/kg of body weight/day of PEG-IL-10). The infusion rate may be varied based on evaluation of, for example, adverse effects and blood cell counts.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the disclosed IL-10 polypeptide (e.g., PEG-IL-10) is contained in a "unit dosage form". The phrase "unit dosage form" refers to physically discrete units, each unit containing a predetermined amount of a IL-10 polypeptide of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising IL-10 polypeptides (e.g., PEG-IL-10), and pharmaceutical compositions thereof. The kits are generally in the form of a physical structure housing various components, as described below, and may be utilized, for example, in practicing the methods described above (e.g., administration of an IL-10 polypeptide to a subject in need of restoring cholesterol homeostasis).

A kit can include one or more of the IL-10 polypeptides disclosed herein (provided in, e.g., a sterile container), which may be in the form of a pharmaceutical composition suitable for administration to a subject. The IL-10 polypeptides can be provided in a form that is ready for use or in a form requiring, for example, reconstitution or dilution prior to administration. When the IL-10 polypeptides are in a form that needs to be reconstituted by a user, the kit may also include buffers, pharmaceutically acceptable excipients, and the like, packaged with or separately from the IL-10 polypeptides. When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; wt=wildtype; HPLC=high performance liquid chromatography; BW=body weight; U=unit; ns=not statistically significant; PBS=phosphate-buffered saline; PCR=polymerase chain reaction; NHS=N-Hydroxysuccinimide; Cl=clodronate; HSA=human serum albumin; MSA=mouse serum albumin; IHC=immunohistochemistry; DMEM=Dulbeco's Modification of Eagle's Medium; GC=genome copy; EDTA=ethylenediaminetetraacetic acid; PCSK9=Proprotein convertase subtilisin/kexin type 9; CYP7A1=cytochrome P450 7A1, cholesterol 7 alpha-hydroxylase, or cholesterol 7-alpha-monooxygenase; ABCG1=ATP-binding cassette sub-family G member 1; MSR1=Macrophage Scavenger Receptor 1.

Materials and Methods

The following general materials and methods were used, where indicated, or may be used in the Examples below:

Standard methods in molecular biology are described in the scientific literature (see, e.g., Sambrook and Russell (2001) Molecular Cloning, 3$^{rd}$ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., N.Y.).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., N.Y.); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

Normalized mRNA units may be determined by relative quantification whereby changes in gene expression in a sample are calculated based on gene expression in a reference sample.

Mice:

LDLR−/− mice were obtained from The Jackson Lab (Bar Harbor, Me.). LDLR−/− mice have an elevated serum cholesterol level of 200-400 mg/dl, and their cholesterol level averages ~1,500 mg/dL when fed a high fat diet. Normal serum cholesterol in the mouse is 80-100 mg/dl.

Serum IL-10 Concentrations:

For the experiments described herein, concentrations of test materials in serum samples were determined via an electrochemiluminescence assay for mIL-10 on the MDS platform. LCB-33AEY (ARMO) anti-MIL-10 was used as the capture and biotinylated anti-MIL-10 (R&D) was used as the detection antibody. A PEG-rMuIL-10 standard curve was set up with the upper and lower limits of 195,000 pg-9 pg. Plates were incubated for 2 hours at room temperature, and after washing detected via the SulfoTag program on an MSD 2400 platform.

Alternatively, serum IL-10 concentration levels and exposure levels may be determined by other standard methods used in the art. For example, a serum exposure level assay can be performed by collecting whole blood (~50 µl/mouse) from mouse tail snips into plain capillary tubes, separating serum and blood cells by centrifugation, and determining IL-10 exposure levels by standard ELISA kits and techniques.

Serum and Tissue Cholesterol Quantitation:

Methodology No. 1:

Serum was analyzed at a 1:300 dilution. Mouse livers were ground up in 200 µL water with pestles (VWR). Twenty-five microliter aliquots were used for the extraction of cholesterol/cholesteryl esters using a cholesterol/cholesteryl assay kit (BioVision) according to the manufacturer's instructions and measured with a Spectra Max 340 PC (Molecular Devices). Genomic DNA was extracted from equal amounts of sample using a DNeasy kit (QIAGEN) and measured with a NanoVue Plus (GE Healthcare) to normalize the cholesterol/cholesteryl measurements.

Methodology No. 2:

Serum LDL-C or HDL-C quantitation was performed on a Beckman Coulter AU System LDL-Cholesterol test using a two reagent homogenous system. The assay is comprised of two distinct phases. In Phase 1, a unique detergent solubilizes cholesterol from non-LDL-lipoprotein or non-HDL-particles, depending on the desired assay output. This cholesterol is consumed by cholesterol esterase, cholesterol oxidase, peroxides, and 4 aminoantipyrine (LDL-C) or DSBmT (HDL-C) to generate a colorless end product. In Phase 2, a second detergent in the R2 reagent releases cholesterol from the remaining lipoproteins. This cholesterol reacts with cholesterol esterase, cholesterol oxidase, and a chromogen system to yield a blue color complex which can be measured bichromatically at 540/660 nm. The resulting increase in absorbance is directly proportional to the LDL-C or HDL-C concentration in the sample.

qPCR Analysis:

Livers were excised from mice at necropsy and flash-frozen for subsequent analysis. Mouse livers were ground up in Buffer RLT (QIAGEN) with 10 µL β-mercaptoethanol (Sigma-Aldrich) using pestles (VWR), after which RNA was extracted using an RNeasy kit (QIAGEN) according to the manufacturer's instructions. The purified RNA was used as template for RT-PCR using an RT2 First Strand kit (QIAGEN). One microliter aliquots of the resulting cDNA samples were used for qPCR of the indicated transcripts on an ABI PRISM 7700 Sequence Detection System or an ABI ViiA 7 Real Time PCR Machine (Life Technologies). CT values were normalized to the average CT value of Gapdh and Gusb.

Tissue Triglyceride Quantitation:

Mouse livers were ground up in 200 µL water with pestles (VWR). Twenty-five microliter aliquots were used for the extraction of triglycerides using a Triglyceride Assay kit (Biovision) according to the manufacturer's instructions and measured with a Spectra Max 340 PC (Molecular Devices). Protein concentration was determined using the Pierce BCA protein assay (Thermo Scientific) according to the manufacturer's instructions and measured with a Spectra Max 340 PC.

Immunohistochemistry:

Picosirius Red Stain:

Slides were heated in an oven at 60° C. for 45 mins, de-paraffinized using xylene and series of alcohols, and rehydrated in water; then kept for 60 mins in freshly-prepared Picosirius red solution according to manufacturer's instructions, followed by two washes in acidified water. Nuclei were stained with Weigert's hematoxylin for 8-10 mins, dehydrated in three changes of 100% ethanol, cleared, and mounted.

Hematoxylin and Eosin Stain:

Slides were de-paraffinized with two changes of xylene (10 mins each), dehydrated through absolute, 95%, 70% alcohols (5 mins each), and rehydrated in water. Slides were then placed in hematoxylin stain for 4 mins, rinsed in water, differentiated in 1% acid alcohol for 30 seconds, and stained in 0.01% Eosin Y for 2 sec, rinsed in 95% ethanol, dehydrated with absolute ethanol, and cleared in xylenes for 15 mins before cover slipping.

Anti-F4/80, Anti-Msr1, Anti-PCNA:

Liver tissues were fixed with 10% neutral-buffered formaldehyde and were embedded in paraffin. Tissue specimens were cut into 5-μm-thick sections, de-paraffinized in xylene sections, and hydrated in a graded series of alcohol solutions (100%, 95%, 80%, 70%, 50% (three changes, each of 5 mins)). The tissues on slides underwent heat-induced epitope retrieval (10 mmol/L sodium citrate buffer at 98° C. for 20 mins), then were treated with 3% $H_2O_2$ to quench endogenous peroxidase. Sections were incubated in blocking solution (5% neutral goat serum) for 1 hr at room temperature. Primary antibodies of choice were applied on the slides and incubated in humid chamber overnight at 4° C. Secondary biotinylated antibody was then applied at 1:250 dilution (Vector Lab, Burlingame, Calif., USA), followed by incubation with streptavidin peroxidase. Sections were washed with PBS three times after each step. Sections were stained with DAB substrate and counterstained with Mayer's hematoxylin for 2 mins. Slides were dehydrated in three changes of 100% ethanol, cleared, and mounted.

Image Quantitation:

For analysis of PEG-rMuIL-10-treated livers compared to vehicle-treated livers, 5-10 mice per group were randomly selected and stained with Sirius Red (Polyscience Inc.), TUNEL (Roche), anti-PCNA (Abcam), Hematoxylin (American MasterTech), anti-Msr1 (Abcam), anti-F4/80 (Abcam), or anti-CD68 (Serotech). For each liver, 8-10 independent images were collected using the 20×objective. An average area of signal was then analyzed using Meta-Morph Imaging Software (Molecular Devices) by applying a color threshold on a representative field and adjusting the pixel distribution to correspond with a positive signal.

In Vitro Uptake Assays:

Monocytes were isolated from Ficoll centrifugation-isolated peripheral blood mononuclear cells by Miltenyi magnetic bead positive selection. Cells were stimulated with or without PEG-rHuIL-10 for 24 hours in complete RPMI. $1 \times 10^6$ cells were analyzed for uptake of 20 μL DiLDL, OxLDL or AcLDL, (Alfa Aesar) in 4 hrs. Macrophages were differentiated from positively selected peripheral blood monocytes with 50 ng/mL M-CSF (BioLegend) in cRPMI for 7 days. Cells were re-plated at $0.3$-$0.4 \times 10^6$ cells per well in a 24-well plate and exposed to PEG-rHuIL-10 for 24 hrs. Cells were washed once and exposed to 20 μL DiLDL, OxLDL or AcLDL, (Alfa Aesar), where uptake was measured after 4 hrs. Human primary hepatocytes (Triangle Research Labs) and Kupffer cells (Invitrogen) were thawed and plated at $0.4 \times 10^6$ cells per well in 24-well plates and incubated overnight in hepatocyte incubation medium (phenol-red free RPMI, pen/strep, Cell Maintenance Supplement B (Invitrogen)) and complete RPMI, respectively. Cells were washed and exposed for 24 hrs to PEG-rHuIL-10. Thereafter, cells were washed once and exposed to 20 μL DiLDL, OxLDL or AcLDL, (Alfa Aesar), where uptake was measured after 4 hrs. All cells were washed once in 1×PBS and lysed with 110 μL cell lysis buffer (Sigma-Aldrich). Forty-five μL of cell lysis was transferred to clear bottom black-walled plates (Greiner Bio-One) where fluorescence was read at 575 nm.

In Vivo Studies:

Mouse studies were conducted at Aragen Biosciences (Morgan Hill, Calif.) in accordance with standard operating procedures and established guidelines approved by their Institutional Animal Care and Use Committee (IACUC).

Hypercholesterolemia Model:

In-life portions of the studies were performed at Aragen Biosciences. Wild-type and LDLR−/− C57BL/6 mice (7-8 weeks old) were maintained on normal chow or fed a Western diet for 2 or 7 weeks prior to dosing. PEGylated recombinant mouse IL-10 (PEG-rMuIL-10) or vehicle (10 mM HEPES, 100 mM NaCl, pH 6.5, 0.05% mouse serum albumin) was dosed SC daily for 2 to 3 weeks; mice were maintained on their respective diets throughout dosing. For clodronate depletion studies, mice were dosed IV every 3 days with clodronate liposomes (5 mg/mL clodronate) or vehicle liposomes (first dose: 0.2 mL, subsequent doses: 0.1 mL), starting one day before PEG-rMuIL-10 dosing.

Pegylation:

A mono-/di-PEG-IL-10 mix described in the patent literature (e.g., US 2011/0250163) was used in both preclinical and clinical analyses, and in the examples set forth hereafter. Two exemplary synthetic schemes are as follows:

Exemplary Scheme No. 1.

IL-10 (e.g., rodent or primate) is dialyzed against 50 mM sodium phosphate, 100 mM sodium chloride pH ranges 5-7.4. A 1:1-1:7 molar ratio of 5 kDa PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours. The pH of the pegylation reaction is adjusted to 6.3, and 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-PEG IL-10 are the largest products of the reaction, with the concentration of each at ~50% at termination. The reaction may be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

Exemplary Scheme No. 2.

IL-10 is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12 kDa (Delmar Scientific Laboratories, Maywood, Ill.) and one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate, and the reaction solution is mildly agitated. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C.

PEG-IL-10 was formulated at 0.75-1.0 mg/mL in 10 mM HEPES, pH 6.5, 100 mM NaCl containing 0.05% MSA. Control (placebo)=same formulation matrix without PEG-IL-10.

EXAMPLE 1

PEG-rMuIL-10 Lowers Plasma Cholesterol Levels

The regulatory effect of PEG-rMuIL-10 on plasma cholesterol levels in wild-type and LDLR−/− mice fed a normal and high fat diet was assessed.

Referring to FIGS. 1A-1C, wild-type mice on normal chow exhibited no decrease in total plasma cholesterol, LDL or HDL particles following administration of 1.0, 0.2, and 0.02 mg/kg PEG-rMuIL-10, or vehicle control, SC daily.

The effect of PEG-rMuIL-10 in LDLR−/− mice was then determined. When total plasma cholesterols levels reached approximately 200 mg/dL in both LDLR−/− mice on normal chow diet and wild-type mice on high-fat chow diet, 0.2 mg/kg PEG-rMuIL-10, 0.02 mg/kg PEG-rMuIL-10, or vehicle control were administered SC. Mice that received 0.2 mg/kg PEG-rMuIL-10 exhibited cholesterol reduction of 22% (FIG. 1D; LDLR−/− mice) and 25% (FIG. 1G; wt mice). Mice that received 0.2 mg/kg PEG-rMuIL-10 exhibited LDL-C reduction of 30% (FIG. 1E; LDLR−/− mice) and 15% (FIG. 1H; wt mice). Mice that received 0.2 mg/kg PEG-rMuIL-10 exhibited HDL-C reduction of 36% (FIG. 1F; LDLR−/− mice) and 45% (FIG. 1I; wt mice). LDLR−/− mice on a high fat chow diet that received 0.02 mg/kg PEG-rMuIL-10, SC daily for two weeks exhibited a total plasma cholesterol level reduction of nearly 50%, an LDL-C level reduction of 60%, and an HDL-C reduction of 35% (FIGS. 1J-L, respectively) when initial levels of cholesterol and LDL-C were higher. FIGS. 1A-1L also indicates the effect of 0.02 mg/kg PEG-rMuIL-10 on each of the aforementioned parameters. Lastly, longer dosing of the LDLR−/− mice on a high fat chow diet resulted in total plasma cholesterol reduction of up to 70% (data not show). Taken together, the results indicate that the lowering of plasma cholesterol with PEG-rMuIL-10 is dependent on total cholesterol levels.

Figure 1M:
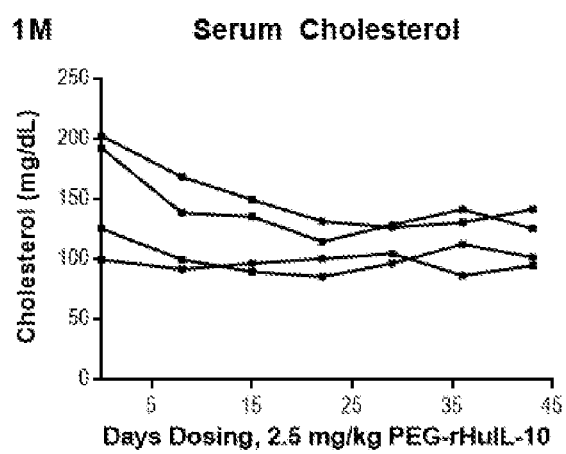
FIGS. 1M-1N illustrate the effect of PEG-rHuIL-10 on plasma cholesterol levels in oncology patients.
Figure 1N:
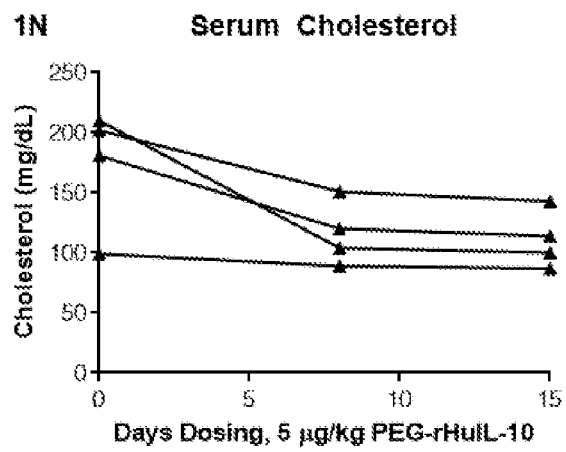

In order to confirm the findings set forth above, total plasma cholesterol was assessed in human patients (n=4) being treated for cancer (a mix of non-small cell lung carcinoma (NSCLC), renal cell carcinoma (RCC) and colorectal) with PEG-rHuIL-10. Patients were administered 2.5 μg/kg or 5 μg/kg PEG-rHuIL-10 SC daily. As indicated in FIG. 1M, administration of 2.5 μg/kg PEG-rHuIL-10 lowered cholesterol the most in patients with borderline-high (~200 mg/dL) total cholesterol; in this patient population, total plasma cholesterol was reduced by up to 40%, consistent with the mouse data discussed previously. Patients with low (~100 mg/dL) total cholesterol were unaffected by PEG-rHuIL-10, and patients with an initial plasma cholesterol concentration of ~140 mg/dL achieved cholesterol lowering to about 100 mg/dL. A level of 140 mg/dL or lower is consistent with no life time risk of a cardiovascular event. Administration of 5 μg/kg PEG-rHuIL-10 resulted in cholesterol reduction in a manner consistent with that observed when 2.5 μg/kg PEG-rHuIL-10 was adminstered, and the amount of reduction was also dependent on the patient's baseline cholesterol level (see FIG. 1N).

These data suggest that the mechanism by which PEG-IL-10 regulates serum cholesterol in mice is similar to that in humans.

EXAMPLE 2

PEG-rMuIL-10 Alters Liver Expression of Cholesterol Synthesis and Scavenger Receptor Genes Using the Qiagen Lipoprotein Signaling and Cholesterol Metabolism, Fibrosis and Innate & Adaptive Immune Response Panels, the effect of PEG-rMuIL-10 on the expression of genes associated with liver function and cholesterol regulation was evaluated. As illustrated in FIGS. 2A-2L, only two primary groups of genes were altered in response to PEG-rMuIL-10 exposure.

The first group of regulatory genes is involved in endogenous cholesterol synthesis. Wild-type mice on normal chow diet (FIG. 2A), LDLR−/− mice on normal chow diet (FIG. 2B), wild-type mice on high-fat chow diet (FIG. 2C), and LDLR−/− mice on high-fat chow diet (FIG. 2D), were administered 0.2 mg/kg PEG-rMuIL-10, 0.02 mg/kg PEG-rMuIL-10, or vehicle control, SC daily. Hmgcs1 and 2, two genes involved in endogenous cholesterol synthesis, were moderately but consistently decreased in the liver (FIGS. 2A-D). These data are consistent with reports that IL-10 may decrease endogenous cholesterol synthesis by inhibiting Mevalonate Pathway.

The second group of regulatory genes comprises scavenger receptors. As indicated in FIGS. 2E-2L, all further comparisons focused on the differences between the vehicle control group and the group of mice administered 0.2 mg/kg PEG-rMuIL-10, as the group of mice administered 0.02 mg/kg PEG-rMuIL-10 exerted limited control on both plasma cholesterol control and gene regulation. Wild-type mice on normal chow diet (FIG. 2E), LDLR−/− mice on normal chow diet (FIG. 2F), wild-type mice on high-fat chow diet (FIG. 2G), and LDLR−/− mice on high-fat chow diet (FIG. 2H), were administered 0.2 mg/kg PEG-rMuIL-10 or vehicle control, SC daily. As indicated in FIGS. 2E-2H, Msr1 and Marco, Type A scavenger receptors, were induced by 2-7 fold. In order to expand the scavenger receptor analysis, expression differences in other receptors known to regulate serum cholesterol were assessed. LDL Receptor expression was not changed (data not shown) and is not relevant in the LDLR−/−, and expression of both CD36 and PCSK9 were also unchanged (see FIGS. 2E-2H). Because scavenger receptors are predominantly expressed on macrophage-type cells, differences in expression of F4/80 and CD14, two cell surface proteins most often expressed on liver tissue resident macrophages, were also assessed. These genes were moderately induced across the different genetic backgrounds and dietary conditions (see FIGS. 2E-2H). These data confirm the role of scavenger receptors in aspects of liver function and cholesterol regulation.

If PEG-rMuIL-10 induces an increase in the uptake of lipoproteins, there may be a concomitant increase in efflux-associated genes. Therefore, the levels of the efflux mediators ABCG1 and ABCA1 were evaluated. ABCG1 is considered to principally function in the liver, and ABCA1 is considered to primarily function in the gastrointestinal track. Both factors act as cholesterol efflux pumps to remove cholesterol from the interior of the cell onto lipid-poor HDL particles. Wild-type mice on normal chow diet (FIG. 2I), LDLR−/− mice on normal chow diet (FIG. 2J), wild-type mice on high-fat chow diet (FIG. 2K), and LDLR−/− mice on high-fat chow diet (FIG. 2L), were administered 0.2 mg/kg PEG-rMuIL-10, or vehicle control, SC daily. As depicted in FIGS. 2I-L, only ABCG1 exhibits a consistent, though moderate, trend of increased expression.

EXAMPLE 3

PEG-rMuIL-10 Alters Expression of Scavenger Receptors and the Presence of Kupffer Cells In order to evaluate whether PEG-rMuIL-10 increases both scavenger receptors and the number of KCs, treated and untreated liver tissue was analyzed for differences in MSR1 expression by IHC.

Figures 3A, 3B, 3C, 3D, 3E, 3F, 3G, 3H:
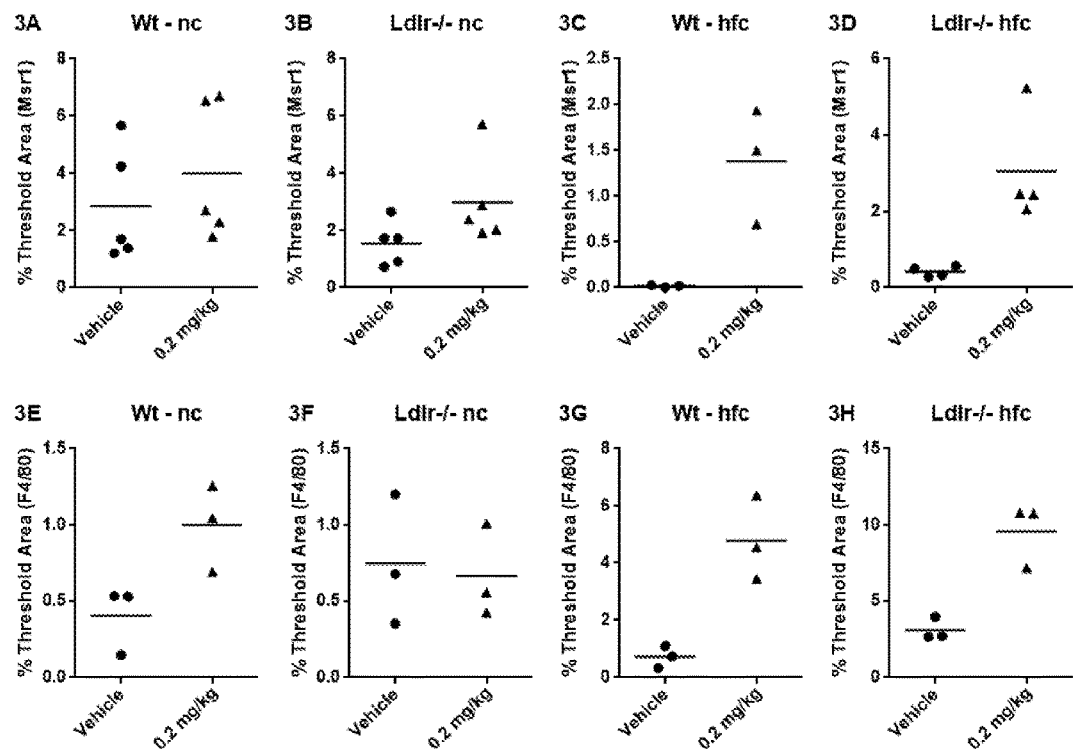
FIGS. 3A-3H illustrate the effect of PEG-rMuIL-10 on scavenger receptors and the number of Kupffer cells in treated and untreated liver tissue.

Wild-type mice on normal chow diet (FIG. 3A), LDLR−/− mice on normal chow diet (FIG. 3B), wild-type mice on high-fat chow diet (FIG. 3C), and LDLR−/− mice on high-fat chow diet (FIG. 3D), were administered 0.2 mg/kg PEG-rMuIL-10 or vehicle control, SC daily. As indicated in FIGS. 3A and 3B, dosing with PEG-rMuIL-10 led to a slight increase in detectible MSR1 in wt and LDLR−/− mice on the normal diet. However, MSR1 levels in control tissue appeared to decrease in conjunction with increased dietary fat intake. The levels of detectible MSR1 were higher in wt and LDLR−/− mice on normal chow relative to the same type of mice on high fat chow. This result was confirmed with the use of IHC to quantify the amount of Msr1 (FIGS. 3A-D). In addition, treatment with PEG-rMuIL-10 appeared to normalize levels of Msr1 within the liver tissue of LDLR−/− mice (data not shown).

Referring to FIGS. 2A-2L, scavenger receptors are most often expressed on macrophage lineage cells and an increase in message expression of F4/80 and CD14 was identified. Thus, wild-type mice on normal chow diet (FIG. 3E), LDLR−/− mice on normal chow diet (FIG. 3F), wild-type mice on high-fat chow diet (FIG. 3G), and LDLR−/− mice on high-fat chow diet (FIG. 3H) were administered 0.2 mg/kg PEG-rMuIL-10 or vehicle control, SC daily in order to assess the protein expression levels of F4/80 by IHC (data not shown). In wild type and LDLR−/− mice on normal chow, there was little-to-no difference in the presence of F4/80-positive cells (FIGS. 3E and F). However, in wild type and LDLR−/− on high fat chow, there was a detectible increase in F4/80-positive cells (FIGS. 3G and H), suggesting PEG-rMuIL-10 increases the number of Kupffer cells in the liver of animals with increased dietary fat uptake.

In addition, expression analysis of the IL-10Rα showed an approximate 2-fold difference in IL-10Rα message between wt and LDLR−/− mice on normal vs. high fat chow, suggesting that some of the difference in cholesterol regulation may be due to relative IL-10 receptor levels (data not shown).

EXAMPLE 4

In Vivo Depletion of Phagocytotic Cells Abolishes PEG-rMuIL-10 Reduction of Cholesterol An assessment was conducted in order to determine whether cells associated with the myeloid lineage were responsible for the control of plasma cholesterol by PEG-rMuIL-10.

A standard technique was used for removing phagocytotic cells by dosing animals with clodronate (Cl) liposomes in the presence or absence of PEG-rMuIL-10. After ensuring complete depletion of all phagocytotic cells in the liver and assessing hepatocyte health by IHC (data not shown), PEG-rMuIL-10 regulation of plasma cholesterol levels was evaluated in wild-type mice on normal chow diet (FIG. 4B), LDLR−/− mice on normal chow diet (FIG. 4C), wild-type mice on high-fat chow diet (FIG. 4D), and LDLR−/− mice on high-fat chow diet (FIG. 4A).

Figures 4A, 4B, 4C, 4D, 4E, 4F, 4G:
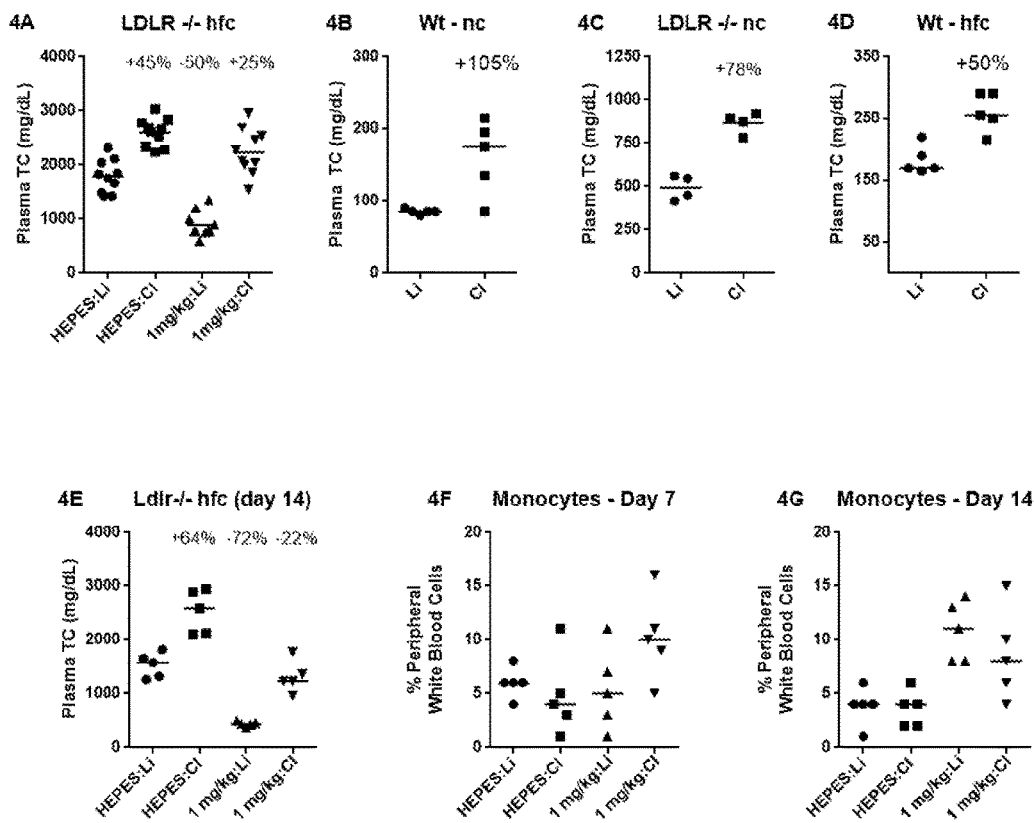
FIGS. 4A-4G illustrate the results of an assessment conducted in order to determine whether cells associated with the myeloid lineage were responsible for the control of plasma cholesterol by PEG-rMuIL-10.
Figures 5A, 5B, 5C, 5D:
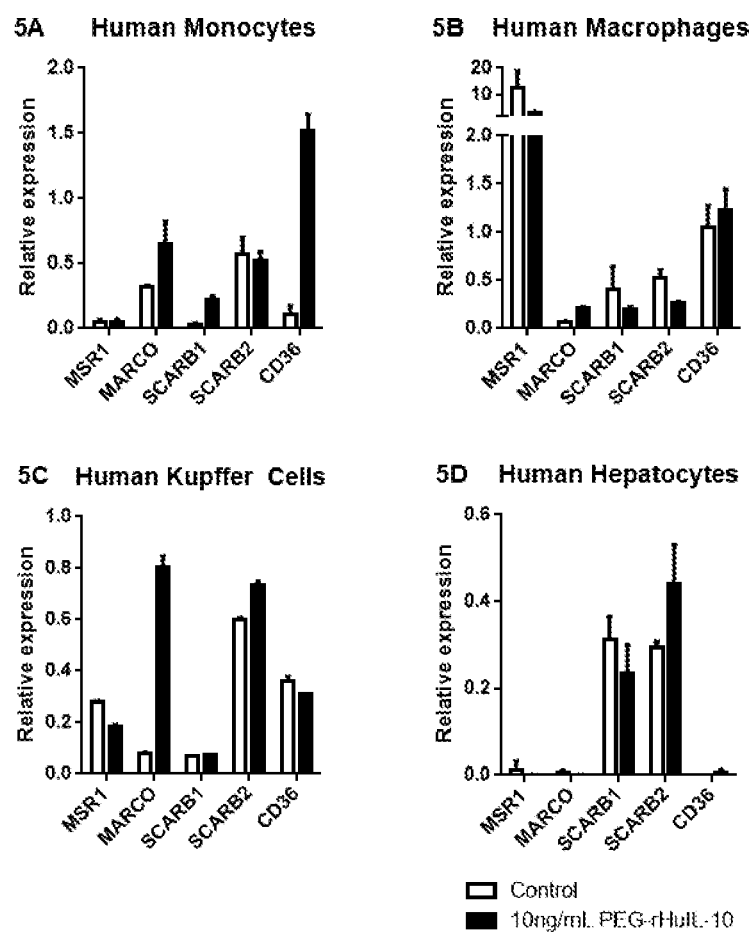
FIGS. 5A-5D illustrate the results of an assessment conducted in order to determine which cells in the liver respond to PEG-rHuIL-10.

As indicated in FIGS. 4A-4G, depletion of phagocytotic cells abolished the regulation of PEG-rMuIL-10 of plasma cholesterol. PEG-rMuIL-10-dosed mice (1 mg/kg) exhibited a 50% decrease in cholesterol, while mice dosed with both PEG-rMuIL-10 and clodronate liposome had a 25% increase (FIG. 4A). Unexpectedly, the mice that received only clodronate exhibited a 45% increase in total plasma cholesterol. Thereafter, phagocytotic cells were depleted in wild type and LDLR−/− mice on normal chow diet (FIGS. 4B and 4C, respectively), and wt mice on high fat chow diet (FIG. 4D). Surprisingly, removal of phagocytotic cells consistently increased plasma cholesterol, suggesting phagocytotic cells in general are implicit in the normal regulation of plasma cholesterol.

IHC assessment indicated that PEG-rMuIL-10 exerted no effect on clodronate-mediated depletion of liver Kupffer cells at day 7, but that PEG-rMuIL-10 had begun to facilitate the repopulation of Kupffer cells in the liver by day 14 (data not shown). As indicated in FIG. 4E, PEG-rMuIL-10's repopulation of liver Kupffer cells is consistent with a decrease in plasma cholesterol.

Dosing with PEG-rMuIL-10 appeared to enhance the entry of monocytes from the bone marrow into the systemic circulation. As indicated in FIGS. 4F and 4G, there is an initial decrease of peripheral monocytes of mice after exposure to clodronate. PEG-rMuIL-10 then acted to facilitate the recovery of this cell population. These data suggest that dosing with PEG-rMuIL-10 may slowly restore homeostasis, overcoming the effects of clodronate and enhancing the repopulation of Kupffer cells in the liver, thereby reestablishing their ability to lower cholesterol.

EXAMPLE 5

PEG-rHuIL-10 Induces Scavenger Receptor Expression in Human Myeloid Lineage

To specifically determine which cells in the liver respond to PEG-rHuIL-10, in vitro experiments were conducted wherein human monocytes (FIG. 5A), human macrophages (FIG. 5B), human Kupffer cells (FIG. 5C), and human hepatocytes (FIG. 5D) were exposed to PEG-rHuIL-10. Referring to FIGS. 5A-5D, only the Kupffer cells and peripheral monocytes showed an upregulation of scavenger receptor expression in response to PEG-rHuIL-10.

These data suggest that PEG-rHuIL-10 upregulates scavenger receptor expression on myeloid lineage cells, but not hepatocytes. Of note, scavenger receptor regulation appeared to be similar in mice and humans, suggesting a conservation of IL-10's biology with regard to effects on the myeloid compartment.

EXAMPLE 6

PEG-rHuIL-10 Increases Monocyte Uptake of Modified LDL and LDL Uptake by Kupffer Cells In order to determine if the increased expression of scavenger receptors correlates with enhanced uptake of lipoproteins, peripheral human monocytes (FIGS. 6A, 6E and 6F), human macrophages (FIG. 6B), human Kupffer cells (FIG. 6C), and human hepatocytes (FIG. 6D) were isolated and exposed to PEG-rHuIL-10.

Referring to FIGS. 6A-6D, the Y-axis is the quantitation of the amount of labeled cholesterol that has been taken up relative to a standard curve dilution of the same labeled cholesterol. The parameters on the X-axis can be briefly summarized as follows: cells were exposed to PEG-IL-10 for ~24 hours, then washed and exposed for 3-5 hours to i) nothing with no labeled cholesterol to act as the background control, ii) nothing with the labeled cholesterol to act as the background control, or iii) PEG-IL-10 with the labeled cholesterol. Cells were washed, lysed, and then the total internalized labeled cholesterol was quantified as indicated above. The data in FIGS. 6E and 6F was generated in a similar manner.

Figures 6A, 6B, 6C, 6D, 6E, 6F:
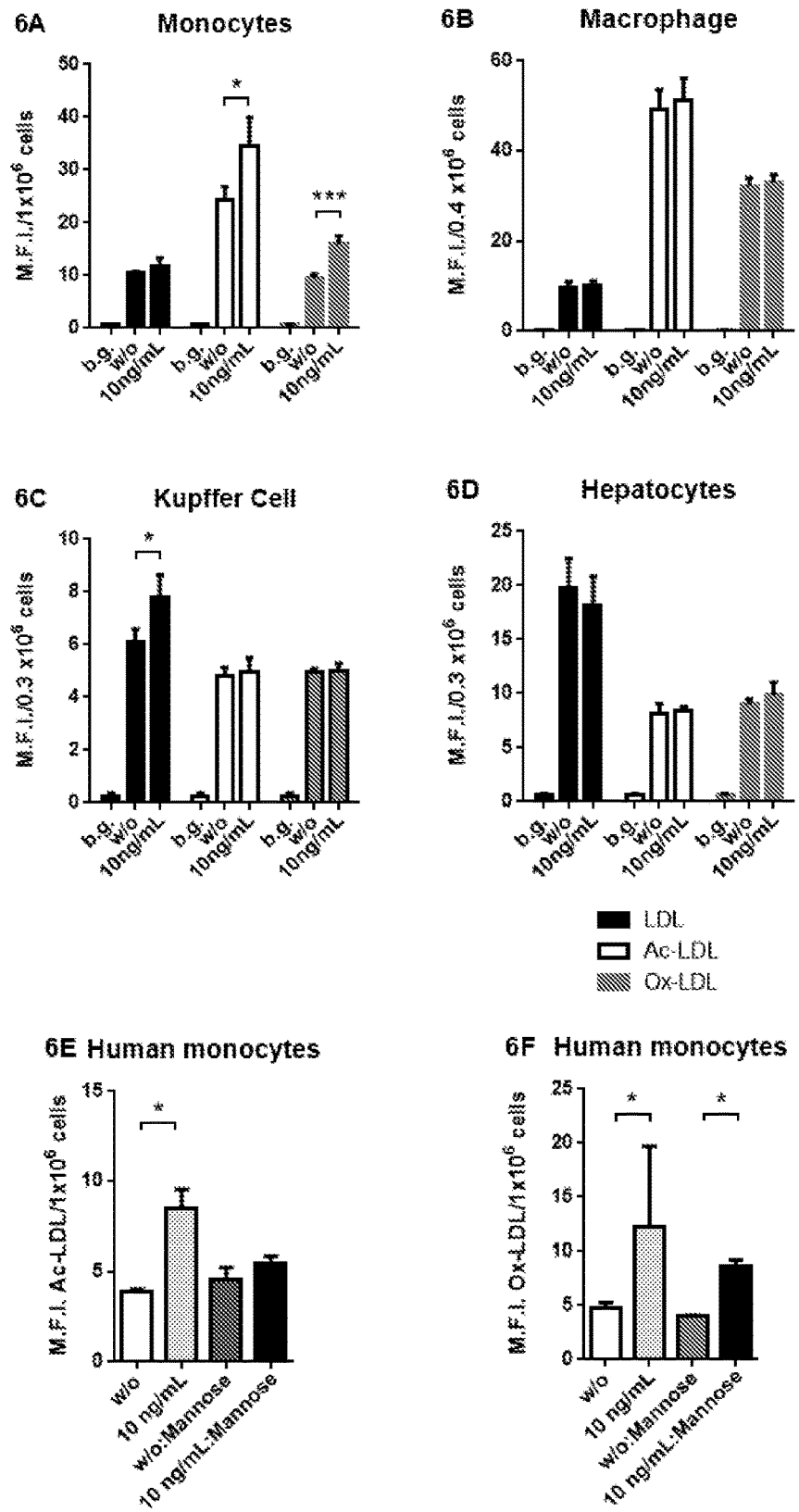
FIGS. 6A-6F illustrate that PEG-rHuIL-10 increases the uptake of acetylated LDL (Ac-LDL) and oxidized LDL (Ox-LDL) in monocytes, and the update of LDL in Kupffer cells.

As indicated in FIG. 6A, PEG-rHuIL-10 increased the uptake of acetylated LDL (Ac-LDL; *, p<0.05) and oxidized LDL (Ox-LDL; *, p<0.001), but not unmodified LDL (LDL), by freshly isolated peripheral blood monocytes. FIGS. 6E and 6F exhibit the effect of PEG-rHuIL-10 and PEG-rHuIL-10 plus mannose on acetylated LDL (FIG. 6E) and oxidized LDL (FIG. 6F) in human monocytes. Mannose was used to block the mannose receptor. Blockade of the mannose receptor inhibited the uptake of acetylated LDL, although not the uptake of oxidized LDL (FIGS. 6E and 6F**, respectively). These data suggest that PEG-rHuIL-10 enhances the scavenging of LDL proteins via the upregulation of both canonical and non-canonical scavenger receptors.

In contrast, no differences were detected in any form of LDL uptake by Macrophage colony-stimulating factor (M-CSF)-differentiated macrophages in response to PEG-rHuIL-10 (FIG. 6B). Referring to FIG. 6C, PEG-rHuIL-10 increased Kupffer cell uptake of LDL (*, p<0.05), but not Ac-LDL or Ox-LDL. These data support the involvement of Kupffer cells in the regulation of plasma LDL cholesterol. The presence of alterations to hepatocyte uptake of unmodified, oxidized and acetylated LDL was also assessed. In response to PEG-rHuIL-10, no alterations to hepatocyte uptake of unmodified, oxidized and acetylated LDL were observed (FIG. 6D). While myeloid lineage cells are generally phagocytotic, these data show that the nature of cholesterol uptake is different between monocytes, macrophages, Kupffer cells, and hepatocytes in response to PEG-rHuIL-10.

When neutralizing antibodies to MARCO and CD36, as potential inhibitors of PEG-rHuIL-10's effect on cholesterol uptake, were evaluated, no differences in uptake were observed (data not shown). In contrast, dextran inhibited PEG-rHuIL-10's increase in Ac-LDL but not Ox-LDL uptake by monocytes (data not shown). These data suggest that PEG-rHuIL-10's control of lipoprotein uptake occurs through both known and possibly unknown scavenger receptor regulation. Moreover, consistent with efflux gene regulation in vivo, exposure of Kupffer cells to IL-10 caused a moderate increase in efflux of cholesterol onto HDL particles (data not shown).

In their totality, these data indicate that while PEG-rHuIL-10 can enhance the uptake of Ac-LDL and Ox-LDL by peripheral monocytes, the Kupffer cell population within the liver is the target cell population for PEG-rHuIL-10-mediated control of peripheral cholesterol. Furthermore, these data implicate the myeloid lineage in the control of peripheral cholesterol, suggesting that monocytes, macrophages, and Kupffer cells represent an untapped cellular reservoir within the liver that actively removes plasma cholesterol. Finally, these data indicate that the modulation of scavenger receptors on Kupffer cells with PEG-rHuIL-10, as well as the general modulation of myeloid lineage with other therapeutic compounds, may represent an alternative means for reducing plasma cholesterol.

EXAMPLE 7

PEG-rMuIL-10 is Additive with Ezetimibe in Cholesterol Lowering

In order to assess whether the PEG-rMuIL-10-mediated effects observed in the previous examples were consistent with the utilization of a cell type not currently targeted by standard of care therapeutics, PEG-rMuIL-10 was combined with an orally administered statin or ezetimibe, an oral therapeutic agent that blocks cholesterol absorption.

Figure 7A:
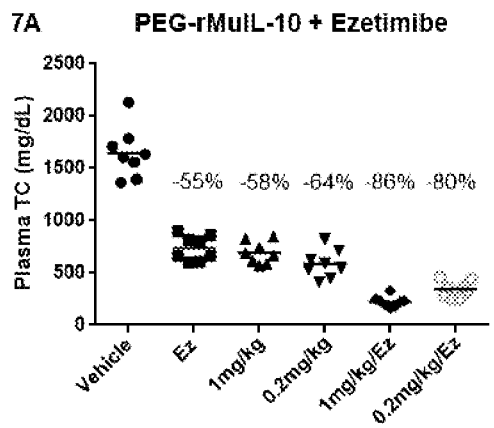
FIGS. 7A-7C illustrate that the effect on cholesterol lowering of PEG-rMuIL-10 and Ezetimibe is additive.

As illustrated in FIG. 7A, when administered to LDLR −/− mice on high fat diet, PEG-rMuIL-10 (1.0 mg/kg SC daily) and Ezetimibe (Ez) (10 mg/kg daily via oral gavage) individually lowered plasma cholesterol by 58% and 55%, respectively, and by up to 86% when combined. The plasma cholesterol concentration observed with administration of PEG-rMuIL-10 and Ezetimibe was similar to that of normal plasma cholesterol levels observed in LDLR −/− mice.

Figure 7B:
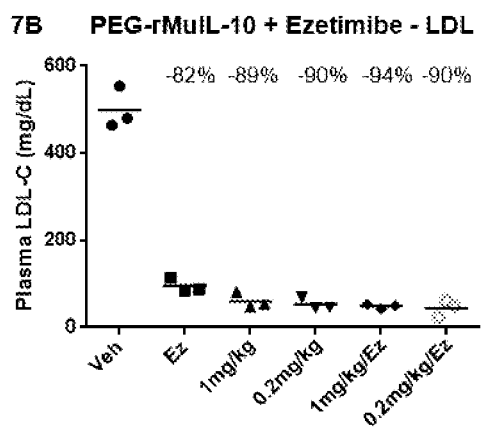
Figure 7C:
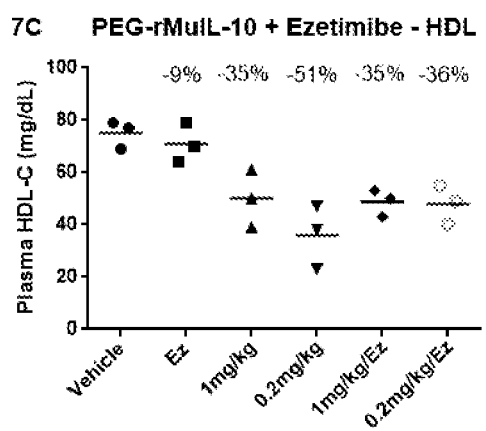

Data associated with plasma LDL-C and plasma HDL-C were generated using an experimental approach comparable to that which gave rise to the data in FIG. 7A. As indicated in FIGS. 7A and 7B, combination of PEG-rMuIL-10 and Ezetimibe resulted in reduction of LDL-C and HDL-C, respectively. Although combination of PEG-rMuIL-10 and statin (simvastatin) also reduced LDL-C and HDL-C (data not shown), oral administration of statin is toxic in mice, and therefore the maximal level of plasma lowering achieved with statin was limited. The combination of PEG-rMuIL-10 with both Ezetimibe and statin suggests that the mechanism of action of each agent is non-redundant.

EXAMPLE 8

PEG-rMuIL-10 Decreases the Accumulation of Lipids, Cholesterol and Triglycerides An evaluation was conducted to determine the scavenger effect on plasma cholesterol of PEG-rMuIL-10-mediated activation of Kupffer cells.

Figures 8A, 8B, 8C, 8D, 8E, 8F, 8G, 8H, 8I:
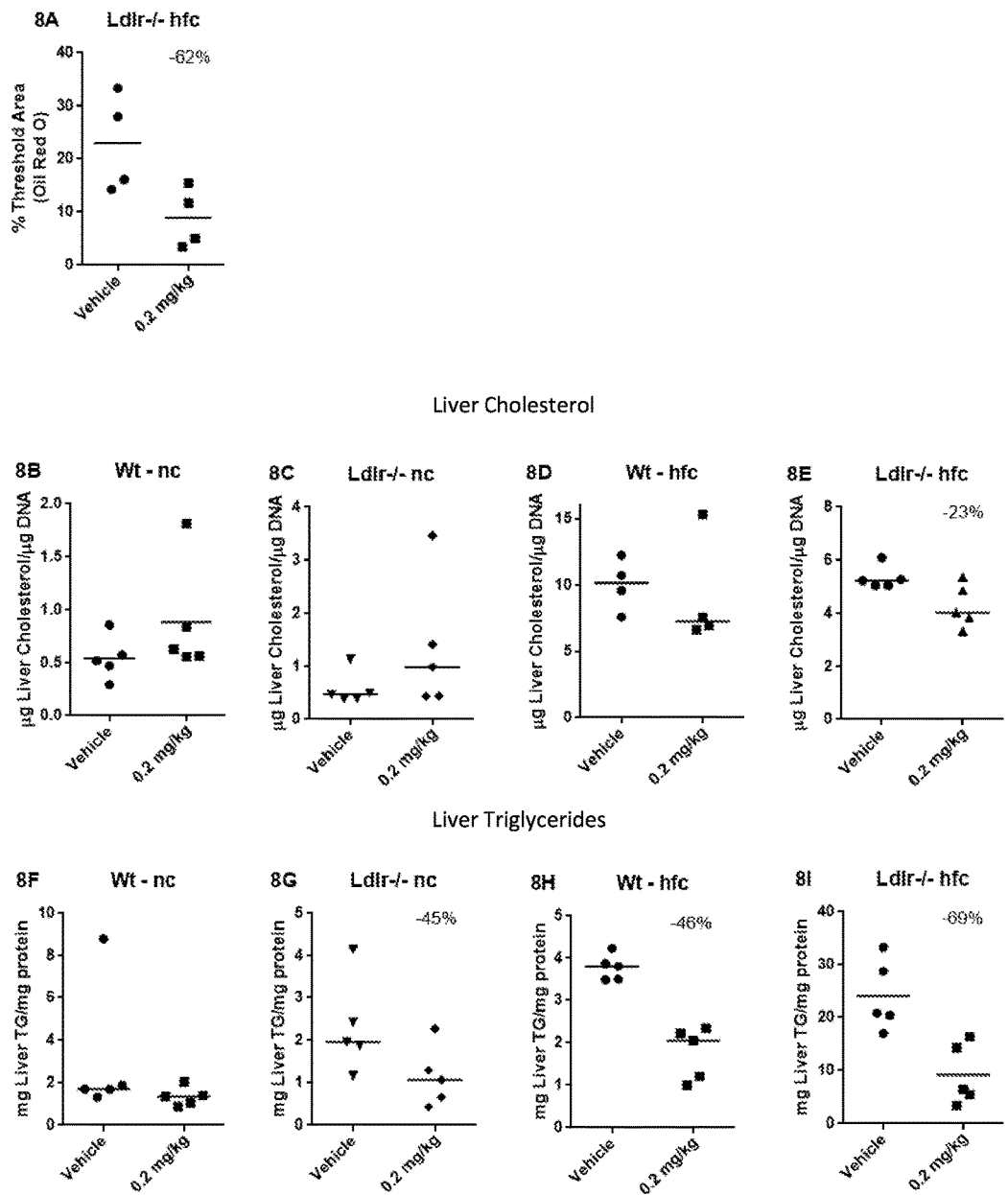
FIGS. 8A-8I illustrate that Kupffer cells play a role in the reduction of the accumulation of lipids, cholesterol and triglycerides observed with the introduction of PEG-rMuIL-10.

As determined by assessment of hepatic lipid concentrations by Oil Red O staining (data not shown), treatment with PEG-rMuIL-10 decreased hepatic lipid droplets in LDLR−/− mice fed high fat chow (FIG. 8A). In addition, hepatic tissue concentrations of cholesterol and triglycerides were quantified. As illustrated in FIGS. 8B-8E, hepatic cholesterol concentrations only trended lower in wt and LDLR−/− mice fed the high fat diet; mice receiving a normal diet did not exhibit an appreciable effect. FIGS. 8E-8I indicated that hepatic triglyceride concentrations were lower in the wt mice fed the high fat diet, and the LDLR−/− mice fed both the both normal diet and high fat diet. In their totality, these data indicate that both i) the engagement of the scavenging system whereby plasma lipoproteins are removed by Kupffer cells, and ii) the moderately enhanced efflux onto HDL lipoproteins (data not shown), are sufficient to prevent inappropriate triglyceride and cholesterol accumulation within the Kupffer cells and hepatocytes.

EXAMPLE 9

PEG-rMuIL-10 Treatment Results in Hepatocyte Proliferation

Figure 9A:
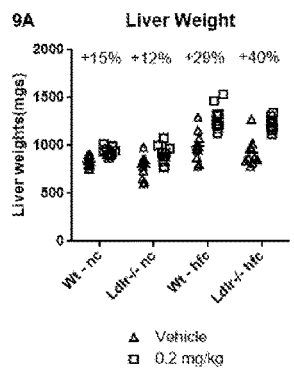
FIGS. 9A-9I illustrate that treatment of animals having the indicated backgrounds with PEG-rMuIL-10 resulted in hepatocyte proliferation.
Figure 9B:
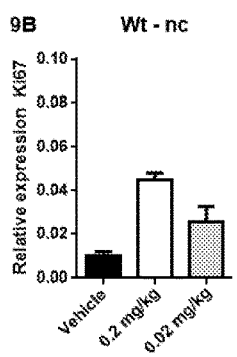
Figure 9C:
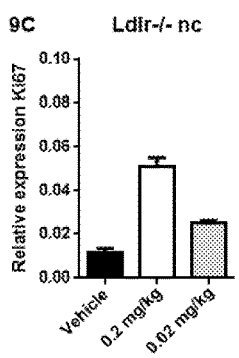
Figure 9D:
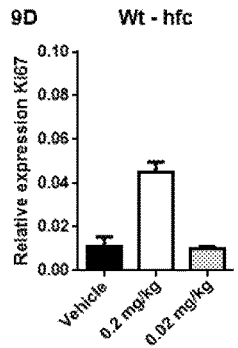
Figure 9E:
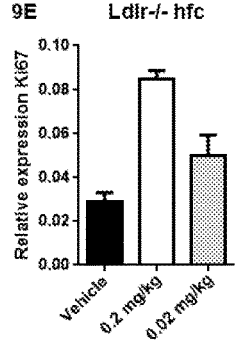
Figure 9F:
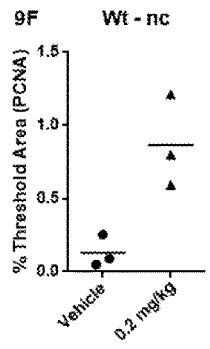
Figure 9G:
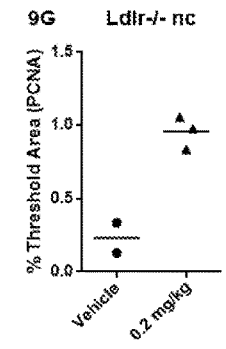
Figure 9H:
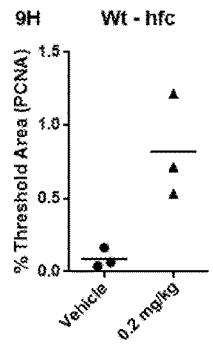
Figure 9I:
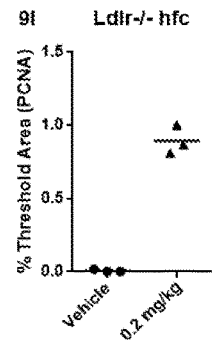

Administration of PEG-rMuIL-10 resulted in increased numbers of peri-portal cells in LDLR−/− mice (data not shown), reflecting an apparent decrease in steatotic cells consistent with the decrease in liver triglycerides observed in the preceding example. As depicted in FIG. 9A, an increase in liver weight was observed that was diet- (normal diet vs. high fat diet) and strain-independent (wt vs. LDLR−/−), but dose-related (data not shown). Ki67 gene expression was quantified in order to determine whether that observation was reflective of proliferation in the liver. As illustrated in FIGS. 9B-E, gene expression was increased more than 2-fold in wt and LDLR−/− mice fed a normal diet and in wt and LDLR−/− mice fed a high fat diet when animals were treated with 0.2 mg/kg PEG-rMuIL-10 (but not 0.02 mg/kg PEG-rMuIL-10).

In order to determine which cells were dividing, cells were stained for proliferating cell nuclear antigen (PCNA) by IHC, and an increase in PCNA-positive cells was observed in both wt mice fed normal chow and LDLR−/− mice fed high fat chow (data not shown). As indicated in FIGS. 9F-9I PEG-rMuIL-10 dosing led to increases in PCNA-positive cells in all mice backgrounds. PCNA-positive cells appeared to be both hepatocytes and cells entering into the liver via the portal duct.

EXAMPLE 10

PEG-rMuIL-10 Exhibits an Anti-fibrotic Effect

Triglyceride accumulation in the liver is considered causative of fatty liver disease, and long-term accumulation has been linked to the development of NASH (see, e.g., Liu, Q., et al., Lipids Health Dis, 2010. 9:42). Fatty liver disease is believed to progress to cirrhosis, which is associated with the deposition of collagen by activated hepatic stellate cells. IL-10 inhibits secretion of collagen from these cells. Therefore, an assessment was conducted to determine whether treatment of normal and hyperlipidemic wild type and LDLR−/− mice with PEG-rMuIL-10 results in changes in hepatic collagen deposition.

Comparison of representative liver peri-portal regions from wt and LDLR−/− mice fed normal and high fat chow indicted that LDLR−/− mice fed a high fat diet had the greatest changes to peri-portal collagen deposition (data not shown). These data suggest that treatment with PEG-rMuIL-10 may inhibit the deposition of peri-portal collagen, consistent with IL-10's reported anti-fibrotic function. Further assessment indicated that peri-portal collagen deposition in response to the inflammatory stimulus derived from high plasma cholesterol can be restored to normal by PEG-rMuIL-10 dosing. Consistent with these data, PEG-rMuIL-10 also decreased liver triglycerides in these animals (data not shown).

Taken together, these data suggest that PEG-rMuIL-10 may restore liver health by inducing hepatocyte proliferation, decreasing hepatic triglyceride concentrations, and remodeling inappropriately deposited collagen. Accumulation of hepatic triglyceride and subsequent collagen deposition are hallmarks of NAFLD that, if left unchecked, develop into NASH. Because treatment with PEG-rMuIL-10 reduces these causative factors, PEG-IL-10 represents a potential therapeutic modality for the treatment of NAFLD and NASH.

EXAMPLE 11

Effect of PEG-rMuIL-10 on Liver Function

A possible link between exposure of mice to PEG-rMuIL-10 and hepatotoxicity was explored. As set forth in Table 1, an assessment of changes to liver function serum markers indicated that PEG-rMuIL-10 did not dramatically change liver serum function markers relative to normal murine controls.

TABLE 1

| Liver Function Serum Marker | Control Median Range | 0.2 mg/kg Median Range | Normal Mouse Range |
| --- | --- | --- | --- |
| ALT (IU/L) | 20-74 | 34.5-122 | 17-77 |
| AST (IU/L) | 73-162 | 68-136 | 54-298 |
| Albumin (g/dL) | 2-2.9 | 2.4-3 | 2.5-3 |
| Total Protein (g/dL) | 4.4-5.5 | 4.6-5.1 | 3.5-7.2 |
| Alkaline Phosphatase (IU/L) | 89.5-121 | 26.5-49 | 3.5-96 |
| Glucose (g/dL) | 202-278 | 240-281 | 62-175 |
| Total Bilirubin (mg/dL) | 0-0.35 | 0.1-0.3 | 0-0.9 |
| Phosphorus (mg/dL) | 4.6-6.8 | 5.25-7.4 | 5.7-9.2 |
| Blood Urea Nitrogen (mg/dL) | 17.5-28 | 16-25 | 8-33 |
| Creatine Phosphokinase (IU/L) | 109-417 | 172-329 | 105-649 |

Thus, while exposures of hypercholesterolemic mice to PEG-rMuIL-10 resulted in certain changes in liver biology, those changes did not induce toxic primary or secondary effects. These data further support the potential use of PEG-rHuIL-10 in controlling high plasma cholesterol and the concomitant beneficial effects on NAFLD and NASH.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of treating non-alcoholic steatohepatitis (NASH) or non-alcoholic fatty liver disease (NAFLD) in a subject, the method comprising: administering parenterally to a subject having NASH or NAFLD a therapeutically effective amount of a composition comprising a PEGylated interleukin-10 (PEG-IL-10) agent, wherein the amount is sufficient to maintain an IL-10 serum trough concentration from 1.0 pg/mL to 10.0 ng/mL, over a period of time of at least 24 hours.

2. The method of claim 1, wherein the PEG-IL-10 agent comprises mature human IL-10.

3. The method of claim 1, wherein the PEG-IL-10 agent comprises a variant of mature human IL-10, and wherein the variant exhibits activity comparable to the activity of mature human IL-10.

4. The method of claim 1, wherein said administering is effective to decrease cholesterol in the subject.

5. The method of claim 1, wherein said administering is effective to decrease triglycerides in the subject.

6. The method of claim 1, wherein said administering is effective to decrease peri-portal collagen deposition in the subject.

7. The method of claim 1, wherein said administering is effective to increase hepatocyte proliferation in the subject.

8. The method of claim 1, wherein said administering is subcutaneous.

9. The method of claim 1, wherein the method comprises administering at least one additional prophylactic or therapeutic agent.

10. The method of claim 1, wherein the PEG-IL-10 agent comprises at least one PEG molecule covalently attached to at least one amino acid residue of at least one subunit of IL-10.

11. The method of claim 1, wherein the PEG-IL-10 agent comprises a mixture of mono-pegylated and di-pegylated IL-10.

12. The method of claim 1, wherein the PEG component of the PEG-IL-10 agent has a molecular mass from about 5 kDa to about 20 kDa.

13. The method of claim 1, wherein the PEG component of the PEG-IL-10 agent has a molecular mass greater than about 20 kDa.

14. The method of claim 1, wherein the PEG component of the PEG-IL-10 agent has a molecular mass of at least about 30 kD.

15. The method of claim 1, wherein the subject is a human.

16. A method of treating hypercholesterolemia or a hypercholesterolemia-associated disease, disorder or condition in a subject having non-alcoholic steatohepatitis (NASH) or non-alcoholic fatty liver disease (NAFLD), the method comprising: administering parenterally to the subject a composition comprising PEGylated interleukin-10 (PEG-IL-10) agent and a composition comprising ezetimibe,
wherein said administering is effective to reduce cholesterol in the subject and wherein the amount is sufficient to maintain an IL-10 serum trough concentration from 1.0 pg/mL to 10.0 ng/mL, over a period of time of at least 24 hours.

17. The method of claim 16, wherein the composition comprising PEG-IL-10 and the composition comprising a ezetimibe are administered sequentially.

18. The method of claim 16, wherein the PEG-IL-10 agent comprises mature human IL-10.

19. The method of claim 16, wherein the PEG-IL-10 agent comprises a variant of mature human IL-10, and wherein the variant exhibits activity comparable to the activity of mature human IL-10.

20. The method of claim 16, wherein said administering of the composition comprising the PEG-IL-10 agent is subcutaneous.

21. The method of claim 16, wherein the PEG-IL-10 agent comprises at least one PEG molecule covalently attached to at least one amino acid residue of at least one subunit of IL-10.

22. The method of claim 16, wherein the PEG-IL-10 agent comprises a mixture of mono-pegylated and di-pegylated IL-10.

23. The method of claim 16, wherein the PEG component of the PEG-IL-10 agent has a molecular mass from about 5 kDa to about 20 kDa.

24. The method of claim 16, wherein the PEG component of the PEG-IL-10 agent has a molecular mass greater than about 20 kDa.

25. The method of claim 16, wherein the PEG component of the PEG-IL-10 agent has a molecular mass of at least about 30 kD.

26. The method of claim 16, wherein the subject is a human.

* * * * *

SEQUENCE LISTING

```
<160> NUMBER OF SEQ ID NOS: 10

<210> SEQ ID NO 1
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 1

Tyr Gly Arg Lys Lys Arg Arg Gln Arg Arg
1               5                   10
```

<210> SEQ ID NO 2
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 2

Arg Arg Gln Arg Arg Thr Ser Lys Leu Met Lys Arg
1               5                   10

<210> SEQ ID NO 3
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 4

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 5
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 6

Arg Lys Lys Arg Arg Gln Arg Arg Arg
1               5

<210> SEQ ID NO 7
<211> LENGTH: 8
<212> TYPE: PRT
<213> ORGANISM: Artificial Sequence

```
<220> FEATURE:
<223> OTHER INFORMATION: synthetic polypeptide

<400> SEQUENCE: 7

Arg Lys Lys Arg Arg Gln Arg Arg
1               5

<210> SEQ ID NO 8
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 8

Tyr Ala Arg Ala Ala Ala Arg Gln Ala Arg Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 9

Thr His Arg Leu Pro Arg Arg Arg Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 10

Gly Gly Arg Arg Ala Arg Arg Arg Arg Arg Arg
1               5                   10
```